(12) United States Patent
Dubensky, Jr. et al.

(10) Patent No.: US 9,878,024 B2
(45) Date of Patent: *Jan. 30, 2018

(54) **METHODS AND COMPOSITIONS USING *LISTERIA* FOR ENHANCING IMMUNOGENICITY BY PRIME BOOST**

(71) Applicant: ADURO BIOTECH, INC., Berkeley, CA (US)

(72) Inventors: Thomas W. Dubensky, Jr., Berkeley, CA (US); Dirk G. Brockstedt, Richmond, CA (US); Meredith Lai Ling Leong, Oakland, CA (US); Keith S. Bahjat, Concord, CA (US)

(73) Assignee: ADURO BIOTECH, INC., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/952,281

(22) Filed: Nov. 25, 2015

(65) Prior Publication Data
US 2016/0175415 A1 Jun. 23, 2016

Related U.S. Application Data

(63) Continuation of application No. 14/589,608, filed on Jan. 5, 2015, now Pat. No. 9,198,960, which is a continuation of application No. 12/374,288, filed as application No. PCT/US2007/016290 on Jul. 17, 2007, now Pat. No. 8,926,993.

(60) Provisional application No. 60/831,360, filed on Jul. 17, 2006.

(51) Int. Cl.
A61K 39/00 (2006.01)

(52) U.S. Cl.
CPC .. *A61K 39/0011* (2013.01); *A61K 2039/5152* (2013.01); *A61K 2039/521* (2013.01); *A61K 2039/522* (2013.01); *A61K 2039/523* (2013.01); *A61K 2039/53* (2013.01); *A61K 2039/545* (2013.01); *C12N 2799/022* (2013.01); *C12N 2799/023* (2013.01)

(58) Field of Classification Search
None
See application file for complete search history.

(56) References Cited

U.S. PATENT DOCUMENTS

| | | | |
|---|---|---|---|
| 6,787,351 B2 | 9/2004 | Chen et al. | |
| 7,935,804 B2 | 5/2011 | Dubensky, Jr. et al. | |
| 8,926,993 B2* | 1/2015 | Dubensky, Jr. | A61K 39/0011 424/234.1 |
| 9,198,960 B2* | 12/2015 | Dubensky, Jr. | A61K 39/0011 |
| 2002/0150588 A1 | 10/2002 | Allison et al. | |
| 2003/0158134 A1 | 8/2003 | Voss | |
| 2004/0091995 A1 | 5/2004 | Schlom et al. | |
| 2004/0197343 A1 | 10/2004 | Dubensky et al. | |
| 2004/0228877 A1 | 11/2004 | Dubensky, Jr. et al. | |
| 2005/0249748 A1 | 11/2005 | Dubensky, Jr. et al. | |
| 2005/0281783 A1 | 12/2005 | Kinch et al. | |
| 2007/0207170 A1 | 9/2007 | Dubensky et al. | |

FOREIGN PATENT DOCUMENTS

| | | |
|---|---|---|
| WO | 1990014837 A1 | 12/1990 |
| WO | 1992019265 A1 | 11/1992 |
| WO | 1993013202 A1 | 7/1993 |

OTHER PUBLICATIONS

Carine et al., Mouse Strain Differences in Plasmacytoid Dendritic Cell Frequency and Function Revealed by a Novel Monoclonal Antibody. J Immunol. Dec. 15, 2003;171(12):6466-6477.

Carr et al., Genetic Variation in Clinical Varicella-Zoster Virus Isolates Collected in Ireland Between 2002 and 2003. J Med Virol. May 2004;73(1):131-136.

Casimiro et al., Attenuation of Simian Immunodeficiency Virus SIVmac239 Infection by Prophylactic Immunization with DNA and Recombinant Adenoviral Vaccine Vectors Expressing Gag. J Virol. Dec. 2005;79(24):15547-15555.

Cassetti et al., Antitumor efficacy of Venezuelan equine encephalitis virus replicon particles encoding mutated HPV16 E6 and E7 genes. Vaccine Jan. 2, 2004;22(3-4):520-527.

Castaldello et al., DNA prime and protein boost immunization with innovative polymeric cationic core-shell nanoparticles elicits broad immune responses and strongly enhance cellular responses of HIV-1 tat DNA vaccination. Vaccine Jul. 17, 2006;24(29-30):5655-5669.

Cebere et al., Phase I clinical trial safety of DNA- and modified virus Ankara-vectored human immunodeficiency virus type 1 (HIV-1) vaccines administered alone and in a prime-boost regime to healthy HIV-1-uninfected volunteers. Vaccine Jan. 23, 2006;24(4):417-425.

Cerundolo et al., Dendritic cells: a journey from laboratory to clinic. Nature Immunol. Jan. 2004;5(1):7-10.

Chakir et al., Differentiation of Murine NK Cells into Distinct Subsets Based on Variable Expression of the IL-12Rbeta2 Subunit. J Immunol. Nov. 1, 2000; 165(9):4985-4993.

Chan et al., In Situ Hybridization Study of PSP94 (Prostatic Secretory Protein of 94 Amino Acids) Expressionin Human Prostates. Prostate Oct. 1, 1999;41(2):99-109.

Chang et al., A Phase I Trial of Tumor Lysate-pulsed Dendritic Cells in the Treatment of Advanced Cancer. Clin Cancer Res. Apr. 2002;8(4):1021-1032.

Chang et al., Antigen-Specific Cancer Immunotherapy Using a Gm-Csf Secreting Allogeneic Tumor Cell-Based Vaccine. Int J Cancer Jun. 1, 2000;86(5):725-730.

(Continued)

*Primary Examiner* — Jennifer Graser
(74) *Attorney, Agent, or Firm* — Acuity Law Group, PC; Michael A. Whittaker

(57) ABSTRACT

Provided herein are prime-boost regimens and materials used therein. The prime-boost regimens enhance the immune response to a target antigen. The vaccines used for boost are comprised of recombinant attenuated metabolically active *Listeria* that encodes an expressible antigen that is cross-reactive with the target antigen. In some examples, the immune response is a cellular immune response.

10 Claims, 16 Drawing Sheets

(56) References Cited

OTHER PUBLICATIONS

Chen et al., Immunodominant CD4+ responses identified in a patient vaccinated with full-length NY-ESO-1 formulated with ISCOMATRIX adjuvant. Proc Natl Acad Sci. USA. Jun. 22, 2004;101(25):9363-9368.

Cheng et al., Cancer Immunotherapy Using Sindbis Virus Replicon Particles Encoding a VP22-Antigen Fusion. Hum Gene Ther. Mar. 1, 2002;13(4):553-568.

Chern et al., Glycoprotein B Subtyping of Cytomegalovirus (CMV) in the Vitreous of Patients with AIDS and CMV Retinitis. J Infect Dis. Oct. 1998;178(4):1149-1153.

Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.

Christiansen et al., Polarity of Prostate Specific Membrane Antigen, Prostate Stem Cell Antigen, and Prostate Specific Antigen in Prostate Tissue and in a Cultured Epithelial Cell Line. Prostate Apr. 1, 2003;55(1):9-19.

Clemens et al., The *Mycobacterium tuberculosis* Phagosome in Human Macrophages is Isolated from the Host Cell Cytoplasm. Infect Immun. Oct. 2002;70(10):5800-5807.

Clements et al., Adenomatous Polyposis Colifbeta-Catenin Interaction and Downstream Targets: Altered Gene Expression in Gastrointestinal Tumors. Clin Colorectal Cancer Aug. 2003;3(2):113-120.

Clifton et al., A chlamydial type III translocated protein is tyrosine-phosphorylated at the site of entry and associated with recruitment of actin. Proc Natl Acad Sci. USA Jul. 6, 2004;101(27):10166-10171.

Clinton et al., A Comparative Study of Four Serological Tumor Markers for the Detection of Breast Cancer. Biomed Sci Instrum. 2003;39:408-414.

Cobaleda et al., A primitive hematopoietic cell is the target for the leukemic transformation in human Philadelphia-positive acute lymphoblastic leukemia. Blood Feb. 2000;95(3):1007-1013.

Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.

Cossart, Molecular and cellular basis of the infection by Listeria monocytogenes: an overview. Int J Med Microbial. Feb. 2002;291(6-7):401-409.

Couedel et al., Diverse CD1d-restricted reactivity patterns of human T cells bearing "invariants" AV24BV11 TCR. Eur J Immunol. Dec. 1998;28(12):4391-4397.

Coupar et al., Fowlpox virus vaccines for HIV and SHIV clinical and pre-clinical trials. Vaccine Feb. 27, 2006;24(9):1378-1388.

Cristillo et al., Preclinical evaluation of cellular immune responses elicited by a polyvalent DNA prime/protein boost HIV-1 vaccine. Virology Mar. 1, 2006;346(1):151-168.

Dalerba et al., MAGE, BAGE and GAGE Gene Expression in Human Rhabdomyosarcomas. Int J Cancer Jul. 1, 2001;93(1):85-90.

Damasus-Awatai and Freeman-Wang, Human papilloma virus and cervical screening. Curr. Opin. Obstet Gynecol. Dec. 2003;15(6):473-477.

Das et al., Evaluation of a Western Equine Encephalitis recombinant E1 protein for protective immunity and diagnostics. Antiviral Res. Nov. 2004;64(2):85-92.

Dasilva et al., Heterologous boosting increases immunogenicity of chimeric papillomavirus virus-like particle vaccines. Vaccine Jul. 4, 2003;21(23):3219-3227.

Davies et al., Characterisation of a recombinant Fv fragment of anti-MUC1 antibody HMFG1. Cancer Lett. Jul. 29, 1994;82(2):179-184.

De Backer et al., Characterization of the GAGE Genes That are Expressed in Various Human Cancers and in Normal Testis. Cancer Res. Jul. 1, 1999;59(13):3157-3165.

De Villiers et al., Classification of papillomaviruses. Virology. Jun. 20, 2004;324(1):17-27.

Dean, Epidermal delivery of protein and DNA vaccines. Expert Opin Drug Deliv. Mar. 2005;2(2):227-236.

Dela Cruz et al., Protein vaccination with the HER2/neu extracellular domain plus anti-HER2/neu antibody-cytokine fusion proteins induces a protective anti-HER2/neu immune response in mice. Vaccine Mar. 28, 2003;21(13-14):1317-1326.

Demidenko and Blagosklonny, Flavopiridol Induces p53 via Initial Inhibition of Mdm2 and p21 and, Independently of p53, Sensitizes Apoptosis-Reluctant Cells to Tumor Necrosis Factor. Cancer Res. May 15, 2004;64 (10):3653-3660.

Depolo et al., VSV-G Pseudotyped Lentiviral Vector Particles Produced in Human Cells are Inactivated by Human Serum Mol Ther. Sep. 2000;2(3):218-222.

Dinicola et al., Boosting T Cell-Mediated Immunity to Tyrosinase by Vaccinia Virus-Transduced, CD34+-Derived Dendritic Cell Vaccination: A Phase I Trial in Metastatic Melanoma. Clin Cancer Res. Aug. 15, 2004;10(16):5381-5390.

Disis and Cheever, HER-2/neu Protein: A Target for Antigen-Specific Immunotherapy of Human Cancer. Adv Cancer Res. 1997;71:343-371.

Disis et al., Humoral Epitope-Spreading Following Immunization with a HER-2/neu Peptide Based Vaccine in Cancer Patients. J Clin Immunol. Sep. 2004;24(5):571-578.

Disis et al., Peptide-Based, but Not Whole Protein, Vaccines Elicit Immunity to HER-2/neu, an Oncogenic Self-Protein. J Immunol. May 1, 1996;156(9):3151-3158.

Doe et al., Induction of HIV-1 envelope (gp120)-specific cytotoxic T lymphocyte responses in mice by recombinant CHO cell-derived gp120 is enhanced by enzymatic removal of N-linked glycans. Eur J Immunol. Oct. 1994;24(10):2369-2376.

Dollenmaier et al., Membrane-Associated Respiratory Syncytial Virus F Protein Expressed from a Human Rhinovirus Type 14 Vector is Immunogenic. Virology Mar. 15, 2001;281(2):216-230.

Domenech et al., Rapid clearance of a recombinant *Salmonella* vaccine carrier prevents enhanced antigen-specific CD8 T-cell responses after oral boost immunizations. Microbes and Infection May 2005;7(5-6):860-866.

Donnelly et al., DNA Vaccines. Ann Rev Immunol. 1997;15:617-648.

Donnenberg et al., Rare-Event Analysis of Circulating Human Dendritic Cell Subsets and their Presumptive Mouse Counterparts. Transplantation Dec. 27, 2001;72(12):1946-1951.

Dosaka-Akita et al., Expression of N-Acetylglucosaminyltransferase V is Associated with Prognosis and Histology in Non-Small Cell Lung Cancers. Clin Cancer Res. Mar. 1, 2004;10(5):1773-1779.

Dranoff, GM-CSF-based cancer vaccines. Immunol. Rev. Oct. 2002;188:147-154.

Dussurget et al., Molecular Determinants of Listeria Monocytogenes Virulence. Annu Rev Microbial. 2004;58:587-610.

Duxbury et al., CEACAM6 as a novel target for indirect type 1 immunotoxin-based therapy in pancreatic adenocarcinoma. Biochem Biophys Res Commun. May 7, 2004;317(3):837-843.

Edelman et al., Safety and immunogenicity of recombinant Bacille Calmette-Guerin (rBCG) expressing Borrelia burgdorferi outer surface protein A (OspA) lipoprotein in adult volunteers: a candidate Lyme disease vaccine. Vaccine Feb. 26, 1999;17(7-8):904-914.

Ehrlich et al., Engagement of NKG2D by Cognate Ligand or Antibody Alone is Insufficient to Mediate Costimulation of Human and Mouse CD8+ T Cells. J Immunol. Feb. 15, 2005;174(4):1922-1931.

Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbial. May 1997;35(5):1122-1130.

Emoto et al., Transient Control of Interleukin-4-Producing Natural Killer T Cells in the Livers of Listeria monocytogenes—Infected Mice by Interleukin-12. Infect Immun Dec. 1997;65(12):5003-5009.

Engels et al., Serologic Evidence for Exposure to Simian Virus 40 in North American Zoo Workers. J Infect Dis. Dec. 15, 2004;190(12):2065-2069.

(56) References Cited

OTHER PUBLICATIONS

Enjoji et al., RCAS1, a Useful Serum Marker to Predict the Recurrence of Cancer: Two Cases of Cholangiocarcinoma and Pancreatic Cancer. Dig Dis Sci. Oct. 2004.;49(10):1654-1656.
Erickson et al., Hepatitis C Virus-Specific CTL Responses in the Liver of Chimpanzees with Acute and Chronic Hepatitis C. J Immunol. Oct. 15, 1993;151(8):4189-4199.
Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.
Esslinger, et al., In vivo administration of a lentiviral vaccine targets DCs and induces efficient CD8+ T cell responses. J Clin Invest. Jun. 2003;111(11):1673-1681.
Estcourt et al., DNA vaccines against human immunodeficiency virus type 1. Immunol Rev. Jun. 2004;199:144-155.
Estrada-Franco et al., Venezuelan Equine Encephalitis Virus, Southern Mexico. Emerg Infect Dis. Dec. 2004;10(12):2113-2121.
Excler, Potentials and limitations of protein vaccines in infants. Vaccine Aug.-Sep. 1998;16(14-15):1439-1443.
Fang et al., Expression of Dnmt1, demethylase, MeCP2 and methylation of tumor-related genes in human gastric cancer. World J Gastroenterol. Dec. 1, 2004;10(23):3394-3398.
Faure et al., Inducible Hsp70 as Target of Anticancer Immunotherapy: Identification of HLA-A*0201-Restricted Epitopes. Int J Cancer Mar. 1, 2004;108(6):863-870.
Fensterle et al., Effective DNA Vaccination Against Listeriosis by Prime/Boost Inoculation with the Gene Gun. J Immunol. Oct. 15, 1999;163(8):4510-4518.
Ferraz et al., A Heterologous DNA Priming-*Mycobacterium bovis* BCG Boosting Immunization Strategy Using Mycobacterial Hsp70, Hsp65, and Apa Antigens Improves Protection against Tuberculosis in Mice. Infect Immun. Dec. 2004;72(12):6945-6950.
Ferreira et al., Use of adenoviral vectors as veterinary vaccines. Gene Ther. Oct. 2005;12 Suppl. 1:S73-S83.
Fleischhauer et al., The DAM Gene Family Encodes a New Group of Tumor-specific Antigens Recognized by Human Leukocyte Antigen A2-restricted Cytotoxic T Lymphocytes. Cancer Res. Jul. 15, 1998;58(14):2969-2972.
Fong et al., Altered peptide ligand vaccination with Flt3 ligand expanded dendritic cells for tumor immunotherapy. Proc Natl Acad Sci. USA Jul. 17, 2001;98(15):8809-8814.
Frachon et al., Endothelial cell marker expression in dysplastic lesions of the liver: an immunohistochemical study. J Hepatol. Jun. 2001;34(6):850-857.
Friese et al., MICA/NKG2D-Mediated Immunogene Therapy of Experimental Gliomas. Cancer Res. Dec. 15, 2003;63(24):8996-9006.
Fuessel et al., Multiple tumor marker analyses (PSA, hK2, PSCA, trp-p8) in primary prostate cancers using quantitative RT-PCR. Int J Oncol. Jul. 2003;23(1):221-228.
Gabrilovich, Dendritic cell vaccines for cancer treatment. Curr Opin Mol Ther. Oct. 2002;4(5):452-458.
Gambus et al., Epitope mapping of a mouse monoclonal anti-MUC2 antibody suggests the existence of an immunodominant region in the COOH terminus of the MUC2 tandem-repeat sequence. Int. J. Cancer Jan. 3, 1995;60(1):146-148.
Geiger et al., A generic RNA-pulsed dendritic cell vaccine strategy for renal cell Carcinoma. J Transl Med. Jul. 26, 2005;3:29.
Geisbert and Jahrling, Differentiation of filoviruses by electron microscopy. Virus Res. Dec. 1995;39(2-3):129-150.
Ghazizadeh et al., Role of cdk4, p16INK4, and Rb Expression in the Prognosis of Bronchioloalveolar Carcinomas. Respiration Jan.-Feb. 2005;72(1):68-73.
Gilbert et al., Synergistic DNA-MVA prime-boost vaccination regimes for malaria and tuberculosis. Vaccine May 22, 2006;24(21):4554-4561.
Gilliam et al., A phase II study of G17DT in gastric carcinoma. Eur. J. Surg. Oncol. Jun. 2004;30(5):536-543.
Gilliet and Liu, Generation of Human CD8 T Regulatory Cells by CD40 Ligand-activated Plasmacytoid Dendritic Cells. J Exp Med. Mar. 18, 2002;195(6):695-704.
Goldberg et al., Comparison of Two Cancer Vaccines Targeting Tyrosinase: Plasmid DNA and Recombinant Alphavirus Replicon Particles. Clin. Cancer Res. Nov. 15, 2005; 11(22):8114-8121.
Gonzalez et al., A comparative sequence analysis to revise the current taxonomy of the family Coronaviridae. Arch Virol. Nov. 2003;148(11):2207-2235.
Good et al., Development and regulation of cell-mediated immune responses to the blood stages of malaria: implications for vaccine research. Ann Rev Immunol. 2005;23:69-99.
Good et al., The immunological challenge to developing a vaccine to the blood stages of malaria parasites. Immunol Rev. Oct. 2004;201:254-267.
Gouin et al., Actin-based motility of intracellular pathogens. Curr Opin Microbiol. Feb. 2005;8(1):35-45.
Grangette et al., Protection against tetanus toxin after intragastric administration of two recombinant lactic acid bacteria: impact of strain viability and in vivo persistence. Vaccine Sep. 10, 2002;20(27-28):3304-3309.
Greiner et al., Vaccine-based Therapy Directed against Carcinoembryonic Antigen Demonstrates Antitumor Activity on Spontaneous Intestinal Tumors in the Absence of Autoimmunity. Cancer Res. Dec. 1, 2002; 62(23):6944-6951.
Grimm et al., Mouse alpha-Fetoprotein-Specific DNA-Based Immunotherapy of Hepatocellular Carcinoma Leads to Tumor Regression in Mice. Gastroenterology Oct. 2000;119(4):1104-1112.
Groh et al., Efficient cross-priming of tumor antigen-specific T cells by dendritic cells sensitized with diverse anti-MICA opsonized tumor cells. Proc Natl Acad Sci. USA May 3, 2005;102(18):6461-6466.
Grosenbach et al., Synergy of Vaccine Strategies to Amplify Antigen-specific Immune Responses and Antitumor Effects. Cancer Res. Jun. 1, 2001;61(11):4497-4505.
Gueguen et al., An Antigen Recognized by Autologous CTLs on a Human Bladder Carcinoma. J Immunol. Jun. 15, 1998;160(12):6188-6194.
Gulmann et al., Adenomatous Polyposis *coli* Gene, beta-Catenin, and E-Cadherin Expression in Proximal and Distal Gastric Cancers and Precursor Lesions. Appl Immunohistochem Mol Morphol. Sep. 2003;11(3):230-237.
Gupta et al., Refolding, purification, and crystallization of apical membrane antigen 1 from Plasmodium falciparum. Protein Expr Purif May 2005;41(1):186-198.
Gutierrez et al., Autophagy is a Defense Mechanism Inhibiting BCG and *Mycobacterium tuberculosis* Survival in Infected Macrophages. Cell Dec. 17, 2004;119(6):753-766.
Haddad et al., Novel Antigen Identification Method for Discovery of Protective Malaria Antigens by Rapid Testing of DNA Vaccines Encoding Exons from the Parasite Genome. Infect Immun. Mar. 2004;72(3):1594-1602.
Hakansson et al., Establishment and phenotypic characterization of human U937 cells with inducible P210 BCR/ABL expression reveals upregulation of CEACAM1 (CD66a). Leukemia Mar. 2004;18(3):538-547.
Harris et al., The Biological and Therapeutic Importance of Gastrin Gene Expression in Pancreatic Adenocarcinomas. Cancer Res. Aug. 15, 2004;64(16):5624-5631.
Hashido et al., Evaluation of an enzyme-linked immunosorbent assay based on binding inhibition for type-specific quantification of poliovirus neutralization-relevant antibodies. Microbiol. Immunol. 1999;43(1):73-77.
Hassan et al., Mesothelin: A New Target for Immunotherapy. Clin Cancer Res. Jun. 15, 2004;10(12 Pt 1):3937-3942.
Havlasova et al., Mapping of immunoreactive antigens of Francisella tularensis live vaccine strain. Proteomics Jul. 2002;2(7):857-867.
Weaver et al., Genetic determinants of Venezuelan equine encephalitis emergence. Arch Viral Suppl. 2004;(18):43-64.
Weaver et al., Venezuelan Equine Encephalitis. Annu Rev Entomol. 2004;49:141-174.

(56) References Cited

OTHER PUBLICATIONS

Webster et al., Enhanced T cell-mediated protection against malaria in human challenges by using the recombinant poxviruses FP9 and modified vaccinia virus Ankara. Proc Natl Acad Sci USA Mar. 29, 2005;102(13):4836-4841.

Wells et al., Swine Influenza Virus Infections Transmission From III Pigs to Humans at a Wisconsin Agricultural Fair and Subsequent Probable Person-to-Person Transmission. JAMA. Jan. 23-30, 1991;265(4):478-481.

Wentworth et al., An Influenza A (HINI) Virus, Closely Related to Swine Influenza Virus, Responsible for a Fatal Case of Human Influenza. J Virol. Apr. 1994;68(4):2051-2058.

Williamson et al., Characterization and Selection of HIV-1 Subtype C Isolates for Use in Vaccine Development. AIDS Res Hum Retroviruses Feb. 2003;19(2):133-144.

Wu et al., Construction and Characterization of Adenovirus Serotype 5 Packaged by Serotype 3 Hexon. J Viral. Dec. 2002;76(24):12775-12782.

Xin et al., Prime-boost vaccination with plasmid DNA and a chimeric adenovirus type 5 vector with type 35 fiber induces protective immunity against HIV. Gene Ther. Dec. 2005;12(24):1769-1777.

Xu et al., Immunogenicity of an HIV-1 gag DNA vaccine carried by attenuated Shigella. Vaccine Jan. 30, 2003;21(7-8):644-648.

Yamanaka, Alphavirus vectors for cancer gene therapy (Review). Int J Oncol. Apr. 2004;24(4):919-923.

Yoshimura et al., Selective Targeting of Antitumor Immune Responses with Engineered Live-Attenuated Listeria monocytogenes. Cancer Res. Jan. 15, 2006;66(2):1096-1104.

Zaremba, Identification of an Enhancer Agonist Cytotoxic T Lymphocyte Peptide from Human Carcinoembryonic Antigen. Cancer Res. Oct. 15, 1997;57(20):4570-4577.

Zeier et al., New Ecological Aspects of Hantavirus Infection: A Change of a Paradigm and a Challenge of Prevention—A Review. Virus Genes Mar. 2005;30(2):157-180.

Zhou et al., Development of a Complementing Cell Line and a System for Construction of Adenovirus Vectors with E1 and E2a Deleted. J Virol. Oct. 1996;70(10):7030-7038.

Zhou et al., Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine. Cancer Res. Feb. 1, 2005;65(3):1079-1088.

Zhou et al., Production of helper-dependent adenovirus vector relies on helper virus structure and complementing. J Gene Med. Sep.-Oct. 2002;4(5):498-509.

Zibert et al., Herpes simplex virus type-1 amplicon vectors for vaccine generation in acute lymphoblastic leukemia. Gene Ther. Dec. 2005;12(23):1707-1717.

Zimmerman et al., Expression of annexin II in conventional renal cell carcinoma is correlated with Fuhrman grade and clinical outcome. Virchows Arch. Oct. 2004;445(4):368-374.

Ziyaeyan et al., The Seroprevalence of Parvovirus B19 Infection among To-Be-Married Girls, Pregnant Women, and Their Neonates in Shiraz, Iran. Jpn J Infect Dis. Apr. 2005;58(2):95-97.

Roden and Wu, Preventative and therapeutic vaccines for cervical cancer. Expert Rev Vaccines Aug. 2003;2(4):495-516.

Rodriguez-Pinto and Moreno, B cells can prime naive CD4+ T cells in vivo in the absence of other professional antigen-presenting cells in a CD154-CD40-dependent manner. Eur J Immunol. Apr. 2005;35(4):1097-1105.

Roner et al., Identification of signals required for the insertion of heterologous genome segments into the reovirus genome. Proc Natl Acad Sci USA Dec. 19, 1995;92(26):12362-12366.

Rosenberg et al., Recombinant Fowlpox Viruses Encoding the Anchor-modified gp100 Melanoma Antigen Can Generate Antitumor Immune Responses in Patients with Metastatic Melanoma. Clin Cancer Res. Aug. 1, 2003;9(8):2973-2980.

Rossi and Young, Human Dendritic Cells: Potent Antigen-Presenting Cells at the Crossroads of Innate and Adaptive Immunity. J Immunol. Aug. 1, 2005;175(3):1373-1381.

Saikh et al., Toll-Like Receptor and Cytokine Expression Patterns of CD56+ T Cells are Similar to Natural Killer Cells in Response to Infection with Venezuelan Equine Encephalitis Virus Replicons. J Infect Dis. Nov. 15, 2003;188(10):1562-1570.

Salazar-Onfray et al., Synthetic Peptides Derived from the Melanocyte-stimulating Hormone Receptor MC1R Can Stimulate HLA-A2-restricted Cytotoxic T Lymphocytes That Recognize Naturally Processed Peptides on Human Melanoma Cells. Cancer Res. Oct. 1, 1997;57(19):4348-4355.

Santin et al., The serine protease stratum corneum chymotryptic enzyme (kallikrein 7) is highly overexpressed in squamous cervical cancer cells. Gynecol Oncol. Aug. 2004;94(2):283-288.

Santosuosso et al., Adenoviral Vectors for Mucosal Vaccination Against Infectious Diseases. Viral Immunol. 2005;18(2):283-291.

Sarcevic et al., Expression of Cancer/Testis Tumor Associated Antigens in Cervical Squamous Cell Carcinoma. Oncology 2003;64(4):443-449.

Sarobe et al., Carcinoembryonic antigen as a target to induce anti-tumor immune responses. Curr. Cancer Drug Targets Aug. 2004;4(5):443-454.

Sasaki et al., SAGE mRNA expression in advanced-stage lung cancers. Eur J Surg Oncol. Dec. 2003;29(10):900-903.

Sasatomi et al., Expression of Tumor Rejection Antigens in Colorectal Carcinomas. Cancer Mar. 15, 2002;94(6):1636-1641.

Scanlan et al., Antigens Recognized by Autologous Antibody in Patients with Renal-Cell Carcinoma. Cancer Res. Nov. 12, 1999;83(4):456-464.

Scanlan et al., Cancer-related Serological Recognition of Human Colon Cancer: Identification of Potential Diagnostic and Immunotherapeutic Targets. Cancer Res. Jul. 15, 2002;62(14):4041-4047.

Scanlan et al., Expression of cancer-testis antigens in lung cancer: definition of bromodomain testis-specific gene (BRDT) as a new CT gene, CT9. Cancer Lett. Mar. 31, 2000;150(2):155-164.

Scanlan et al., Humoral immunity to human breast cancer: antigen definition and quantitative analysis of mRNA expression. Cancer Immun. Mar. 30, 2001;1:4 (17 pages).

Scanlan et al., The cancer/testis genes: review, standardization, and commentary. Cancer Immun. Jan. 23, 2004; 4:1 (15 pages).

Scarcella et al., Expression of MAGE and GAGE in High-Grade Brain Tumors: A Potential Target for Specific Immunotherapy and Diagnostic Markers. Clin Cancer Res. Feb. 1999;5(2):335-341.

Schlesinger, Alphavirus vectors: development and potential therapeutic applications. Expert Opin Biol Ther. Mar. 2001;1(2):177-191.

Schluter et al., Immune Reactions to Listeria Monocytogenes in the Brain. Immunobiology Dec. 1999;201(2):188-195.

Schluter et al., Phosphatidylcholine-Specific Phospholipase C from Listeria monocytogenes is an Important Virulence Factor in Murine Cerebral Listeriosis. Infect Immun. Dec. 1998;66(12):5930-5938.

Schmittgen et al., Expression of Prostate Specific Membrane Antigen and Three Alternatively Spliced Variants of PSMA in Prostate Cancer Patients. Int J Cancer Nov. 1, 2003;107(2):323-329.

Schwaab et al., Immunological Effects of Granulocyte-Macrophage Colony-Stimulating Factor and Autologous Tumor Vaccine in Patients with Renal Cell Carcinoma. J Urol. Mar. 2004;171(3):1036-1042.

Schwartz et al. Novel Targeted and Immunotherapeutic Strategies in Chronic Myeloid Leukemia. Semin Hematol. Jan. 2003;40(1):87-96.

Sepehr et al., Distinct pattern of TP53 mutations in squamous cell carcinoma of the esophagus in Iran. Oncogene Nov. 1. 2001;20(50):7368-7374.

Shafferman et al., Alphavirus hybrid virion vaccines. Adv Exp Med Biol. 1996;397:41-47.

Shigemasa et al., Expression of the protease inhibitor antileukoprotease and the serine protease stratum corneum chymotryptic enzyme (SCCE) is coordinated in ovarian tumors. Int J Gynecol Cancer Nov.-Dec. 2001;11(6):454-461.

Shimonishi et al., Precancerous lesions of intrahepatic cholangiocarcinoma. J Hepatobiliary Pancreat Surg. 2000;7(6):542-550.

(56) References Cited

OTHER PUBLICATIONS

Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.
Shirasawa et al., Receptor for advanced glycation end-products is a marker of type I lung alveolar cells. Genes Cells Feb. 2004;9(2):165-174.
Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.
Sibelius et al., Role of Listeria monocytogenes Exotoxins Listeriolysin and Phosphatidylinositol-Specific Phospholipase C in Activation of Human Neutrophils. Infect Immun. Mar. 1999;67(3):1125-1130.
Sidobre et al., The T cell antigen receptor expressed by Valpha14i NKT cells has a unique mode of glycosphingolipid antigen recognition. Proc Natl Acad Sci. Aug. 17, 2004;101(33):12254-12259.
Siegel et al., Induction of antitumour immunity using surviving peptide-pulsed dendritic cells in a murine lymphoma model. Br J Haematol. Sep. 2003;122(6):911-914.
Simon et al., Cervical response to vaccination against HPV16 E7 in case of severe dysplasia. Eur J Obstet Gynecol Reprod Biol. Aug. 15, 2003;109(2):219-223.
Sjolander et al., Serological divergence of Dobrava and Saaremaa hantaviruses: evidence for two distinct serotypes. Epidemiol Infect. Feb. 2002;128(1):99-103.
Skinner et al., Fowlpox virus as a recombinant vaccine vector for use in mammals and poultry. Expert Rev Vaccines Feb. 2005;4(1):63-76.
Slager et al., Identification of Multiple HLA-DR-Restricted Epitopes of the Tumor-Associated Antigen CAMEL by CD4+ Th1/Th2 Lymphocytes. J Immunol. Apr. 15, 2004;172(8):5095-5102.
Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004;11(3):227-236.
Slaghuis et al., Inefficient Replication of Listeria innocua in the Cytosol of Mammalian Cells. J Infect Dis. Feb. 1, 2004;189(3):393-401.
Slansky et al., Enhanced Antigen-Specific Antitumor Immunity with Altered Peptide Ligands that Stabilize the MHC-Peptide-TCR Complex. Immunity Oct. 2000;13(4):529-538.
Small et al., Immunotherapy of Hormone-Refractory Prostate Cancer With Antigen-Loaded Dendritic Cells. J Clin Oncol. Dec. 1, 2000;18(23):3894-3903.
Smith et al., Neutralization of HIV-1 Subtypes: Implications for Vaccine Formulations. J Med Virol. Nov. 1998;56(3):264-268.
Smith et al., Nonstochastic Coexpression of Activation Receptors on Murine Natural Killer Cells. J Exp Med. Apr. 17, 2000;191(8):1341-1354.
Smith et al., Recombinant Modified Vaccinia Ankara Primes Functionally Activated CTL Specific for a Melanoma Tumor Antigen Epitope in Melanoma Patients with a High Risk of Disease Recurrence. Int J Cancer Jan. 10, 2005;113(2):259-266.
Smits et al., Phylogenetic and Evolutionary Relationships among Torovirus Field Variants: Evidence for Multiple Intertypic Recombination Events. J Virol. Sep. 2003;77(17):9567-9577.
Snyder et al., Protection against Lethal Vaccinia Virus Challenge in HLA-A2 Transgenic Mice by Immunization with a Single CD8+ T-Cell Peptide Epitope of Vaccinia and Variola Viruses. J Virol. Jul. 2004;78(13):7052-7060.
Song et al., Characterization of Immune Responses Induced by Intramuscular Vaccination with DNA Vaccines Encoding Measles Virus Hemagglutinin and/or Fusion Proteins. J Virol. Aug. 2005;79(15):9854-9861.
Stambas et al., Long lived multi-isotype anti-HIV antibody responses following a prime-double boost immunization strategy. Vaccine Mar. 31, 2005;23(19):2454-2464.
Havlasova et al., Proteomic analysis of anti-Francisella tularensis LVS antibody response in murine model of tularemia. Proteomics May 2005;5(8):2090-2103.
He et al., Complexes of Poliovirus Serotypes with Their Common Cellular Receptor, CD155. J Virol. Apr. 2003;77(8):4827-4835.
Hellebrand et al., Epstein—Barr virus vector-mediated gene transfer into human B cells: potential for antitumor vaccination. Gene Ther. Jan. 2006;13(2):150-162.
Hertoghs et al., Use of locked nucleic acid oligonucleotides to add functionality to plasmid DNA. Nucleic Acids Res. Oct. 15, 2003;31(20):5817-5830.
Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. Jan. 2005;81(1):48-57.
Hirschowitz et al., Autologous Dendritic Cell Vaccines for Non-Small-Cell Lung Cancer. J Clin Oncol. Jul. 15, 2004;22(14):2808-2815.
Hodge,et al., Diversified prime and boost protocols using recombinant vaccinia virus and recombinant non-replicating avian pox virus to enhance T-cell immunity and antitumor responses. Vaccine Apr.-May 1997;15(6-7):759-768.
Hoffman et al., Strategy for development of a pre-erythrocytic Plasmodium falciparum DNA vaccine for human use. Vaccine Jun. 1997;15(8):842-845.
Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.
Hutchinson et al., Multiplex Analysis of Cytokines in the Blood of Cynomolgus Macaques Naturally Infected With Ebola Virus (Reston Serotype). J Med Virol. Nov. 2001;65(3):561-566.
Hwang and Sanda, Prospects and limitations of recombinant poxviruses for prostate cancer immunotherapy. Curr Opin Mol Ther. Aug. 1999;1(4):471-479.
Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.
International Search Report and Written Opinion issued in PCT/US2007/016290 dated Aug. 26, 2008.
Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.
Isherwood et al., Vaccination strategies for Francisella tularensis. Adv Drug Deliv Rev. Jun. 17. 2005;57(9):1403-1414.
Ito et al., Prostate Carcinoma Detection and Increased Prostate-Specific Antigen Levels after 4 Years in Dutch and Japanese Males Who Had No Evidence of Disease at Initial Screening. Cancer Jan. 15, 2005;103(2):242-250.
Jain et al., Synergistic Effect of a Granulocyte-Macrophage Colony-Stimulating Factor-Transduced Tumor Vaccine and Systemic Interleukin-2 in the Treatment of Murine Colorectal Cancer Hepatic Metastases. Ann Surg Oncol. Aug. 2003;10(7):810-820.
Jainkittivong and Langlais, Herpes B virus infection. Oral Surg Oral Med Oral Pathol Oral Radiol Endod. Apr. 1998;85(4):399-403.
Jamieson et al., Human Torovirus: A New Nosocomial Gastrointestinal Pathogen. J Infect Dis. Nov. 1998;178(5):1263-1269.
Jansen and Shaw, Human Papillomavirus Vaccines and Prevention of Cervical Cancer. Annu Rev Med. 2004;55:319-331.
Janssens and Beyaert, Role of Toll-Like Receptors in Pathogen Recognition. Clinical Microb Revs. Oct. 2003;16(4):637-646.
Jeffery et al., The Preparation and Characterization of Poly(lactide-co-glycolide) Microparticles. II. The Entrapment of a Model Protein Using a (Water-in-Oil)-in-Water Emulsion Solvent Evaporation Technique. Pharm Res. Mar. 1993;10 (3):362-368.
Johansen et al., Technological considerations related to the up-scaling of protein microencapsulation by spray-drying. Eur J Pharm Biopharm. Nov. 2000;50(3):413-417.
Johnson et al., Natural Atypical Listeria innocua Strains with Listeria monocytogenes Pathogenicity Island 1 Genes. Appl Environ Microbiol. Jul. 2004;70(7):4256-4266.

(56) References Cited

OTHER PUBLICATIONS

Johnston et al., Vaccination of macaques with SIV immunogens delivered by Venezuelan equine encephalitis virus replicon particle vectors followed by a mucosal challenge with SIVsmE660. Vaccine Oct. 10, 2005;23(42):4969-4979.
Jung et al., Strategies Against Human Papillomavirus Infection and Cervical Cancer. J Microbiol. Dec. 2004;42(4):255-266.
Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.
Kadowaki et al., Subsets of Human Dendritic Cell Precursors Express Different Toll-like Receptors and Respond to Different Microbial Antigens. J Exp Med. Sep. 17, 2001;194(6):863-869.
Kao et al., Superior efficacy of dendritic cell-tumor fusion vaccine compared with tumor lysate-pulsed dendritic cell vaccine in colon cancer. Immunol Lett. Nov. 15, 2005;101(2):154-159.
Kaufman et al. Targeting the local tumor microenvironment with vaccinia virus expressing B7.1 for the treatment of melanoma. J Clin Invest. Jul. 2005;115(7):1903-1912.
Kaufman et al., Parvovirus B19 does not bind to membrane-associated globoside in vitro. Virology Feb. 5, 2005;332(1):189-198.
Kaufman et al., Phase II Randomized Study of Vaccine Treatment of Advanced Prostate Cancer (E7897): A Trial of the Eastern Cooperative Oncology Group. J Clin Oncol. Jun. 1, 2004;22(11):2122-2132.
Kaufman, Integrating Bench With Bedside: The Role of Vaccine Therapy in the Treatment of Solid Tumors. J Clin Oncol. Feb. 1, 2005;23(4):659-661.
Kedl et al., Comparative Sequence Analysis of the Reovirus S4 Genes from 13 Serotype 1 and Serotype 3 Field Isolates. J Virol. Jan. 1995;69(1):552-559.
Kikuchi et al., Inhibition of Orthotopic Human Bladder Tumor Growth by Lentiviral Gene Transfer of Endostatin. Clin Cancer Res. Mar. 1, 2004;10(5)1835-1842.
Kim et al., Comparison of HPV DNA vaccines employing intracellular targeting strategies. Gene Ther. Jun. 2004;11(12):1011-1018.
Kim et al., DNA Vaccines Employing Intracellular Targeting Strategies and a Strategy to Prolong Dendritic Cell Life Generate a Higher Number of CD8+ Memory T Cells and Better Long-Term Antitumor Effects Compared with a DNA Prime—Vaccinia Boost Regimen. Hum Gen Ther. Jan. 2005;16(1):26-34.
Kim et al., Induction of Therapeutic Antitumor Immunity by In Vivo Administration of a Lentiviral Vaccine. Hum Gene Ther. Nov. 2005;16(11):1255-1266.
Kjaergaard et al., Active immunotherapy for advanced intracranial murine tumors by using dendritic cell-tumor cell fusion vaccines. J Neurosurg. Jul. 2005;103(1):156-164.
Kobayashi et al., Bacterial pathogens modulate an apoptosis differentiation program in human neutrophils. Proc Natl Acad Sci. USA Sep. 16, 2003;100(19):10948-10953.
Koido et al., Assessment of fusion cells from patient-derived ovarian carcinoma cells and dendritic cells as a vaccine for clinical use. Gynecol Oncol. Nov. 2005;99(2):462-471.
Kolb-Maurer et al., Listeria monocytogenes-Infected Human Dendritic Cells: Uptake and Host Cell Response. Infect Immun. Jun. 2000;68(6):3680-3688.
Kotoula et al., Expression of human telomerase reverse transcriptase in regenerative and precancerous lesions of cirrhotic livers. Liver Feb. 2002;22(1):57-69.
Krzych et al., T Lymphocytes from Volunteers Immunized with Irradiated Plasmodium falciparum Sporozoites Recognize Liver and Blood Stage Malaria Antigens. J Immunol. Oct. 15, 1995;155(8):4072-4077.
Kubuschok et al., Expression of Cancer Testis Antigens in Pancreatic Carcinoma Cell Lines, Pancreatic Adenocarcinoma and Chronic Pancreatitis. Int J Cancer. Apr. 20, 2004;109(4):568-575.
Kudo-Saito et al., Intratumoral Vaccination and Diversified Subcutaneous/Intratumoral Vaccination with Recombinant Poxviruses Encoding a Tumor Antigen and Multiple Costimulatory Molecules. Clin Cancer Res. Feb. 1, 2004;10(3):1090-1099.
Kumamuru et al., T-cell receptor Vbeta gene usage by T cells reactive with the tumor-rejection antigen SART-1 in oral squamous cell carcinoma. Int J Cancer Feb. 2004;108(5):686-695.
Kutzler and Weiner, Developing DNA vaccines that call to dendritic cells. J Clin Invest. Nov. 2004;114(9):1241-1244.
Laheru and Jaffee, Immunotherapy for Pancreatic Cancer—Science Driving Clinical Progress. Nat Rev Cancer Jun. 2005;5(6):459-467.
Lalvani et al, Rapid Effector Function in CD8+ Memory T Cells. J Exp Med. Sep. 15, 1997;186(6):859-865.
Muller et al., MeCP2 and MBD2 expression in human neoplastic and non-neoplastic breast tissue and its association with oestrogen receptor status. Br J Cancer Nov. 17, 2003;89(10):1934-1939.
Muminova et al., Characterization of human mesothelin transcripts in ovarian and pancreatic cancer. BMC Cancer May 12, 2004;4:19.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakanuma et al., Anatomic and molecular pathology of intrahepatic Cholangiocarcinoma. J Hepatobiliary Pancreat Surg. 2003;10(4):265-281.
Nakatsura et al., Cellular and humoral immune responses to a human pancreatic cancer antigen, coactosin-like protein, originally defined by the SEREX method. Eur J Immunol. Mar. 2002;32(3):826-836.
Nakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.
Neumann et al., Identification of an HLA-DR-Restricted Peptide Epitope with a Promiscuous Binding Pattern Derived from the Cancer Testis Antigen HOM-MEL-40/SSX2. Int J Cancer Nov. 20, 2004;112(4):661-668.
Nicoletto et al., BRCA-1 and BRCA-2 mutations as prognostic factors in clinical practice and genetic counseling. Cancer Treat Rev. Oct. 2001; 27(5):295-304.
Nishitani et al., Cytokine Gene Therapy for Cancer with Naked DNA. Mol Urol. 2000 Summer;4(2):47-50.
Oberste et al., Evidence for Frequent Recombination within Species Human Enterovirus B Based on Complete Genomic Sequences of All Thirty-Seven Serotypes. J Virol. Jan. 2004;78(2):855-867.
Oberthuer et al., The Tumor-Associated Antigen PRAME is Universally Expressed in High-Stage Neuroblastoma and Associated with Poor Outcome. Clin Cancer Res. Jul. 1, 2004;10(13):4307-4313.
O'Hagan et al., Biodegradable microparticles for oral immunization. Vaccine 1993;11(2):149-154.
Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.
O'Neill et al., Manipulating dendritic cell biology for the active immunotherapy of cancer. Blood Oct. 15, 2004;104(8):2235-2246.
Orvell et al., Antigenic relationships between six genotypes of the small hydrophobic protein gene of mumps virus. J Gen Virol. Oct. 2002;83(Pt 10):2489-2496.
Osada et al., NK cell activation by dendritic cell vaccine: a mechanism of action for clinical activity. Cancer Immunol Immunother. Sep. 2006;55(9):1122-1131.
Otte et al., MAGE—A Gene Expression Pattern in Primary Breast Cancer. Cancer Res. Sep. 15, 2001;61(18):6682-6687.
Overwijk et al., gp100/pmel 17 is a Murine Tumor Rejection Antigen: Induction of "Self"-reactive, Tumoricidal T Cells Using High-affinity, Altered Peptide Ligand. J Exp Med. Jul. 20, 1998;188(2):277-286.
Oyston and Quarry, Tularemia vaccine: past, present and future. Antonie Van Leeuwenhoek May 2005;87(4):277-281.

(56) References Cited

OTHER PUBLICATIONS

Padilla et al., Imaging of the varicella zoster virion in the viral highways: comparison with herpes simplex viruses 1 and 2, cytomegalovirus, pseudorabies virus, and human herpes viruses 6 and 7. J Med Virol. 2003;70 (Suppl. I)S103-S110.
Paessler et al., Recombinant Sindbis/Venezuelan Equine Encephalitis Virus is Highly Attenuated and Immunogenic. J Virol. Sep. 2003;77(17):9278-9286.
Pal et al., Immunization of rhesus macaques with a polyvalent DNA prime/protein boost human immunodeficiency virus type 1 vaccine elicits protective antibody response against simian human immunodeficiency virus of R5 phenotype. Virology May 10, 2006;348(2):341-353.
Palmowski et al., Competition Between CTL Narrows the Immune Response Induced by Prime-Boost Vaccination Protocols. J Immunol. May 1, 2002;168(9):4391-4398.
Pan et al., Modulation of disease, T cell responses, and measles virus clearance in monkeys vaccinated with H-encoding alphavirus replicon particles. Proc Natl Acad Sci. USA Aug. 16, 2005;102:11581-11588.
Paoletti, Applications of pox virus vectors to vaccination: An update. Proc Natl Acad Sci. USA Oct. 15, 1996;93(21):11349-11353.
Parmiani et al., Cancer Immunotherapy With Peptide-Based Vaccines: What Have We Achieved? Where are We Going? J Natl Cancer Inst. Jun. 5, 2002;94(11):805-818.
Pasetti et al., Attenuated *Salmonella enterica* Serovar Typhi and Shigella flexneri 2a Strains Mucosally Deliver DNA Vaccines Encoding Measles Virus Hemagglutinin, Inducing Specific Immune Responses and Protection in Cotton Rats. J Virol. May 2003;77(9):5209-5219.
Patel et al., Development of a simple restriction fragment length polymorphism assay for subtyping of coxsackie B viruses. J Virol Methods Sep. 15, 2004;120(2):167-172.
Peacock et al., Gender Differences in Human Immunodeficiency Virus Type 1-Specific CD8 Responses in the Reproductive Tract and Colon following Nasal Peptide Priming and Modified Vaccinia Virus Ankara Boosting. J Virol. Dec. 2004;78(23):13163-13172.
Peh et al., Frequent presence of subtype A virus in Epstein-Barr virus-associated malignancies. Pathology Oct. 2002;34(5):446-450.
Pellinen et al., Cancer cells as targets for lentivirus-mediated gene transfer and gene therapy. Int J Oncol. Dec. 2004;25(6):1753-1762.
Penna et al., Cutting Edge: Differential Chemokine Production by Myeloid and Plasmacytoid Dendritic Cells. J Immunol. Dec. 15, 2002;69(12):6673-6676.
Peritt et al., Cutting Edge: Differentiation of Human NK Cells into NK1 and NK2 Subsets. J Immunol. Dec. 1, 1998;161(11):5821-5824.
Perri et al., An Alphavirus Replicon Particle Chimera Derived from Venezuelan Equine Encephalitis and Sindbis Viruses is a Potent Gene-Based Vaccine Delivery Vector. J Virol. Oct. 2003;77(19):10394-10403.
Pisarev et al., Full-Length Dominant-Negative Survivin for Cancer Immunotherapy. Clin Cancer Res. Dec. 15, 2003;9(17):6523-6533.
Polo and Dubensky, Virus-based vectors for human vaccine applications. Drug Discov Today Jul. 1, 2002;7(13):719-727.
Polo et al., Stable alphavirus packaging cell lines for Sindbis virus-and Semliki Forest virus-derived vectors. Proc Natl Acad Sci. USA Apr. 13, 1999;96(8):4598-4603.
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.
Portnoy et al., The cell biology of Listeria monocytogenes infection: the intersection of bacterial pathogenesis and cell-mediated immunity. J Cell Biol. Aug. 5, 2002;158(3):409-414.
Prud'Homme, DNA vaccination against tumors. J Gene Med. Jan. 2005;7(1):3-17.

Quinnan et al., Protection of Rhesus Monkeys against Infection with Minimally Pathogenic Simian-Human Immunodeficiency Virus: Correlations with Neutralizing Antibodies and Cytotoxic T Cells. J Virol. Mar. 2005;79(6):3358-3369.
Ranasinghe et al., Evaluation of fowlpox-vaccinia virus prime-boost vaccine strategies for high-level mucosal and systemic immunity against HIV-1. Vaccine Jul. 26, 2006;24(31-32):5881-5895.
Rasmussen et al., DNA prime/protein boost immunization against HIV clade C: Safety and immunogenicity in mice. Vaccine Mar. 20, 2006;24(13):2324-2332.
Renkvist et al., A listing of human tumor antigens recognized by T cells. Cancer Immunol Immunother. Mar. 2001;50(1):3-15.
Reynolds et al., HLA-Independent Heterogeneity of CD81 T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Rezig et al., Molecular Characterization of Coxsackievirus B5 Isolates. J Med Virol. Feb. 2004;72(2):268-274.
Ries et al., Investigation of the expression of melanoma antigen-encoding genes (MAGE-A1 to-A6) in oral squamous cell carcinomas to determine potential targets for gene-based cancer immunotherapy. Int J Oncol. Mar. 2005;26(3):817-824.
Roberts et al., Hexon-chimaeric adenovirus serotype 5 vectors circumvent pre-existing anti-vector immunity. Nature May 11, 2006;441(7090):239-243.
Rocken and Carl-McGrath, Pathology and Pathogenesis of Hepatocellular Carcinoma. Dig Dis. 2001;19(4):269-278.
Abutaily et al., Cadherins, catenins and APC in pleural malignant mesothelioma. J Pathol. Nov. 2003;201(3):355-362.
Aguilar et al., Endemic Venezuelan Equine Encephalitis in Northern Peru. Emerg Infect Dis. 2004;10:880-888.
Ahn et al., All CVB Serotypes and Clinical Isolates Induce Irreversible Cytopathic Effects in Primary Cardiomyocytes. J Med Virol. Feb. 2005;75(2):290-294.
Alferink, et al., Compartmentalized Production of CCL17 In Vivo: Strong Inducibility in Peripheral Dendritic Cells Contrasts Selective Absence from the Spleen. J Exp Med. 2003;197:585-599.
Altwein and Luboldt, Prognostic factors for carcinoma of the prostate. Urol Int. 1999;63(1):62-71.
Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.
Andersen and Straten, Survivin—a universal tumor antigen. Histol Histopathol. Apr. 2002;17(2):669-675.
Anthony, Precursor Lesions for Liver Cancer in Humans. Cancer Res. Jul. 1976;36(7 Pt 2):2579-2583.
Argani et al., Discovery of New Markers of Cancer through Serial Analysis of Gene Expression: Prostate Stem Cell Antigen is Overexpressed in Pancreatic Adenocarcinoma1. Cancer Res. 2001;61:4320-4324.
Arlen et al. Pox viral vaccine approaches. Semin Oncol. Dec. 2005;32(6):549-555.
Arlen et al., Strategies for the development of PSA-based vaccines for the treatment of advanced prostate cancer. Expert Rev Vaccines Aug. 2003;2(4):483-493.
Arnold et al., Chimeric rhinoviruses as tools for vaccine development and characterization of protein epitopes. Intervirology 1996;39(1-2):72-78.
Arora et al., Identification of Differentially Expressed Genes in Oral Squamous Cell Carcinoma. Mol Carcinog. Feb. 2005;42(2):97-108.
Arpinati et al., Granulocyte-colony stimulating factor mobilizes T helper 2-inducing dendritic cells. Blood Apr. 15, 2000;95(18)1484-2490.
Atkins et al., Alphaviruses and their derived vectors as anti-tumor agents. Curr Cancer Drug Targets Nov. 2004;4(7):597-607.
Attoui et al., Comparative sequence analysis of American, European and Asian isolates of viruses in the genus Coltivirus. J Gen Virol. Oct. 1998;79(Pt 10):2481-2489.

(56) References Cited

OTHER PUBLICATIONS

Auerbuch et al., Development of a Competitive Index Assay to Evaluate the Virulence of Listeria monocytogenes actA Mutants during Primary and Secondary Infection of Mice. Infect Immun. Sep. 2001;69(9):5953-5957.

Badovinac et al., Accelerated CD8+ T-cell memory and prime-boost response after dendritic-cell vaccination. Nat Med. Jul. 2005;11(7):748-756.

Badovinac et al., Programmed contraction of CDS+ T cells after infection. Nat Immunol. Jul. 2002;3(7):619-626.

Baez-Astua et al., Low-Dose Adenovirus Vaccine Encoding Chimeric Hepatitis B Virus Surface Antigen-Human Papillomavirus Type 16 E7 Proteins Induces Enhanced E7-Specific Antibody and Cytotoxic T-Cell Responses. J Virol. Oct. 2005;79(20):12807-12817.

Balasuriya et al., Expression of the Two Major Envelope Proteins of Equine Arteritis Virus as a Heterodimer is Necessary for Induction of Neutralizing Antibodies in Mice Immunized with Recombinant Venezuelan Equine Encephalitis Virus Replicon Particles. J Virol. Nov. 2000;74(22):10623-10630.

Baldwin et al., Vaccinia-Expressed Human Papillomavirus 16 and 18 E6 and E7 as a Therapeutic Vaccination for Vulval and Vaginal Intraepithelial Neoplasia. Clin Cancer Res. Nov. 1, 2003;9(14):5205-5213.

Banchereau and Palucka, Dendritic Cells as Therapeutic Vaccines Against Cancer. Nat Rev Immunol. Apr. 2005;5(4):296-306.

Barbanti-Brodano et al., Simian virus 40 infection in humans and association with human diseases: results and hypotheses. Virology Jan. 5, 2004;318(1):1-9.

Barthold et al., Infectivity, disease patterns, and serologic profiles of reovirus serotypes 1, 2, and 3 in infant and weanling mice. Lab Anim Sci. Oct. 1993;43(5):425-430.

Bauer et al., Bacterial CpG-DNA Triggers Activation and Maturation of Human CD11c2, CD1231 Dendritic Cells. J Immunol. 2001;166:5000-5007.

Baurain et al., High Frequency of Autologous Anti-Melanoma CTL Directed Against an Antigen Generated by a Point Mutation in a New Helicase Gene. J Immunol. Jun. 1, 2000;164(11):6057-6066.

Becker, Immunological and Regulatory Functions of Uninfected and Virus Infected Immature and Mature Subtypes of Dendritic Cells—a Review. Virus Genes 2003;26(2):119-130.

Benvegnu et al., Space-occupying lesions of the liver detected by ultrasonography and their relation tohepatocellular carcinoma in cirrhosis. Liver Apr. 1992;12(2):80-83.

Bevanger et al., Competitive Enzyme Immunoassay for Antibodies to a 43,000-Molecular-Weight Francisella tularensis Outer Membrane Protein for the Diagnosis of Tularemia. J Clin Microbiol. May 1989;27(5):922-926.

Bhigjee et al., Sequence of the env Gene of Some KwaZulu-Natal, South African Strains of HTLV Type I. AIDS Res Hum Restrovirus 1999 ;15:1229-1233.

Biagini et al., Simultaneous measurement of specific serum IgG responses to five select agents. Anal Bioanal Chem. Jun. 2005;382(4):1027-1034.

Bondurant et al., Definition of an Immunogenic Region Within the Ovarian Tumor Antigen Stratum Corneum Chymotryptic Enzyme. Clin Cancer Res. May 1, 2005;11(9):3446-3454.

Boonstra et al., Flexibility of Mouse Classical and Plasmacytoid-derived Dendritic Cells in Directing T Helper Type 1 and 2 Cell Development: Dependency on Antigen Dose and Differential Toll-like Receptor Ligation. J Exp Med. Jan. 6, 2003;197(1):101-109.

Borrello and Pardoll, GM-CSF-based cellular vaccines: a review of the clinical experience. Cytokine Growth Factor Rev. Apr. 2002;13(2):185-193.

Boyer et al., DNA prime Listeria boost induces a cellular immune response to SIV antigens in the rhesus macaque model that is capable of limited suppression of SIV239 viral replication. Virology Mar. 1, 2005;333(1):88-101.

Brezniceanu et al., HMGB1 inhibits cell death in yeast and mammalian cells and is abundantly expressed in human breast carcinoma. FASEB J. Jul. 2003;17(10):1295-1297.

Brian and Baric, Coronavirus genome structure and replication. Cuff Top Microbial Immunol. 2005;287:1-30.

Brinkmann et al., Novel Genes in the PAGE and GAGE Family of Tumor Antigens Found by Homology Walking in the dbEST Database. Cancer Res. Apr. 1, 1999;59(7):1445-1448.

Briones et al., In Vivo Antitumor Effect of CD40L-transduced Tumor Cells as a Vaccine forB-Cell Lymphoma. Cancer Res. Jun. 1, 2002;62(11):3195-3199.

Brockstedt et al., Killed but metabolically active microbes: a new vaccine paradigm for eliciting effector T-cell responses and protective immunity. Nat Med. Aug. 2005;11(8):853-860.

Brockstedt et al., Listeria-based cancer vaccines that segregate immunogenicity from toxicity. Proc Natl Acad Sci. USA Sep. 21, 2004;101(38):13832-13837.

Bronte et al., Genetic Vaccination with "Self" Tyrosinase-related Protein 2 Causes Melanoma Eradication but not Vitiligo. Cancer Res. Jan. 15, 2000; 60(2):253-258.

Brown et al., Complete Genomic Sequencing Shows that Polioviruses and Members of Human Enterovirus Species C are Closely Related in the Noncapsid Coding Region. J Virol. Aug. 2003;77(16):8973-8984.

Brown, Variants of B19. Dev Biol (Basel) 2004;118:71-77.

Brzoza et al., Cytoplasmic Entry of Listeria monocytogenes Enhances Dendritic Cell Maturation and T Cell Differentiation and Function. J Immunol. Aug. 15, 2004;173(4):2641-2651.

Byrd et al., Biological consequences of antigen and cytokine co-expression by recombinant *Streptococcus gordonii* vaccine vectors. Vaccine May 22, 2002;20(17-18):2197-2205.

Capdepont et al., New Insights in HTLV-I Phylogeny by Sequencing and Analyzing the Entire Envelope Gene. AIDS Res Hum Retrovirus Jan. 2005;21(1):28-42.

Capurro et al., Glypican-3: A Novel Serum and Histochemical Marker for Hepatocellular Carcinoma. Gasteroenterol. Jul. 2003;125(1):89-97.

Carbone et al., New developments about the association of SV40 with human mesothelioma. Oncogene Aug. 11, 2003;22(33):5173-5180.

Lasaro et al., Prime-boost vaccine regimen confers protective immunity to human-derived enterotoxigenic *Escherichia coli*. Vaccine Mar. 31, 2005;23(19):2430-2438.

Lauterbach et al., Reduced immune responses after vaccination with a recombinant herpes simplex virus type 1 vector in the presence of antiviral immunity. J Gen Virol. Sep. 2005;86(Pt 9):2401-2410.

Lecuit and Cossart, Genetically-modified-animal models for human infections: the Listeria paradigm. Trends Mol Med. Nov. 2002;8(11):537-542.

Lecuit et al., Targeting and crossing of the human maternofetal barrier by Listeria monocytogenes: Role of internalin interaction with trophoblast E-cadherin. Proc Natl Acad Sci. USA Apr. 20, 2004;101(16):6152-6157.

Lee et al., Immunomic analysis of human sarcoma. Proc Natl Acad Sci. USA Mar. 4, 2003;100(5):2651-2656.

Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.

Li et al., Expression Profile of Cancer-Testis Genes in 121 Human Colorectal Cancer Tissue and Adjacent Normal Tissue. Clin Cancer Res. Mar. 1, 2005;11(5):1809-1814.

Liang et al., Microvessel density, cyclo-oxygenase 2 expression, K-ras mutation and p53 overexpression in colonic cancer. Br J Surg. Mar. 2004;91(3):355-361.

Liao et al., Fusion Protein Vaccine by Domains of Bacterial Exotoxin Linked with a Tumor Antigen Generates Potent Immunologic Responses and Antitumor Effects. Cancer Res. Oct. 1, 2005;65(19):9089-9098.

Lim et al., Molecular and phenotypic spectrum of de novo Philadelphia positive acute leukemia. Int. J. Mol. Med. Dec. 1999;4(6):665-667.

(56) References Cited

OTHER PUBLICATIONS

Lin et al. Melanoma-Associated Antigens in Esophageal Adenocarcinoma: Identification of Novel MAGE-A10 Splice Variants. Clin Cancer Res. 2004;10:5708-5716.

Lin et al., Boosting with Recombinant Vaccinia Increases HPV-16 E7-Specific T Cell Precursor Frequencies and Antitumor Effects of HPV-16 E7-Expressing Sindbis Virus Replicon Particles. Mol Ther. Oct. 2003;8(4):559-566.

Liu et al., Enhanced immune response by amphotericin B following NS1 protein prime-oral recombinant Salmonella vaccine boost vaccination protects mice from dengue virus challenge. Vaccine Jul. 26, 2006;24(31-32):5852-5861.

Liu, Uncover the Mystery of Plasmacytoid Dendritic Cell Precursors or Type 1 Interferon Producing Cells by Serendipity. Hum Immunol. Dec. 2002;63(12):1067-1071.

Loessner and Weiss, Bacteria-mediated DNA transfer in gene therapy and vaccination. Expert Opin Biol Ther. Feb. 2004;4(2):157-168.

Loparev et al., Global Identification of Three Major Genotypes of Varicella-Zoster Virus: Longitudinal Clustering and Strategies for Genotyping. J Virol. Aug. 2004;78(15):8349-8358.

Lucas et al., MAGE-B5, MAGE-B6, MAGE-C2, and MAGE-C3: Four New Members of the MAGE Family with Tumor-Specific Expression. Int J Cancer Jul. 1, 2000;87(1):55-60.

Luijkx et al., Heterologous prime-boost strategy to overcome weak immunogenicity of two serosubtypes in hexavalent Neisseria meningitidis outer membrane vesicle vaccine. Vaccine Mar. 6, 2006;24(10):1569-1577.

Lundstrom, Alphavirus vectors for vaccine production and gene therapy. Expert Rev Vaccines Jun. 2003;2(3):447-459.

Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.

Mackova et al., Prime/boost immunotherapy of HPV16-induced tumors with E7 protein delivered by Bordetella adenylate cyclase and modified vaccinia virus Ankara. Cancer Immunol Immunother. Jan. 2006;55(1):39-46.

Malowany et al., Development of Cell-Based Tuberculosis Vaccines: Genetically Modified Dendritic Cell Vaccine is a Much More Potent Activator of CD4 and CD8 T Cells Than Peptide- or Protein-Loaded Counterparts. Mol Ther. Apr. 2006;13(4):766-775.

Mandruzzato et al., A CASP-8 Mutation Recognized by Cytolytic T Lymphocytes on a Human Head and Neck Carcinoma. J Exp Med. Aug. 29, 1997;186(5):785-793.

Manohar et al., Gut Colonization of Mice with actA-Negative Mutant of Listeria monocytogenes Can Stimulate a Humoral Mucosal Immune Response. Infect Immun. Jun. 2001;69(6):3542-3549.

Marshall et al., Phase I Study of Sequential Vaccinations With Fowlpox-CEA(6D)-TRICOM Alone and Sequentially With Vaccinia-CEA(6D)-TRICOM, With and Without Granulocyte-Macrophage Colony-Stimulating Factor, in Patients With Carcinoembryonic Antigen-Expressing Carcinomas. J Clin Oncol. Feb. 2005 123:720-731.

Mascola, Vaccines: Engineering immune evasion. Nature May 11, 2006;441(7090):161-162.

Matsumoto et al., Expression of the SART-1 Antigens in Uterine Cancers. Jpn J Cancer Res. Dec. 1998;89(12):1292-1295.

Matsushita et al., Preferentially Expressed Antigen of Melanoma (PRAME) in the Development of Diagnostic and Therapeutic Methods for Hematological Malignancies. Leuk Lymphoma Mar. 2003;44(3):439-444.

Mayo et al., Mdm-2 Phosphorylation by DNA-dependent Protein Kinase Prevents Interaction with p53. Cancer Res. Nov. 15, 1997;57(22):5013-5016.

McCabe et al., Minimal Determinant Expressed by a Recombinant Vaccinia Virus Elicits Therapeutic Antitumor Cytolytic T Lymphocyte Responses. Cancer Res. Apr. 15, 1995;55(8):1741-1747.

McCool et al., Roles of calreticulin and calnexin during mucin synthesis in LS180 and HT29/A1 human colonic adenocarcinoma cells. Biochem J. Aug. 1, 1999;341(Pt 3):593-600.

McGee et al., the encapsulation of a model protein in poly (D, L lactide-co-glycolide) microparticles of various sizes: an evaluation of process reproducibility. J Microencapsul. Mar.-Apr. 1997;14(2):197-210.

McHeyzer-Williams et al., Enumeration and Characterization of Memory Cells in the TH Compartment. Immunol Rev. Apr. 1996;150:5-21.

McKenna et al., Plasmacytoid Dendritic Cells: Linking Innate and Adaptive Immunity. J Virol. Jan. 2005;79(1):17-27.

McMichael and O'Callaghan, A New Look at T Cells. J Exp Med. May 4, 1998;187(9)1367-1371.

Meyer et al., A phase I vaccination study with tyrosinase in patients with stage II melanoma using recombinant modified vaccinia virus Ankara (MVA-hTyr). Cancer Immunol Immunother. May 2005;54(5):453-467.

Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.

Milohanic et al., Transcriptome analysis of Listeria monocytogenes identifies three groups of genes differently regulated by PrfA. Mol Microbiol. Mar. 2003;47(6):1613-1625.

Mincheff et al., In vivo transfection and/or cross-priming of dendritic cells following DNA and adenoviral immunizations for immunotherapy of cancer—changes in peripheral mononuclear subsets and intracellular IL-4 and IFN-gamma lymphokine profile. Crit Rev Oncol Hematol. Jul.-Aug. 2001;39(1-2):125-132.

Minev et al., Insertion Signal Sequence Fused to Minimal Peptides Elicits Specific CD8+ T-Cell Responses and Prolongs Survival of Thymoma-bearing Mice. Cancer Res. Aug. 1, 1994;54(15):4155-4161.

Molijn et al., Molecular diagnosis of human papillomavirus (HPV) infections. J Clin Virol. Mar. 2005;32 Suppl. 1:S43-S51.

Moreau-Aubry et al., A Processed Pseudogene Codes for a New Antigen Recognized by a CD8+ T Cell Clone on Melanoma. J Exp Med. May 1, 2000;191(9):1617-1624.

Morenweiser, Downstream processing of viral vectors and vaccines. Gene Ther. Oct. 2005;12 Suppl. 1: SI03-S110.

Morse and Lyerly, Dendritic cell-based approaches to cancer immunotherapy. Expert Opin Investig Drugs Oct. 1998;7(10):1617-1627.

Morse and Lyerly, DNA and RNA Modified Dendritic Cell Vaccines. World J Surg. Jul. 2002; 26(7):819-825.

Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. Jun. 1999;5(6):1331-1338.

Morse et al., CEA loaded dendritic cell vaccines. Cancer Chemother Biol Response Modif. 2002;20:385-390.

Morse et al., HER2 dendritic cell vaccines. Clin Breast Cancer Feb. 2003;3 Suppl.4:S164-S172.

Mukhopadhyay et al., A Structural Perspective of the Flavivirus Life Cycle. Nat Rev Microbiol. Jan. 2005;3(1):13-22.

Mulders et al., Tumor antigens and markers in renal cell carcinoma. Urol Clin North Am. Aug. 2003;30(3):455-465.

Stams et al., Expression Levels of TEL, AML1, and the Fusion Products TEL-AML1 and AML1-TEL versus Drug Sensitivity and Clinical Outcome in t(12;21)—Positive Pediatric Acute Lymphoblastic Leukemia. Clin Cancer Res. Apr. 15, 2005;11(8):2974-2980.

Steffens et al., Immunohistochemical analysis of tumor antigen saturation following injection of monoclonal antibody G250. Anticancer Res. Mar.-Apr. 1999,19(2A):1197-1200.

Stirnadel et al., Assessment of different sources of variation in the antibody responses to specific malaria antigens in children in Papua New Guinea. Int J Epidemiol. Jun. 2000;29(3):579-586.

(56) References Cited

OTHER PUBLICATIONS

Stolier et al., Initial Experience with Surgical Treatment Planning in the Newly Diagnosed Breast Cancer Patient at High Risk for BRCA-1 or BRCA-2 Mutation. Breast J. Nov.-Dec. 2004;10(6):475-480.
Strugnell et al., DNA vaccines for bacterial infections. Immunol Cell Biol. Aug. 1997;75(4):364-369.
Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.
Su and Bannasch, Relevance of Hepatic Preneoplasia for Human Hepatocarcinogenesis. Toxicol Pathol. Jan.-Feb. 2003:31(1):126-133.
Sugauchi et al., Vigorous Hepatitis C Virus-Specific CD4+ and CD8+ T Cell Responses Induced by Protein Immunization in the Presence of Montanide ISA720 plus Synthetic Oligodeoxynucleotides Containing Immunostimulatory Cytosine-Guanine Dinucleotide Motifs. J Infect Dis. Feb. 15, 2006;193(4):563-572.
Sumida et al., Recruitment and expansion of dendritic cells in vivo potentiate the immunogenicity of plasmid DNA vaccines. J Clin Invest. Nov. 2004;114(9):1334-1342.
Sunderkotter et al., Subpopulations of Mouse Blood Monocytes Differ in Maturation Stage and Inflammatory Response. J Immunol. Apr. 1, 2004;172(7):4410-4417.
Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.
Tai et al., Curative Potential of GM-CSF-Secreting Tumor Cell Vaccines on Established Orthotopic Liver Tumors: Mechanisms for the Superior Antitumor Activity of Live Tumor Cell Vaccines. J Biomed Sci. Mar.-Apr. 2004,11(2):228-238.
Takahashi et al., 707-AP Peptide Recognized by Human Antibody Induces Human Leukocyte Antigen A2-restricted Cytotoxic T Lymphocyte Killing of Melanoma. Clin Cancer Res. Aug. 1997;3(8):1363-1370.
Takayama and Takayama, New method of differentiating wild-type varicella-zoster virus (VZV) strains from Oka varicella vaccine strain by VZV ORF 6-based PCR and restriction fragment length polymorphism analysis. J Clin Virol. Feb. 2004;29(2):113-119.
Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.
Tanaka et al., Expression of Tumor-rejection Antigens in Gynecologic Cancers. Jpn J Cancer Res. Nov. 2000;91(11)1177-1184.
Taniguchi et al., The Regulatory Role of Valpha14 NKT Cells in Innate and Acquired Immune Response. Annu Rev Immunol. 2003;21:483-513.
Tannapfel et al., BRAF Gene Mutations are Rare Events in Gastroenteropancreatic Neuroendocrine Tumors. Am J Clin Pathol. Feb. 2005;123(2):256-260.
Tatsis and Ertl, Adenoviruses as Vaccine Vectors. Mol Ther. Oct. 2004;10(4):616-629.
Thiry et al., Recombination in the alphaherpesvirus bovine herpesvirus 1. Vet Microbiol. Mar. 31, 2006;113(3-4):171-177.
Thomas et al., Enhanced Tumor Protection by Granulocyte-Macrophage Colony-Stimulating Factor Expression at the Site of an Allogeneic Vaccine. Human Gene Ther. Apr. 10, 1998;9(6):835-843.
Tobery et al., A simple and efficient method for the monitoring of antigen-specific T cell responses using peptide pool arrays in a modified ELISpot assay. J Immunol Methods. Aug. 1, 2001;254(1-2):59-66.
Torres et al., Toll-Like Receptor 2 is Required for Optimal Control of Listeria monocytogenes Infection. Infect Immun. Apr. 2004;72(4):2131-2139.
Toussaint et al., Prime-boost strategies combining DNA and inactivated vaccines confer high immunity and protection in cattle against bovine herpesvirus-1. Vaccine Oct. 17, 2005;23(43):5073-5081.
Trapp et al., Potential of Equine Herpesvirus 1 as a Vector for Immunization. J Virol. May 2005;79(9):5445-5454.
Treurnicht et al., HHV-8 Subtypes in South Africa: Identification of a Case Suggesting a Novel B Variant. J Med Virol. Feb. 2002;66(2):235-240.
Trimble et al., Comparison of the CD8+ T cell responses and antitumor effects generated by DNA vaccine administered through gene gun, biojector, and syringe. Vaccine Sep. 8, 2003;21(25-26):4036-4042.
Trincado et al., Human Cytomegalovirus Strains Associated With Congenital and Perinatal Infections. J Med Virol. Aug. 2000;61(4):481-487.
Tsang et al., Phenotypic Stability of a Cytotoxic T-Cell Line Directed against an Immunodominant Epitope of Human Carcinoembryonic Antigen. Clin Cancer Res. Dec. 1997;3(12 Pt 1):2439-2449.
Tsao and Sober, Melanoma treatment update. Dermatol Clin. Apr. 2005;23(2):323-333.
Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).
Tuting, The immunology of cutaneous DNA immunization. Curr Opin Mol Ther. Apr. 1999:1(2):216-225.
Tvinnereim et al., Neutrophil Involvement in Cross-Priming CD8+ T Cell Responses to Bacterial Antigens. J Immunol. Aug. 1, 2004;173(3):1994-2002.
Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and HTLV-IIb Subtypes. J Acquir Immune Defic Syndr Hum Retrovirol. Dec. 1, 1996;13(4):384-391.
Van Den Eynde et al., A New Antigen Recognized by Cytolytic T Lymphocytes on a Human Kidney Tumor Results from Reverse Strand Transcription. J Exp Med. Dec. 20, 1999;190(12):1793-1800.
Vandamme et al., African Origin of Human T-Lymphotropic Virus Type 2 (HTLV-2) Supported by a Potential New HTLV-2d Subtype in Congolese Bambuti Efe Pygmies. J Viral. May 1998;72(5):4327-4340.
Vanniasinkam and Ertl, Adenoviral gene delivery for HIV-1 vaccination. Curr Gene Ther. Apr. 2005;5(2):203-212.
Vasir et al., Fusion of dendritic cells with multiple myeloma cells results in maturation and enhanced antigen presentation. Br J Haematol. Jun. 2005;129(5):687-700.
Vazquez-Boland et al., Listeria Pathogenesis and Molecular Virulence Determinants. Clin Microbiol Rev. Jul. 2001;14(3):584-640.
Vieweg and Dannull, Tumor vaccines: from gene therapy to dendritic cells—the emerging frontier. Urol Clin North Am. Aug. 2003;30(3):633-643.
Vilas et al., Cytomegalovirus Glycoprotein B Genotypes and Central Nervous System Disease in AIDS Patients. J Med Virol. Nov. 2003;71(3):404-407.
Vilchez and Butel, Emergent Human Pathogen Simian Virus 40 and Its Role in Cancer. Clin Microbiol Rev. Jul. 2004;17(3):495-508.
Vindurampulle et al., Recombinant *Salmonella enterica* serovar Typhi in a prime-boost strategy. Vaccine Sep. 9, 2004;22(27-28):3744-3750.
Virok et al., Chlamydial Infection Induces Pathobiotype-Specific Protein Tyrosine Phosphorylation in Epithelial Cells. Infect Immun. Apr. 2005;73(4):1939-1946.
Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.

(56) References Cited

OTHER PUBLICATIONS

Waltregny et al, Screening of histone deacetylases (HDAC) expression in human prostate cancer reveals distinct class I HDAC profiles between epithelial and stromal cells. Eur J Histochem. Jul.-Sep. 2004;48(3):273-290.

Walzer et al., Differential In Vivo Persistence of Two Subsets of Memory Phenotype CD8 T Cells Defined by CD44 and CD122 Expression Levels. J Immunol. Mar. 15, 2002;168(6):1704-2711.

Wang et al., Alterations of APC, c-met, and p53 Genes in Tumor Tissue and Serum of Patients with Gastric Cancers. J Surg Res. Aug. 2004;120(2):242-248.

Wang et al., Cloning Genes Encoding MHC Class II-Restricted Antigens: Mutated CDC27 as a Tumor Antigen. Science May 21, 1999;284(5418):1351-1354.

Wang et al., Identification of a Novel Major Histocompatibility Complex Class II-restricted Tumor Antigen Resulting from a Chromosomal Rearrangement Recognized by CD4+ T Cells. J Exp Med. May 17, 1999;189(10):1659-1668.

\* cited by examiner

SEQ. ID NO.2
Peptide #278
EEDKSPVRDWLF

SEQ. ID NO.3
Peptide #279
DKSPVRDWLFRQ

SEQ. ID NO.4
Peptide #280
SPVRDWLFRQHQ

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Ile Asn Phe Glu Lys Leu
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Glu Glu Asp Lys Ser Pro Val Arg Asp Trp Leu Phe
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Lys Ser Pro Val Arg Asp Trp Leu Phe Arg Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Pro Val Arg Asp Trp Leu Phe Arg Gln His Gln
1               5                   10

<210> SEQ ID NO 5
<211> LENGTH: 9
<212> TYPE: PRT
<213> ORGANISM: Homo sapiens

<400> SEQUENCE: 5

Ser Gly Pro Gln Ala Cys Thr Arg Phe
1               5
```

METHODS AND COMPOSITIONS USING *LISTERIA* FOR ENHANCING IMMUNOGENICITY BY PRIME BOOST

CROSS-REFERENCE TO RELATED APPLICATIONS

This application is a continuation of U.S. patent application Ser. No. 14/589,608, filed Jan. 5, 2015, now U.S. Pat. No. 9,198,960, issued Dec. 1, 2015, which is a continuation of U.S. patent application Ser. No. 12/374,288, filed Apr. 15, 2010, now U.S. Pat. No. 8,926,993, issued Jan. 6, 2015, which is the National Stage of International Application No. PCT/US2007/016290, filed Jul. 17, 2007, which claims the benefit of Provisional Application No. 60/831,360, filed Jul. 17, 2006, each of which is hereby incorporated in its entirety including all tables, figures and claims.

SEQUENCE LISTING

The instant application contains a Sequence Listing which has been submitted via EFS-Web and is hereby incorporated by reference in its entirety. Said ASCII copy, created on Nov. 23, 2015, is named ANZ2200CT2_Sequence_List.txt, and is 2 kilobytes in size.

STATEMENT REGARDING FEDERALLY SPONSORED RESEARCH OR DEVELOPMENT

This invention was made, in part, with U.S. government support under National Cancer Institute NHI 1 K23CAI04160-01. The government may have certain rights in the invention.

BACKGROUND OF THE INVENTION

It is thought to be desirable to establish strong cellular immunity to specific pathogens. Repeated administrations with the same vaccine (homologous boosting) have proven effective for boosting humoral responses. However, this approach is relatively inefficient at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting). This strategy is referred to as "prime-boosting".

The following are examples of heterologous prime-boost regimens. Those involving a DNA prime include: a DNA prime: DNA prime/bacterial boost (*Listeria*) against viral antigens (Boyer, et al. (2005) Virology 333:88-101); a DNA prime/bacterial vector (*Bacillus*) boost, against bacterial antigen (Ferraz, et al. (2004) Infection Immunity 72:6945-6950); a DNA prime/viral vector boost, against tumor antigens (Goldberg, et al. (2005) Clin. Cancer Res. 11:8114-8121; Smith, et al. (2005) Int. J. Cancer 113:259-266); a DNA prime/viral boost against viral antigens (Toussaint, et al. (2005) Vaccine 23:5073-5081; Cebere, et al. (2006) Vaccine 24:417-425; Coupar, et al. (2006) Vaccine 24:1378-1388); a DNA prime/protein boost against viral antigens (Cristillo, et al. (2006) Virology 346:151-168; Rasmussen, et al. (2006) Vaccine 24:2324-2332); a DNA prime/viral boost, against antigens of a parasite (Gilbert, et al. (2006) Vaccine 24:4554-4561; Webster, et al. (2005) Proc. Natl. Acad. Sci. USA 102:4836-4841); DNA prime/adjuvanted protein boost, against tumor antigens (Prud'homme (2005) J. Gene Med. 7:3-17); DNA prime/viral boost plus protein boost, against viral antigens (Stambas, et al. (2005) Vaccine 23:2454-2464); and DNA prime (nanoparticles)/protein boost, against viral antigen (Castaldello, et al. (2006) Vaccine 24:5655-5669).

The following heterologous prime-boost regimens utilize prime compositions not involving DNA: Dendritic cell (DC) prime/bacterial (*Listeria*) boost, and DC prime/viral boost, against bacterial antigens (Badovinac, et al. (2005) Nat. Med. 11:748-756); bacterial vector prime (*Salmonella*)/protein boost, against bacterial antigens (Vindurampulle, et al. (2004) Vaccine 22:3744-3750; Lasaro, et al. (2005) Vaccine 23:2430-2438); adjuvanted protein prime/DNA boost, against viral antigens (Sugauchi, et al. (2006) J. Infect. Dis. 193:563-572; Pal, et al. (2006) Virology 348:341-353); protein prime/bacterial vector (*Salmonella*) boost, against viral antigens (Liu, et al. (2006) Vaccine 24:5852-5861); protein prime/viral vector boost, against viral antigen (Peacock, et al. (2004) J. Virol. 78:13163-13172); Heterologous viral prime/viral boost, using different viral vectors, against viral antigens or tumor antigens (Ranasinghe, et al. (2006) Vaccine 24:5881-5895; Kaufman, et al. (2004) J. Clin. Oncol. 22:2122-2132; Grosenbach, et al. (2001) Cancer Res. 61:4497-4505). Heterologous prime/boost using lipid vesicles, against bacterial antigens (Luijkx, et al. (2006) Vaccine 24:1569-1577).

A reagent that is useful for modulating the immune system is *Listeria* and particularly *Listeria monocytogenes* (*L. monocytogenes*). *L. monocytogenes* has a natural tropism for the liver and spleen and, to some extent, other tissues such as the small intestines (see, e.g., Dussurget, et al. (2004) Ann. Rev. Microbiol. 58:587-610; Gouin, et al. (2005) Curr. Opin. Microbiol. 8:35-45; Cossart (2002) Int. J. Med. Microbiol. 291:401-409; Vazquez-Boland, et al. (2001) Clin. Microbiol. Rev. 14:584-640; Schluter, et al. (1999) Immunobiol. 201:188-195). Where the bacterium resides in the intestines, passage to the bloodstream is mediated by listerial proteins, such as ActA and internalin A (see, e.g., Manohar, et al. (2001) Infection Immunity 69:3542-3549; Lecuit, et al. (2004) Proc. Natl. Acad. Sci. USA 101:6152-6157; Lecuit and Cossart (2002) Trends Mol. Med. 8:537-542). Once the bacterium enters a host cell, the life cycle of *L. monocytogenes* involves escape from the phagolysosome to the cytosol. This life cycle contrasts with that of *Mycobacterium*, which remains inside the phagolysosome (see, e.g., Clemens, et al. (2002) Infection Immunity 70:5800-5807; Schluter, et al. (1998) Infect. Immunity 66:5930-5938; Gutierrez, et al. (2004) Cell 119: 753-766). *L. monocytogenes*' escape from the phagolysosome is mediated by listerial proteins, such as listeriolysin (LLO), PI-PLC, and PC-PLC (see Portnoy, et al. (2002) J. Cell Biol. 158:409-414).

Methods for the prevention and treatment of cancerous disorders, such as tumors, cancers, dysplasias, angiogenesis of tumors, and methods for preventing and treating infections, are often ineffective. The invention fulfills this need by providing prime-boost strategies comprising *Listeria* bacteria.

SUMMARY OF THE INVENTION

The invention provides methods and compositions for enhancing an immune response in a mammal to a target antigen that is a non-Listerial antigen. After the mammal has been administered an effective dose of a vaccine containing the target antigen to prime the immune response to the target antigen, a second vaccine is administered. In some embodiments the first vaccine does not contain metabolically active

*Listeria* that encodes and expresses the target antigen. In other embodiments the first vaccine is comprised of killed but metabolically active ("KBMA") *Listeria* that encodes and expresses the antigen. The second vaccine is comprised of attenuated but metabolically active *Listeria* that encodes an immunologically active portion of the target antigen wherein the antigen is expressed in the infected cell. When the first vaccine contains naked DNA encoding the target antigen, the *Listeria* in the second vaccine has a mutation that inactivates ActA and/or InlB. The invention includes kits containing the first and second vaccine packaged in suitable containers, and may include instructions.

In some aspects of the invention the *Listeria* in the second vaccine has a mutation that inactivates ActA and/or InlB, and may be ΔactAΔinlB. In some aspects of the invention the *Listeria* in the second vaccine is KBMA.

In some aspects of the invention the first vaccine is comprised of a viral vector encoding the target antigen from which the target antigen is expressed. The viral vector may be adenovirus, and in some aspects is adenovirus type V.

In some aspects of the invention the target antigen is associated with cancer, and may be Mesothelin. In some aspects of the invention the prime-boost regimen results in lower tumor burden.

DETAILED DESCRIPTION OF THE INVENTION

Figure 1A:
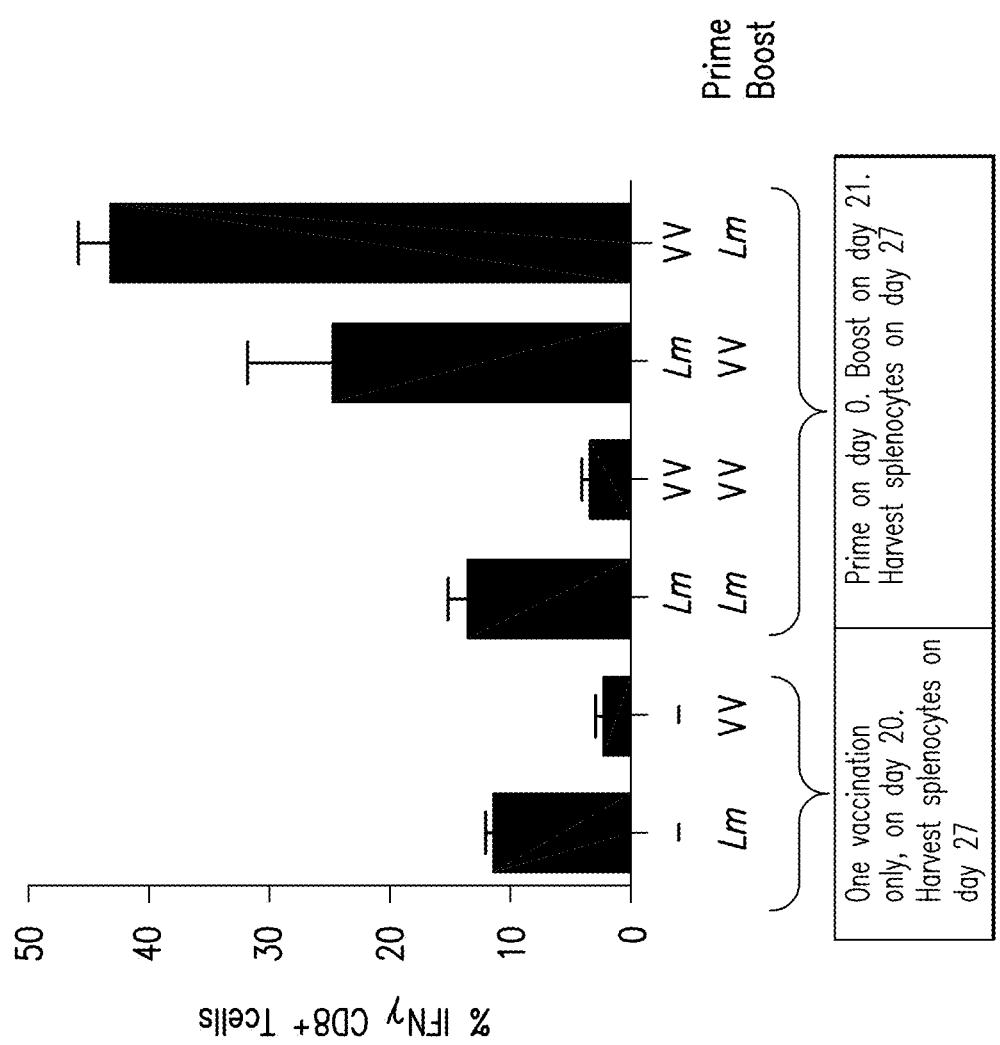
FIG. 1A is a graph showing OVA specific cellular immune responses to a target antigen (OVA) resulting from prime-boost regimens using *Listeria monocytogenes* and Vaccinia virus expressing the antigen. OVA-specific responses in vaccinated CS7BL/6 mice using $OVA_{257-264}$ peptide (SIINFEKL (SEQ ID NO: 1)) in ICS assays are shown.

The present invention relates to materials and to methods for eliciting an enhanced immune response to a target antigen that is not a Listerial antigen. The target antigen is preferably one associated with a disease, such that an immune response to the target antigen will provide a therapeutic effect. The present invention provides vaccine sets for priming and boosting an immune response, each vaccine in the set comprising either a priming agent or a boosting agent, wherein the agent in the boosting vaccine is metabolically active *Listeria* that encodes an immunologically active portion of the target antigen that is expressed in the host to which it is administered. In particular, the present invention provides methods for eliciting a boost immune response, including an enhanced boost immune response in a mammal to a target antigen. The prime dose elicits an immune response to the target antigen, and the boost dose elicits an equal or greater measurable immune response compared to the response elicited by administration of the prime dose.

The present invention is based, in part, on the findings that while a number of agents could be used in prime vaccines, boost vaccines encoding the target antigen comprised of live attenuated *Listeria monocytogenes* were far superior to boost vaccines comprised of Adenovirus or Vaccinia virus, and showed synergistic effects. In addition, it was found that immune tolerance could be broken when a mammal was subjected to a heterologous prime-boost regimen that included adenovirus in the prime vaccine, and attenuated *Listeria monocytogenes* in the boost vaccine.

The practice of the present invention will employ, unless otherwise indicated, conventional techniques including those of molecular biology (including recombinant techniques), immunology, cell biology, biochemistry, and pharmaceutical practice. Such techniques are explained fully in the literature, for example, Molecular Cloning: A Laboratory Manual, second edition, (Sambrook et al.); Methods in Enzymology (Academic Press, Inc.); Current Protocols in Molecular Biology (F. M. Ausubel et al., eds); Current Protocols in Immunology (John Wiley & Sons, Inc., N.Y.), Handbook of Pharmaceutical Excipients (Rowe et al., Eds); Vaccines (Plotkin and Orenstein, 2003); and Vaccine Protocols (Methods in Molecular Medicine) (Robinsin, Cranage and Hudson, 2003).

1. Definitions

Abbreviations used to indicate a mutation in a gene, or a mutation in a bacterium comprising the gene, are as follows. By way of example, the abbreviation "*Listeria* ΔactA" means that part, or all, of the actA gene was deleted. The delta symbol (Δ) means deletion. An abbreviation including a superscripted minus sign (*Listeria* actA$^-$) means that the actA gene was mutated, e.g., by way of a deletion, point mutation, or frameshift mutation, but not limited to these types of mutations. Exponentials may be abbreviated, for example, "3e7" means $3\times10^7$.

As used herein, including the appended claims, the singular forms of words such as "a," "an," and "the," include their corresponding plural references unless the context clearly dictates otherwise. All references cited herein are incorporated by reference in their entirety to the same extent as if each individual publication, sequences accessed by a GenBank Accession No., patent application, patent, Sequence Listing, nucleotide or oligo- or polypeptide sequence in the Sequence Listing, as well as figures and drawings in said publications and patent documents, was specifically and individually indicated to be incorporated by reference.

"Administration," as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, prophylactic, pharmacokinetic, research, placebo, and experimental methods. "Administration" to a cell encompasses contact of a reagent to the cell, as well as contact of a reagent to a fluid, where the fluid is in contact with the cell. "Administration" also encompass in vitro and ex vivo methods, e.g., of a cell, by a reagent, binding composition, or by another cell. The outcome of an administration can be assessed by, for example, increased survival time (e.g., to a life threatening proliferative disorder), decrease in tumor size, decrease in tumor number, decrease in metastasis from a specific tissue, decrease in metastasis to a specific tissue, decrease in titer of an infective agent, and the like, as compared with a placebo administration or with no administration. "Treatment" encompasses an administration where there is an expected efficacy. "Treatment" includes preventative (prophylactic) and therapeutic administrations.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells (see, e.g., Rodriguez-Pinto and Moreno (2005) Eur. J. Immunol. 35:1097-1105). Dendritic cells occur in at least two lineages. The first lineage encompasses pre-DC1, myeloid DC1, and mature DC1. The second lineage encompasses CD34$^{++}$CD45RA$^-$ early progenitor multipotent cells, CD34$^{++}$CD45RA$^+$ cells, CD34$^{++}$CD45RA$^{++}$CD4$^+$ IL-3Ralpha$^{++}$ pro-DC2 cells, CD4$^+$CD11c$^-$ plasmacytoid pre-DC2 cells, lymphoid human DC2 plasmacytoid-derived DC2s, and mature DC2s (see, e.g., Gilliet and Liu (2002) J. Exp. Med. 195:695-704; Bauer, et al. (2001) J. Immunol. 166: 5000-5007; Arpinati, et al. (2000) Blood 95:2484-2490; Kadowaki, et al. (2001) J. Exp. Med. 194:863-869; Liu (2002) Human Immunology 63:1067-1071; McKenna, et al. (2005) J. Virol. 79:17-27; O'Neill, et al. (2004) Blood 104:2235-2246; Rossi and Young (2005) J. Immunol. 175: 1373-1381; Banchereau and Palucka (2005) Nat. Rev. Immunol. 5:296-306).

"Attenuation" and "attenuated" encompasses a bacterium, virus, parasite, infectious organism, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicator of toxicity, the LD$_{50}$, the rate of clearance from an organ, or the competitive index (see, e.g., Auerbuch, et al. (2001) Infect. Immunity 69:5953-5957). Generally, an attenuation results an increase in the LD$_{50}$ by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

"Attenuated gene" encompasses a gene that mediates toxicity, pathology, or virulence, to a host, growth within the host, or survival within the host, where the gene is mutated in a way that mitigates, reduces, or eliminates the toxicity, pathology, or virulence. "Mutated gene" encompasses deletions, point mutations, insertion mutations, and frameshift mutations in regulatory regions of the gene, coding regions of the gene, non-coding regions of the gene, or any combination thereof.

"Cancerous condition" and "cancerous disorder" encompass, without implying any limitation, a cancer, a tumor, metastasis, angiogenesis of a tumor, and pre-cancerous disorders such as dysplasias. A mammalian subject with a cancer, tumor, pre-cancerous condition, pre-cancerous disorder, or cancerous disorder, and the like, encompasses a mammalian subject that comprises the cancer, per-cancerous disorder, or tumor, but also encompasses a mammalian subject where the tumor has been removed, where the cancer has been apparently eliminated (e.g., by chemotherapy or surgery or solely by the subject's immune system).

"Effective amount" as used in treatment encompasses, without limitation, an amount that can ameliorate, reverse, mitigate, or prevent a symptom or sign of a medical condition or disorder. Unless dictated otherwise, explicitly or otherwise, an "effective amount" is not limited to a minimal amount sufficient to ameliorate a condition, or to an amount that results in an optimal or a maximal amelioration of the condition. "Effective amount" within the context of administration of a prime and/or boost is that which causes an immune response in the mammal.

An "extracellular fluid" encompasses, e.g., serum, plasma, blood, interstitial fluid, cerebrospinal fluid, secreted fluids, lymph, bile, sweat, fecal matter, and urine. An "extracellular fluid" can comprise a colloid or a suspension, e.g., whole blood.

"Growth" of a *Listeria* bacterium is a term of the listerial art that encompasses intracellular growth of the *Listeria* bacterium, that is, growth inside a host cell such as a mammalian cell. While intracellular growth ("growth") of a *Listeria* bacterium can be measured by light microscopy, fluorescent microscopy, or colony forming unit (CFU) assays, growth is not to be limited by any technique of measurement. Biochemical parameters such as the quantity of a listerial antigen, listerial nucleic acid sequence, or lipid specific to the *Listeria* bacterium, can be used to assess growth. A gene that mediates growth is one that specifically mediates intracellular growth. A gene that specifically mediates intracellular growth encompasses, but is not limited to, a gene where inactivation of the gene reduces the rate of intracellular growth but does not detectably reduce the rate of extracellular growth (e.g., growth in broth), or a gene where inactivation of the gene reduces the rate of intracellular growth to a greater extent than it reduces the rate of extracellular growth. To provide non-limiting examples, a gene that mediates intracellular growth is one where its deletion cuts down intracellular growth to less than 50%, to less than 40%, to less than 30%, to less than 20%, or to less than 10%, the intracellular growth exhibited by a wild type *Listeria*. To provide further non-limiting examples, a gene that mediates intracellular growth encompasses one where its deletion cuts down intracellular growth to less than 50% the intracellular growth of the wild type *Listeria*, but only cuts down extracellular growth to about 95%, 90%, 85%, or 80% that found with wild type *Listeria*. In this context, the term "about" refers to plus or minus 5%.

"Killed but metabolically active" (KBMA) encompasses any bacterium that contains a modified genome, for example, where the genomic modification is sufficient to prevent colony formation, but where the genomic modification is not sufficient to substantially prevent or impair metabolism. A KBMA bacterium cannot form colonies, for example, as measurable on agar or in vivo in a host cell. To provide a non-limiting example, the genome can be modified with a cross-linking agent, such as psoralen. To provide a non-limiting example, a KBMA bacterium that is not at all impaired in metabolism is one where the genome contains cross-links only in intergenic regions having no regulatory, coding, structural, or biological functions. This is in contrast to a "live" bacterium which can form a colony, although in some embodiments the live bacterium may be attenuated.

"Precancerous condition" encompasses, without limitation, dysplasias, preneoplastic nodules; macroregenerative nodules (MRN); low-grade dysplastic nodules (LG-DN); high-grade dysplastic nodules (HG-DN); biliary epithelial dysplasia; foci of altered hepatocytes (FAH); nodules of altered hepatocytes (NAH); chromosomal imbalances; aberrant activation of telomerase; re-expression of the catalytic subunit of telomerase; expression of endothelial cell markers such as CD31, CD34, and BNH9 (see, e.g., Terracciano and Tomillo (2003) Pathologica 95:71-82; Su and Bannasch (2003) Toxicol. Pathol. 31:126-133; Rocken and Carl-McGrath (2001) Dig. Dis. 19:269-278; Kotoula, et al. (2002) Liver 22:57-69; Frachon, et al. (2001) J. Hepatol. 34:850-857; Shimonishi, et al. (2000) J. Hepatobiliary Pancreat. Surg. 7:542-550; Nakanuma, et al. (2003) J. Hepatobiliary Pancreat. Surg. 10:265-281). Methods for diagnosing cancer and dysplasia are disclosed (see, e.g., Riegler (1996) Semin. Gastrointest. Dis. 7:74-87; Benvegnu, et al. (1992) Liver 12:80-83; Giannini, et al. (1987) Hepatogastroenterol. 34:95-97; Anthony (1976) Cancer Res. 36:2579-2583).

"Sample" refers to a sample from a human, animal, placebo, or research sample, e.g., a cell, tissue, organ, fluid, gas, aerosol, slurry, colloid, or coagulated material. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

"Spread" of a bacterium encompasses "cell to cell spread," that is, transmission of the bacterium from a first host cell to a second host cell, as mediated, in part, by a vesicle. Functions relating to spread include, but are not limited to, e.g., formation of an actin tail, formation of a pseudopod-like extension, and formation of a double-membraned vacuole.

An "effective amount" of a "prime dose" or "prime dosage" refers to the amount of target antigen which elicits a measurable immune response in a mammalian subject as compared to the immune response in the mammalian subject in the absence of administration of the antigen.

A "vaccine" as used herein refers to a composition that is comprised of an immunogen, or that is comprised of an agent encoding the immunogen such that when the vaccine is administered to a mammal the immunogen is expressed in the mammal.

A "priming vaccine" as used herein refers to a vaccine comprising an agent(s) that encodes the target antigen to which an immune response is to be generated. Priming vaccines of the invention are administered to the subject or host in an amount effective to elicit an immune response to the target antigen.

An "effective amount" of a "boost dose" or "boost dosage" refers to the amount of antigen which elicits an immune response to the target antigen upon administration to a mammal which previously has been administered a prime dose of the target antigen.

A "boosting vaccine" as used herein refers to a vaccine comprising an agent that encodes an antigen that has an immunologically active portion of the target antigen, and may include the target antigen, be a fragment thereof, and/or be a fusion polypeptide containing at least an immunologically active portion of the target antigen joined to a region that is not normally present in the target antigen.

A "vector set" or "vaccine set" as used herein comprises a priming vector or priming vaccine and a boosting vector or boosting vaccine wherein each encode at least one of a shared immunogenic determinant, a cross reaction immunogenic determinant, a shared antigen, immunogenic protein or peptide, or fragment thereof.

An "antigen" refers to a molecule containing one or more epitopes (either linear, conformational or both) or immunogenic determinants that will stimulate a host's immune-system, such as a mammal's immune system, to make a humoral and/or cellular antigen-specific response. The term is used interchangeably with the term "immunogen." An antigen may be a whole protein, a truncated protein, a fragment of a protein or a peptide. Antigens may be naturally occurring, genetically engineered variants of the protein, or may be codon optimized for expression in a particular mammalian subject or host. Generally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature). Antibodies such as anti-idiotype antibodies, or fragments thereof, and synthetic peptide mimotopes, that is synthetic peptides which can mimic an antigen or antigenic determinant, are also captured under the definition of antigen as used herein. For purposes of the present invention, antigens can be from any of several known pathogenic viruses, bacteria, parasites and fungi. They can also be from cancers. Furthermore, for purposes of the present invention, an "antigen" refers to a protein which includes modifications, such as deletions, additions and substitutions, generally conservative in nature, to the naturally occurring sequence, so long as the protein maintains the ability to elicit an immunological response, as defined herein. These modifications may be deliberate, as through site-directed mutagenesis, or may be accidental, such as through mutations of hosts which produce the antigens. Antigens of the present invention may also be codon optimized by methods known in the art to improve their expression or immunogenicity in the host. As used herein, a "cross reaction" immunogenic determinant refers to a determinant, epitope, or antigen which is capable of eliciting an immune response to related but not identical antigenic determinants, for example a cross reaction determinant for HIV would be an antigen capable of eliciting an immune response to two or multiple or all members of the HIV antigen across clades.

An "immunological response" or "immune response" to an antigen, or vector or vaccine or composition comprising the antigen, is the development in a mammalian subject of a humoral and/or a cellular immune response to an antigen or antigens present in a vector set. A "cellular immune response" is one mediated by T-lymphocytes and/or other white blood cells, including without limitation NK cells and macrophages. T lymphocytes of the present invention include T cells expressing alpha beta T cell receptor subunits or gamma delta receptor expressing T cells and may be either effector or suppressor T cells. "T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Maturing T cells become immunocompetent based on their ability to recognize and bind a specific antigen. Activation of immunocompetent T cells is triggered when an antigen binds to the lymphocyte's surface receptors. It is known that in order to generate T cell responses, antigen must be synthesized within or introduced into cells, subsequently processed into small peptides by the proteasome complex, and translocated into the endoplasmic reticulum/Golgi complex secretory pathway for eventual association with major histocompatibility complex (MHC) class I proteins. Functionally cellular immunity includes antigen specific cytotoxic T cells (CTL). Antigen specific T cells, CTL, or cytotoxic T cells as used herein refers to cells which have specificity for peptide antigens presented in association with proteins encoded by the major histocompatability complex (MHC) or human leukocyte antigens (HLA) as the proteins are referred to in humans. CTLs of the present invention include activated CTL which have become triggered by specific antigen in the context of MHC; and memory CTL or recall CTL to refer to T cells that have become reactivated as a result of re-exposure to antigen as well as cross-reactive CTL. CTLs of the present invention include CD4+ and CD8+ T cells. Activated antigen specific CTLs of the present invention promote the destruction and/or lysis of cells of the subject infected with the pathogen or cancer cell to which the CTL are specific via amongst other things, secretion of chemokines and cytokines including without limitation macrophage inflammatory protein 1 a (MIP-1a), MIP-1B, and RANTES; and secretion of soluble factors that suppress the disease state. Cellular immunity of the present invention also refers to antigen specific response produced by the T helper subset of T cells. Helper T cells act to help stimulate the function, and focus the activity of nonspecific effector cells against cells displaying peptide in association with MHC molecules on their surface. A cellular immune response also refers to the production of cytokines, chemokines and other such molecules produced by activated T cells and/or other white blood cells including those derived from CD4 and CD8 T cells and NK cells. A prime dose or boost dose, or a composition or vaccine comprising a prime dose or a boost dose, that elicits a cellular immune response may serve to sensitize a mammalian subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays known in the art, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. (1993) 151:4189-4199; Doe et al., Eur. J. Immunol. (1994) 24:2369-2376. Methods of measuring cell-mediated immune response include measurement of intracellular cytokines or cytokine secretion by T-cell populations, or by measurement of epitope specific T-cells (e.g., by the tetramer technique) (reviewed by McMichael, A. J., and O'Callaghan, C. A., J. Exp. Med. 187(9)1367-1371, 1998; Mcheyzer-Williams, M. G., et al, Immunol. Rev. 150:5-21, 1996; Lalvani, A., et al, J. Exp. Med. 186:859-865, 1997). An immunological response, or immune response, as used herein encompasses one which stimulates the production of CTLs, and/or the production or activation of helper T-cells and/or an antibody-mediated immune response.

An "immunological response" or "immune response" as used herein encompasses at least one or more of the following effects: the production of antibodies by B-cells; and/or the activation of suppressor T-cells and/or T-cells directed specifically to an antigen or antigens present in the vectors, composition or vaccine of interest. In some embodiments, the "immunological response" or "immune response" encompasses the inactivation of suppressor T-cells. As used herein, an "enhanced boost immune response" refers to administration of boost dose by a vaccine that elicits a greater measurable immune response as compared to the response elicited by a single administration of the prime dose.

By "pharmaceutically acceptable" or "pharmacologically acceptable" is meant a material which is not biologically or otherwise undesirable.

As used herein, the term "kit" refers to components packaged and/or marked for use with each other, although not necessarily simultaneously. A kit may contain the priming vaccine and boosting vaccine in separate containers. A kit may also contain the components for a priming vaccine and/or a boosting vaccine in separate containers. A kit may also contain instructions for combining the components so as to formulate an immunogenic composition suitable for administration to a mammal.

A "therapeutic effect" is a lessening of one or more symptoms associated with a disease for which the vaccine(s) are being administered. A "prophylactic effect" is an inhibition of one or more symptoms associated with the disease for which the vaccine(s) are being administered.

As used herein "mammalian subject" or "host" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs. The term does not denote a particular age. Thus, both adult and newborn individuals are intended to be covered.

Methods of Eliciting an Enhanced Immune Response to a Target Antigen

The present invention encompasses methods for eliciting an immune response and in particular encompasses methods for eliciting a boost immune response, including an enhanced boost response to a target antigen present in a priming vaccine administered to a mammal. The target antigens may be those associated with a disease state, for example, those identified as present on a cancerous cell or a pathogenic agent. Subsequent to an effective dose of the priming vaccine, a second vaccine comprising an attenuated metabolically active *Listeria* that encodes and expresses an immunologically active portion of the target antigen is administered.

1. Target Antigens

Examples of target antigens that may used in the prime-boost regimens of the invention are listed in the following table. The target antigen may also be a fragment or fusion polypeptide comprising an immunologically active portion of the antigens listed in the table.

TABLE 1

Antigens.

| Antigen | Reference |
|---|---|
| Tumor antigens | |
| Mesothelin | GenBank Acc. No. NM_005823; U40434; NM_013404; BC003512 (see also, e.g., Hassan, et al. (2004) Clin. Cancer Res. 10:3937-3942; Muminova, et al. (2004) BMC Cancer 4:19; Iacobuzio-Donahue, et al. (2003) Cancer Res. 63:8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583, See also, e.g., Bondurant, et al. (2005) Clin. Cancer Res. 11:3446-3454; Santin, et al. (2004) Gynecol. Oncol. 94:283-288; Shigemasa, et al. (2001) Int. J. Gynecol. Cancer 11:454-461; Sepehr, et al. (2001) Oncogene 20:7368-7374. |
| MHC class I chain-related protein A (MICA); MHC class I chain-related protein A (MICB). | See, e.g., Groh, et al. (2005) Proc. Natl. Acad. Sci. USA 102:6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64:5624-5631; Gilliam, et al. (2004) Eur. J. Surg. Oncol. 30:536-543; Laheru and Jaffee (2005) Nature Reviews Cancer 5:459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306:16-25; Capurro, et al. (2003) Gasteroenterol. 125:89-97; Nakatsura, et al. (2004) Clin. Cancer Res. 10:6612-6621). |
| Coactosin-like protein. | Nakatsura, et al. (2002) Eur. J. Immunol. 32:826-836:Laheru and Jaffee (2005) Nature Reviews Cancer 5:459-467. |
| Prostate stem cell antigen (PSCA). | GenBank Acc. No. AF043498; AR026974; AR302232 (see also, e.g., Argani, et al. (2001) Cancer Res, 61:4320-4324; Christiansen, et al. (2003) Prostate 55:9-19; Fuessel, et al. (2003) 23:221-228). |

TABLE 1-continued

Antigens.

| Antigen | Reference |
|---|---|
| Prostate acid phosphatase (PAP); prostate-specific antigen (PSA); PSM; PSMA. | Small, et al. (2000) J. Clin. Oncol. 18:3894-3903; Altwein and Luboldt (1999) Urol. Int. 63:62-71; Chan, et al. (1999) Prostate 41:99-109; Ito, et al. (2005) Cancer 103:242-250; Schmittgen, et al. (2003) Int. J. Cancer 107:323-329; Millon, et al. (1999) Eur. Urol. 36:278-285. |
| Six-transmembrane epithelial antigen of prostate (STEAP). | See, e.g., Machlenkin, et al. (2005) Cancer Res. 65:6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65:6435-6442; GenBank Acc. No. L78132. |
| Prostate tumor-inducing gene-1 (PTI-1). | See, e.g., Machlenkin, et al. (2005) Cancer Res. 65:6435-6442). |
| Prostate-specific gene with homology to G protein-coupled receptor. | See, e.g., Machlenkin, et al. (2005) Cancer Res. 65:6435-6442). |
| Prostase (an antrogen regulated serine protease). | See, e.g., Machlenkin, et al. (2005) Cancer Res. 65:6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11:1809-1814; Chen, et al. (2004) Proc. Natl. Acad. Sci. USA. 101(25):9363-9368; Kubuschok, et al. (2004) Int. J. Cancer, 109:568-575; Scanlan, et al. (2004) Cancer Immun. 4:1; Scanlan, et al. (2002) Cancer Res. 62:4041-4047; Scanlan, et al. (2000) Cancer Lett. 150:155-164; Dalerba, et al. (2001) Int. J. Cancer 93:85-90; Ries, et al. (2005) Int. J. Oncol. 26:817-824. |
| MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) Cancer Res. 61:6682-6687; Lee, et al. (2003) Proc. Natl. Acad. Sci. USA 100:2651-2656; Sarcevic, et al. (2003) Oncology 64:443-449; Lin, et al. (2004) Clin. Cancer Res. 10:5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res, 59:3157-3165; Scarcella, et al. (1999) Clin. Cancer Res. 5:335-341. |
| HIP1R; LMNA; KIAA1416; Seb4D; KNSL6; TRIP4; MBD2; HCAC5; MAGEA3. | Scanlan, et al. (2002) Cancer Res. 62:4041-4047. |
| DAM family of genes, e.g., DAM-1; DAM-6. | Fleishhauer, et al. (1998) Cancer Res. 58:2969-2972. |
| RCAS1. | Enjoji, et al. (2004) Dig. Dis. Sci. 49:1654-1656. |
| RU2. | Van Den Eynde, et al. (1999) J. Exp. Med. 190:1793-1800. |
| CAMEL. | Slager, et al. (2004) J. Immunol. 172:5095-5102; Slager, et al. (2004) Cancer Gene Ther. 11:227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62:4041-4047. |
| N-Acetylglucosaminyl-tranferase V (GnT-V). | Dosaka-Akita, et al. (2004) Clin. Cancer Res. 10:1773-1779. |
| Elongation factor 2 mutated (ELF2M). | Renkvist, et al. (2001) Cancer Immunol Immunother. 50:3-15. |

TABLE 1-continued

Antigens.

| Antigen | Reference |
|---|---|
| HOM-MEL-40/SSX2 | Neumann, et al. (2004) Int. J. Cancer 112:661-668; Scanlan, et al. (2000) Cancer Lett. 150:155-164. |
| BRDT. | Scanlan, et al. (2000) Cancer Lett. 150:155-164. |
| SAGE; HAGE. | Sasaki, et al. (2003) Eur. J. Surg. Oncol. 29:900-903. |
| RAGE. | See, e.g., Li, et al. (2004) Am. J. Pathol. 164:1389-1397; Shirasawa, et al. (2004) Genes to Cells 9:165-174. |
| MUM-1 (melanoma ubiquitous mutated); MUM-2; MUM-2 Arg-Gly mutation; MUM-3. | Gueguen, et al. (1998) J. Immunol. 160:6188-6194; Hirose, et al. (2005) Int. J. Hematol. 81:48-57; Baurain, et al. (2000) J. Immunol. 164:6057-6066; Chiari, et al. (1999) Cancer Res. 59:5785-5792. |
| LDLR/FUT fusion protein antigen of melanoma. | Wang, et al. (1999) J. Exp. Med. 189:1659-1667. |
| NY-REN series of renal cancer antigens. | Scanlan, et al. (2002) Cancer Res. 62:4041-4047; Scanlan, et al. (1999) Cancer Res. 83:456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62:4041-4047; Scanlan, et al. (2001) Cancer Immunity 1:4. |
| BRCA-1; BRCA-2. | Stolier, et al. (2004) Breast J. 10:475-480; Nicoletto, et al. (2001) Cancer Treat Rev. 27:295-304. |
| DEK/CAN fusion protein. | Von Lindern, et al. (1992) Mol. Cell. Biol. 12:1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123:256-2601; Tsao and Sober (2005) Dermatol. Clin. 23:323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, eg., Suzuki, et al. (1999) J. Immunol. 163:2783-2791. |
| Survivin | GenBank Acc. No. AB028869; U75285 (see also, e.g., Tsuruma, et al. (2004) J. Translational Med. 2:19 (11 pages); Pisarev, et al. (2003) Clin. Cancer Res. 9:6523-6533; Siegel, et al. (2003) Br. J. Haematol. 122:911-914; Andersen, et al. (2002) Histol. Histopathol. 17:669-675). |
| MDM-2 | NM_002392; NM_006878 (see also, e.g., Mayo, et al. (1997) Cancer Res. 57:5013-5016; Demidenko and Blagosklonny (2004) Cancer Res. 64:3653-3660). |
| Methyl-CpG-binding proteins (MeCP2; MBD2). | Muller, et al. (2003) Br. J. Cancer 89:1934-1939; Fang, et al. (2004) World J. Gastreenterol. 10:3394-3398. |
| NA88-A. | Moreau-Aubry, et al. (2000) J. Exp. Med. 191:1617-1624. |
| Histone deacetylases (HDAC), e.g., HDAC5. | Waltregny, et al. (2004) Eur. J. Histochem. 48:273-290; Scanlan, et al. (2002) Cancer Res. 62:4041-4047. |
| Cyclophilin B (Cyp-B). | Tamura, et al. (2001) Jpn. J. Cancer Res. 92:762-767. |
| CA 15-3; CA 27.29. | Clinton, et al. (2003) Biomed. Sci. Instrum. 39:408-414. |
| Heat shock protein Hsp70. | Faure, et al. (2004) Int. J. Cancer 108:863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59:1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87:55-60; Scanlan, et al. (2001) Cancer Immun. 1:4. |
| Kinesin 2; TATA element modulatory factor 1; tumor protein D53; NY | Scanlan, et al. (2001) Cancer Immun. 30:1-4. |
| Alpha-fetoprotein (AFP) | Grimm, et al. (2000) Gastroenterol. 119:1104-1112. |
| SART1; SART2; | Kumamuru, et al. (2004) Int. J. Cancer 108:686-695; Sasatomi, et al. |

TABLE 1-continued

Antigens.

| Antigen | Reference |
|---|---|
| SART3; ART4. | (2002) Cancer 94:1636-1641; Matsumoto, et al. (1998) Jpn. J. Cancer Res. 89:1292-1295; Tanaka, et al. (2000) Jpn. J. Cancer Res. 91:1177-1184. |
| Preferentially expressed antigen of melanoma (PRAME). | Matsushita, et al. (2003) Leuk. Lymphoma 44:439-444; Oberthuer, et al. (2004) Clin. Cancer Res. 10:4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57:4570-4577; Sarobe, et al. (2004) Curr. Cancer Drug Targets 4:443-454; Tsang, et al. (1997) Clin. Cancer Res. 3:2439-2449; Fong, et al. (2001) Proc. Natl. Acad. Sci. USA 98:8809-8814). |
| HER-2/neu. | Disis, et al. (2004) J. Clin. Immunol. 24:571-578; Disis and Cheever (1997) Adv. Cancer Res. 71:343-371. |
| Cdk4; cdk6; p16 (INK4); Rb protein. | Ghazizadeh, et al. (2005) Respiration 72:68-73; Ericson, et al. (2003) Mol. Cancer Res. 1:654-664. |
| TEL; AML1; TEL/AML1. | Stams, et al. (2005) Clin. Cancer Res. 11:2974-2980. |
| Telomerase (TERT). | Nair, et al. (2000) Nat. Med. 6:1011-1017. |
| 707-AP. | Takahashi, et al. (1997) Clin. Cancer Res. 3:1363-1370. |
| Annexin, e.g., Annexin II. | Zimmerman, et al. (2004) Virchows Arch. 445:368-374. |
| BCR/ABL; BCR/ABL p210; BCR/ABL p190; CML-66; CML-28. | Cobaldda, et al. (2000) Blood 95:1007-1013; Hakansson, et al. (2004) Leukemia 18:538-547; Schwartz, et al. (2003) Semin. Hematol. 40:87-96; Lim, et al. (1999) Int. J. Mol. Med. 4:665-667. |
| BCL2; BLC6; CD10 protein. | Iqbal, et al. (2004) Am. J. Pathol. 165:159-166. |
| CDC27 (this is a melanoma antigen). | Wang, et al. (1999) Science 284:1351-1354. |
| Sperm protein 17 (SP17); 14-3-3-zeta; MEMD; KIAA0471; TC21. | Arora, et al. (2005) Mol. Carcinog. 42:97-108. |
| Tyrosinase-related proteins 1 and 2 (TRP-1 and TRP-2). | GenBank Acc. No. NM_001922. (see also, e.g., Bronte, et al. (2000) Cancer Res. 60:253-258). |
| Gp100/pmel-17. | GenBank Acc. Nos. AH003567; U31798; U31799; U31807; U31799 (see also, e.g., Bronte, et al. (2000) Cancer Res. 60:253-258). |
| TARP. | See, e.g., Clifton, et al. (2004) Proc. Natl. Acad. Sci. USA 101:10166-10171; Virok, et al. (2005) Infection Immunity 73:1939-1946. |
| Tyrosinase-related proteins 1 and 2 (TRP-1 and TRP-2). | GenBank Acc. No. NM_001922. (see also, e.g., Bronte, et al. (2000) Cancer Res. 60:253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57:4348-4355; Reynolds, et al. (1998) J. Immunol. 161:6970-6976; Chang, et al. (2002) Clin. Cancer Res. 8:1021-1032. |
| MUC-1; MUC-2. | See, e.g., Davies, et al. (1994) Cancer Lett. 82:179-184; Gambus, et al. (1995) Int. J. Cancer 60:146-148; McCool, et al. (1999) Biochem. J. 341:593-600. |
| Spas-1. | U.S. Published Pat. Appl. No. 20020150588 of Allison, et al. |
| CASP-8; FLICE; MACH. | Mandruzzato, et al. (1997) J. Exp. Med. 186:785-793. |
| CEACAM6; CAP-1. | Duxbury, et al. (2004) Biochem. Biophys. Res. Commun. 317:837-843; Morse, et al. (1999) Clin. Cancer Res. 5:1331-1338. |
| HMGB1 (a DNA binding protein and cytokine). | Brezniceanu, et al. (2003) FASEB J. 17:1295-1297. |
| ETV6/AML1. | Codrington, et al. (2000) Br. J. Haematol. 111:1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3:113-120; Gulmann, et al. (2003) Appl. Immunohistochem. Mol. Morphol. 11:230-237; Jungck, et al. (2004) Int. J. Colorectal. Dis. 19:438-445; Wang, et al. (2004) J. Surg. Res. 120:242-248; Abutaily, et al. (2003) J. Pathol. 201:355-362; Liang, et al. (2004) Br. J. Surg. 91:355-361; Shirakawa, et al. (2004) Clin. Cancer Res. 10:4342-4348. |
| Renal cell carcinoma antigen bound by mAB G250. | Mulders, et al. (2003) Urol. Clin. North Am. 30:455-465; Steffens, et al. (1999) Anticancer Res. 19:1197-1200. |
| EphA2 | See, e.g., U.S. Patent Publication No. 2005/0281783 A1; Genbank Accession No. NM_004431 (human):Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 |

TABLE 1-continued

| Antigens. | |
|---|---|
| Antigen | Reference |
| | (chicken). |
| | *Francisella tularensis* antigens |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27:922-926; Porsch-Ozcurumez, et al. (2004) Clin. Diagnostic. Lab. Immunol. 11:1008-1015). Antigenic components of *F. tularensis* include, e.g., 80 antigens, including 10 kDa and 60 kDa chaperonins (Havlasova, et al. (2002) Proteomics 2:857-86), nucleoside diphosphate kinase, isocitrate dehydrogenase, RNA-binding protein Hfq, the chaperone ClpB (Havlasova, et al. (2005) Proteomics 5:2090-2103). See also, e.g., Oyston and Quarry (2005) Antonie Van Leeuwenhoek 87:277-281; Isherwood, et al. (2005) Adv. Drug Deliv. Rev. 57:1403-1414; Biagini, et al. (2005) Anal. Bioanal. Chem. 382:1027-1034. |
| | Malarial antigens |
| Circumsporozoite protein (CSP); SSP2; HEP17; Exp-1 orthologs found in *P. falciparum*; and LSA-1. | See, e.g., Haddad, et al. (2004) Infection Immunity 72:1594-1602; Hoffman, et al. (1997) Vaccine 15:842-845; Oliveira-Ferreira and Daniel-Ribeiro (2001) Mem. Inst. Oswaldo Cruz, Rio de Janeiro 96:221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29:579-586; Krzych, et al. (1995) J. Immunol. 155:4072-4077. See also, Good, et al. (2004) Immunol. Rev. 201:254-267; Good, et al. (2004) Ann. Rev. Immunol. 23:69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41:186-198. AMA1 (see, e.g., GenBank Acc. No. A'13; AJ494905; AJ490565). |
| | Viruses and viral antigens |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21:4036-4042; Kim, et al. (2004) Gene Ther. 11:1011-1018; Simon, et al. (2003) Eur. J. Obstet. Gynecol. Reprod. Biol. 109:219-223; Jung, et al. (2004) J. Microbiol. 42:255-266; Damasus-Awatai and Freeman-Wang (2003) Curr. Opin. Obstet. Gynecol. 15:473-477; Jansen and Shaw (2004) Annu. Rev. Med. 55:319-331; Roden and Wu (2003) Expert Rev. Vaccines 2:495-516; de Villiers, et al. (2004) Virology 324:17-24; Hussain and Paterson (2005) Cancer Immunol. Immunother. 54:577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib,Iic, and Iid. | See, e.g., Capdepont, et al. (2005) AIDS Res. Hum. Retrovirus 21:28-42; Bhigjee, et al. (1999) AIDS Res. Hum. Restrovirus 15:1229-1233; Vandamme, et al. (1998) J. Virol. 72:4327-4340; Vallejo, et al. (1996) J. Acquir. Immune Defic. Syndr. Hum. Retrovirol. 13:384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), md Toroviruses. | See, e.g., Brian and Baric (2005) Curr. Top. Microbiol. Immunol. 287:1-30; Gonzalez, et al. (2003) Arch. Virol. 148:2207-2235; Smits, et al. (2003) J. Virol. 77:9567-9577; Jamieson, et al. (1998) J. Infect. Dis. 178:1263-1269 (GenBank Acc. Nos. AY348314; NC_004718; AY394850). |
| Rubella virus. | GenBank Acc. Nos. NC_001545; AF435866. |
| Mumps virus, including | See, e.g., Orvell, eta l. (2002) J. Gen. Virol. 83:2489-2496. See, e.g., |

TABLE 1-continued

Antigens.

| Antigen | Reference |
|---|---|
| the genotypes A, C, D, G, H, and I. | GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77:8973-8984. GenBank Acc. Nos. AY421768; AY790926:X67706. |
| Coxsackie virus B, including subtypes 1-6. | See, e.g., Ahn, et al. (2005) J. Med. Virol. 75:290-294; Patel, et al. (2004) J. Virol. Methods 120:167-172; Rezig, et al. (2004) J. Med. Virol. 72:268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78:855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77:4827-4835; Hahsido, et al. (1999) Microbiol. Immunol. 43:73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170:92-105; Estrada-Franco, et al. (2004) Emerg. Infect. Dis. 10:2113-2121; Das, et al. (2004) Antiviral Res. 64:85-92; Aguilar, et al. (2004) Emerg. Infect, Dis. 10:880-888; Weaver, et al. (2004) Arch. Virol. Suppl. 18:43-64; Weaver, et al. (2004) Annu. Rev. Entomol. 49:141-174. Eastern equine encephalitis (GenBank Acc. No. NC_003899; AY722102); Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32:237-248; Padilla, et al. (2003) J. Med. Virol. 70 (Suppl. 1) S103-S110; Jainkittivong and Langlais (1998) Oral Surg. Oral Med. 85:399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virul. 66:235-240. |
| HIV-1 including group M (including subtypes A to J) and group O (including any distinguishable subtypes) (HIV-2, including subtypes A-E. | See, e.g., Smith, et al. (1998) J. Med. Virol. 56:264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34:446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43:425-430; Roner, et al. (1995) Proc. Natl. Acad. Sci. USA 92:12362-12366:Kedl, et al. (1995) J. Virol. 69:552-559. GenBank Acc. No. K02739 (sigma-3 gene surface protein). |

TABLE 1-continued

Antigens.

| Antigen | Reference |
| --- | --- |
| Cytomegalovirus (CMV) subtypes include CMV subtypes I-VII. | See, e.g., Chern, et al. (1998) J. Infect. Dis. 178:1149-1153; Vilas Boas, et al. (2003) J. Med. Virol. 71:404-407; Trincado, et al. (2000) J. Med. Virol. 61:481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Varicella-zoster virus, including strains and genotypes Oka, Dumas, European, Japanese, and Mosaic. | See, e.g., Loparev, et al. (2004) J. Virol. 78:8349-8358:Carr, et al. (2004) J. Med. Virol. 73:131-136; Takayama and Takayama (2004) J. Clin. Virol. 29:113-119. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39:129-150; Hutchinson, et al. (2001) J. Med. Virol. 65:561-566. Marburg virus (see, e.g., GenBank Acc. No. NC_001608). Ebola virus (see, e.g., GenBank Acc. Nos. NC_006432:AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35:1122-1130; Sjolander, et al. (2002) Epidemiol. Infect. 128:99-103; Zeier, et al. (2005) Virus Genes 30:157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3:13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |

TABLE 1-continued

Antigens.

| Antigen | Reference |
|---|---|
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see. e.g., GenBank Acc. Nos. AY626144(. Influenza basic protein 1 (see, e.g., GenBank Acc. No. AY627897), Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV):H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055:BD006052. See also, e.g., Wentworth, et al. (1994) J. Virol. 68:2051-2058; Wells, et al. (1991) J.A.M.A. 265:478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190:2065-2069; Vilchez and Butel (2004) Clin. Microbiol. Rev. 17:495-508; Shivapurkar, et al. (2004) Cancer Res. 64:3757-3760; Carbone, et al. (2003) Oncogene 2:5173-5180; Barbanti-Brodano, et al. (2004) Virology 318:1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79:2481-2489. Segments of Eyach virus (see, e.g., GenBank Acc. Nos. AF282475; AF282472; AF282473; AF282478:AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118:71-77; Alvarez-Lafuente, et al. (2005) Ann. Rheum. Dis. 64:780-782; Ziyaeyan, et al. (2005) Jpn. J. Infect. Dis. 58:95-97; Kaufman, et al. (2005) Virology 332:189-198. |

2. Agents Used in Priming Vaccines

In the methods of the invention an initial immune response is elicited by administering to the mammal an effective dose of a priming vaccine. The priming vaccine, with the exception of KBMA-*Listeria*, does not contain metabolically active *Listeria* that encodes the target antigen. The priming vaccine may contain either the target antigen itself, for example, a protein with or without an adjuvant, a tumor cell lysate, an irradiated tumor cell, an antigen-presenting cell pulsed with peptides of the target antigen (e.g. a dendritic cell), or it may contain an agent that provides the target antigen. Suitable agents that provide a target antigen include recombinant vectors, for example, bacteria, viruses, and naked DNA. Recombinant vectors are prepared using standard techniques known in the art, and contain suitable control elements operably linked to the nucleotide sequence encoding the target antigen. See, for example, Plotkin, et al. (eds.) (2003) Vaccines, 4$^{th}$ ed., W.B. Saunders, Co., Phila., Pa.; Sikora et al. (eds.) (1996) Tumor Immunology Cambridge University Press, Cambridge, UK; Hackett and Ham (eds.) Vaccine Adjuvants, Humana Press, Totowa, N.J.; Isaacson (eds.) (1992) Recombinant DNA Vaccines, Marcel Dekker, NY, N.Y.; Morse, et al. (eds.) (2004) Handbook of Cancer Vaccines, Humana Press, Totowa, N.J.), Liao, et al. (2005) Cancer Res. 65:9089-9098; Dean (2005) Expert Opin. Drug Deliv. 2:227-236; Arlen, et al. (2003) Expert Rev. Vaccines 2:483-493; Dela Cruz, et al. (2003) Vaccine 21:1317-1326; Johansen, et al. (2000) Eur. J. Pharm. Biopharm. 50:413-417; Excler (1998) Vaccine 16:1439-1443; Disis, et al. (1996) J. Immunol. 156:3151-3158). Peptide vaccines are described (see, e.g., McCabe, et al. (1995) Cancer Res. 55:1741-1747; Minev, et al. (1994) Cancer Res. 54:4155-4161; Snyder, et al. (2004) J. Virology 78:7052-7060.

Virus-derived vectors include viruses, modified viruses, and viral particles (see, e.g., Table 2). The virus-derived vectors can be administered directly to a mammalian subject, or can be introduced ex vivo into an antigen presenting cell (APC), where the APC is then administered to the subject.

Viral vectors may be based on, e.g., Togaviruses, including alphaviruses and flaviviruses; alphaviruses, such as Sindbis virus, Sindbis strain SAAR86, Semliki Forest virus (SFV), Venezuelan equine encephalitis (VEE), Eastern equine encephalitis (EEE), Western equine encephalitis, Ross River virus, Sagiyami virus, O'Nyong-nyong virus, Highlands J virus. Flaviviruses, such as Yellow fever virus, Yellow fever strain 17D, Japanese encephalitis, St. Louis encephalitis, Tick-borne encephalitis, Dengue virus, West Nile virus, Kunjin virus (subtype of West Nile virus); arterivirus such as equine arteritis virus; and rubivirus such as rubella virus, herpesvirus, modified vaccinia Ankara (MVA); avipox viral vector; fowlpox vector; vaccinia virus vector; influenza virus vector; adenoviral vector, human papilloma virus vector; bovine papilloma virus vector, and so on. Viral vectors may be based on an orthopoxvirus such as variola virus (smallpox), vaccinia virus (vaccine for smallpox), Ankara (MVA), or Copenhagen strain, camelpox, monkeypox, or cowpox. Viral vectors may be based on an avipoxvirus virus, such as fowlpox virus or canarypox virus.

Adenoviral vectors and adeno-associated virus vectors (AAV) are available, where adenoviral vectors include adenovirus serotype 5 (adeno5; Ad5), adeno6, adeno11, and adeno35. Available are at least 51 human adenovirus serotypes, classified into six subgroups (subgroups A, B, C, D, E, and F). Adenovirus proteins useful, for example, in assessing immune response to an "empty" advenoviral vector, include hexon protein, such as hexon 3 protein, fiber protein, and penton base proteins, and human immune responses to adenoviral proteins have been described (see, e.g., Wu, et al. (2002) J. Virol. 76:12775-12782; Mascola (2006) Nature 441:161-162; Roberts, et al. (2006) Nature 441:239-243).

TABLE 2

Virus-derived vaccine vectors.

| | |
|---|---|
| Adenoviral vectors and adeno-associated virus vectors (AAV). | Polo and Dubensky (2002) Drug Discovery Today 7:719-727; Xin, et al. (2005) Gene Ther. 12:1769-1777; Morenweiser (2005) Gene Ther. 12 (Suppl. 1) S103-S110; Casimiro, et al. (2005) J. Virol. 79:15547-15555; Ferreira, et al. (2005) Gene Ther. 12 Suppl. 1:S73-S83; Baez-Astua, et al. (2005) J. Virol 79:12807-12817; Vanniasinkam and Ertl (2005) Curr. Gene Ther. 5:203-212; Tatsis and Ertl (2004) Mol. Ther. 10:616-629; Santosuosso, et al. (2005) Viral Immunol. 18:283-291; Zhou, et al. (1996) J. Virol. 70:7030-7038; Zhou, et al. (2002) J. Gene Med. 4:498-509. |
| Vaccinia virus | Kim, et al. (2005) Hum. Gen. Ther. 16:26-34; Kaufman, et al. (2005) J. Clin. Invest. 115:1903-1912; Kaufman, et al. (2004) J. Clin. Oncol. 22:2122-2132; Marshall, et al. (2005) J. Clin. Invest. 23:720-731; Hwang and Sanda (1999) Curr. Opin. Mol. Ther. 1:471-479; Baldwin, et al. (2003) Clin. Cancer Res. 9:5205-5213; |
| Modified vaccinia Ankara (MVA) | Mackova, et al. (2006) Cancer Immunol. Immunother. 55:39-46; Meyer, et al. (2005) Cancer Immunol. Immunother. 54:453-467; Palmowski, et al. (2002) J. Immunol. 168:4391-4398; |
| Vaccinia derivative NYVAC | Paoletti (1996) Proc. Natl. Acad. Sci. USA 93:11349-11353; |
| Poxviruses, including avipox, e.g., fowlpox and canarypox | Kaufman (2005) J. Clin. Oncol. 23:659-661; Kudo-Saito, et al. (2004) Clin. Cancer Res. 10:1090-1099; Greiner, et al. (2002) Cancer Res. 62:6944-6951; Marshall, et al. (2005) J. Clin. Invest. 23:720-731; Hwang and Sanda (1999) Curr. Opin. Mol. Ther. 1:471-479; Hodge, et al. (1997) Vaccine 15:759-768; Skinner, et al. (2005) Expert Rev. Vaccines 4:63-76; Rosenberg, et al. (2003) Clin. Cancer Res. 9:2973-2980. |
| Antigen presenting cells transduced with a virus-derived vector. | Di Nicola, et al. (2004) Clin. Cancer Res. 10:5381-5390; |
| Alphavirus-derived vectors, e.g., Sindbis virus, Semliki Forest virus, and Venezuelan equine encephalitis (VEE). | Polo and Dubensky (2002) Drug Discovery Today 7:719-727; Polo, et al. (1999) Proc. Natl. Acad. Sci. USA 96:4598-4603; Schlesinger (2001) Expert Opin. Biol. Ther. 1:177-191; Pan, et al. (2005) Proc. Natl. Acad. Sci. USA 102:11581-11588; Lundstrom (2003) Expert Rev. Vaccines 2:447-459; Shafferman, et al. (1996) Adv. Exp. Med. Biol. 397:41-47; Yamanaka (2004) Int. J. Oncol. 24:919-923; Atkins, et al. (2004) Curr. Cancer Drug Targets 4:597-607. |
| Chimeric virus-derived vectors, such as chimeric alphaviruses. | Sindbis virus/Venezualan equine encephalitis virus (SINV/VEEV) (see, e.g., Perri, et al. (2003) J. Virol. 77:10394-10403; Paessler, et al. (2003) J. Virol. 77:9278-9286). |
| Herpesviruses, including herpes simplex and Epstein-Barr virus-derived vectors | Hellebrand, et al. (2006) Gene Ther. 13:150-162; Lauterbach, et al. (2005) J. Gen. Virol. 86:2401-2410; Zibert, et al. (2005) Gene Ther. 12:1707-1717; Thiry, et al. (2006) Vet. Microbiol. 113:171-177; Trapp, et al. (2005) J. Virol. 79:5445-5454. |
| Rhinoviruses | Dollenmaier, et al. (2001) Virology 281:216-230; Arnold, et al. (1996) Intervirology 39:72-78. |
| Lentiviruses | DePolo, et al. (2000) Mol. Ther. 2:218-222; Pellinen, et al. (2004) Int. J. Oncol. 25:1753-1762; Esslinger, et al. (2003) J. Clin. Invest. 111:1673-1681; Kikuchi, et al. (2004) Clin. Cancer Res. 10:1835-1842; Kim, et al. (2005) Hum. Gene Ther. 16:1255-1266. |
| Viral particle vaccines | Polo and Dubensky (2002) Drug Discovery Today 7:719-727; Cheng, et al. (2002) Hum. Gene Ther. 13:553-568; Lin, et al. (2003) Mol. Ther. 8:559-566; Balasuriya, et al. (2000) J. Virol. 74:10623-10630; Goldberg, et al. (2005) Clin. Cancer Res. 11:8114-8121; Johnston, et al. (2005) Vaccine 23:4969-4979;Quinnan, et al. (2005) J. Virol. 79:3358-3369; Cassetti, et al. (2004) Vaccine 22:520-527; |

TABLE 2-continued

Virus-derived vaccine vectors.

Williamson, et al. (2003) AIDS Res. Hum. Retroviruses 19:133-144;
Perri, et al. (2003) J. Virol. 77:10394-10403; Da Silva, et al. (2003)
Vaccine 21:3219-3227;

Antigen presenting cell (APC) vectors, such as a dendritic cell (DC) vector, include cells that are loaded with an antigen, loaded with a tumor lysate, or transfected with a composition comprising a nucleic acid, where the nucleic acid can be, e.g., a plasmid, mRNA, or virus. DC/tumor fusion vaccines may also be used. See, e.g., Di Nicola, et al. (2004) Clin. Cancer Res. 10:5381-5390; Cerundolo, et al. (2004) Nature Immunol. 5:7-10; Parmiani, et al. (2002) J. Natl. Cancer Inst. 94:805-818; Kan, et al. (2005) Immunol. Lett. 101:154-159; Geiger, et al. (2005) J. Transl. Med. 3:29; Osada, et al. (2005) Cancer Immunol. Immunother. November 5, 1-10 [epub ahead of print]; Malowany, et al. (2005) Mol. Ther. 13:766-775; Morse and Lyerly (2002) World J. Surg. 26:819-825; Gabrilovich (2002) Curr. Opin. Mol. Ther. 4:454-458; Morse, et al. (2003) Clin. Breast Cancer 3 Suppl. 4:S164-S172; Morse, et al. (2002) Cancer Chemother. Biol. Response Modif. 20:385-390; Arlen, et al. (2003) Expert Rev. Vaccines 2:483-493; Morse and Lyerly (1998) Expert Opin. Investig. Drugs 7:1617-1627; Hirschowitz, et al. (2004) J. Clin. Oncol. 22:2808-2815; Vasir, et al. (2005) Br. J. Haematol. 129:687-700; Koido, et al. (2005) Gynecol. Oncol. 99:462-471.

Tumor cells, for example, autologous and allogeneic tumor cells, are available as vaccines (Arlen, et al. (2005) Semin. Oncol. 32:549-555). A vaccine may also comprise a modified tumor cell, for example, a tumor cell lysate, or an irradiated tumor cell. The tumor cell can also be modified by incorporating a nucleic acid encoding an molecule such as a cytokine (GM-CSF, IL-12, IL-15, and the like), a NKG2D ligand, CD40L, CD80, CD86, and the like (see, e.g., Dranoff (2002) Immunol. Rev. 188:147-154; Jain, et al. (2003) Ann. Surg. Oncol. 10:810-820; Borrello and Pardoll (2002) Cytokine Growth Factor Rev. 13:185-193; Chen, et al. (2005) Cancer Immunol. Immunother. 27:1-11; Kjaergaard, et al. (2005) J. Neurosurg. 103:156-164; Tai, et al. (2004) J. Biomed. Sci. 11:228-238; Schwaab, et al. (2004) J. Urol. 171:1036-1042; Friese, et al. (2003) Cancer Res. 63:8996-9006; Briones, et al. (2002) Cancer Res. 62:3195-3199; Vieweg and Dannull (2003) Urol. Clin. North Am. 30:633-643; Mincheff, et al. (2001) Crit. Rev. Oncol. Hematol. 39:125-132).

Vaccines may include naked DNA vectors and naked RNA vectors. These vaccines containing nucleic acids may be administered by a gene gun, electroporation, bacterial ghosts, microspheres, microparticles, liposomes, polycationic nanoparticles, and the like (see, e.g., Donnelly, et al. (1997) Ann. Rev. Immunol. 15:617-648; Mincheff, et al. (2001) Crit. Rev. Oncol. Hematol. 39:125-132; Song, et al. (2005) J. Virol. 79:9854-9861; Estcourt, et al. (2004) Immunol. Rev. 199:144-155).

Reagents and methodologies for administration of naked nucleic acids, e.g., by way of a gene gun, intradermic, intramuscular, and electroporation methods, are available. The nucleic acid vaccines may comprise a locked nucleic acid (LNA), where the LNA allows for attachment of a functional moiety to the plasmid DNA, and where the functional moiety can be an adjuvant (see, e.g., Fensterle, et al. (1999) J. Immunol. 163:4510-4518; Strugnell, et al. (1997) Immunol. Cell Biol. 75:364-369; Hertoughs, et al. (2003) Nucleic Acids Res. 31:5817-5830; Trimble, et al. (2003) Vaccine 21:4036-4042; Nishitani, et al. (2000) Mol. Urol. 4:47-50; Tuting (1999) Curr. Opin. Mol. Ther. 1:216-225). Nucleic acid vaccines can be used in combination with reagents that promote migration of immature dendritic cells towards the vaccine, and a reagent that promotes migration of mature DCs to the draining lymph node where priming can occur, where these reagents encompass MIP-1alpha and Flt3L (see, e.g., Kutzler and Weiner (2004) J. Clin. Invest. 114:1241-1244; Sumida, et al. (2004) J. Clin. Invest. 114: 1334-1342).

Bacterial vectors include, for example, *Salmonella*, *Shigella*, *Yersinia*, *Lactobacillus*, *Streptococcus*, Bacille Calmette-Guerin, *Bacillus anthracis*, and *Escherichia coli*. The bacterium can be engineered to contain a nucleic acid encoding a recombinant antigen, a heterologous antigen, or an antigen derived from a tumor, cancer cell, or infective agent. Moreover, the bacterium can modified to be attenuated. In another aspect, the non-listerial bacterial vaccine can be absent of any nucleic acid encoding a recombinant antigen (see, e.g., Xu, et al. (2003) Vaccine 21:644-648; Pasetti, et al. (2003) J. Virol. 77:5209-5219; Loessner and Weiss (2004) Expert Opin. Biol. Ther. 4:157-168; Grangette, et al. (2002) Vaccine 20:3304-3309; Byrd, et al. (2002) Vaccine 20:2197-2205; Edelman, et al. (1999) Vaccine 17:904-914; Domenech, et al. (2005) Microbes and Infection 7:860-866).

Killed but metabolically active ("KBMA") bacteria, and particularly KBMA *Listeria* can be prepared from live bacteria by treatment with a DNA cross-linking agent (e.g., psoralen) and/or by inactivating at least one gene that mediates DNA repair, e.g., a recombinational repair gene (e.g., recA) or an ultraviolet light damage repair gene (e.g., uvrA, uvrB, uvrAB, uvrC, uvrD, phrA, phrB) (see, e.g., U.S. Pat. Publ. Nos. 2004/0228877 and 2004/0197343 of Dubensky, et al., each of which is hereby incorporated by reference herein in its entirety).

One type of KBMA *Listeria* are *Listeria* uvrAB engineered to express a heterologous antigen, where the engineered bacterium is treated with a nucleic acid cross-linking agent, a psoralen compound, a nitrogen mustard compound, 4'-(4-amino-2-oxa)butyl-4,5',8-trimethylpsoralen, or beta-alanine, N-(acridine-9-yl), 2-[bis(2-chloroethyl)amino]ethyl ester. See also, e.g., U.S. Publ. Pat. Appl. No. US 2004/0197343, MODIFIED FREE-LIVING MICROBES, VACCINE COMPOSITIONS AND METHODS OF USE THEREOF, of Dubensky, et al.; Brockstedt, et al (2005) Nature Med. 11:853-860).

In some embodiments, the priming vaccine comprises an agent selected from the group consisting of a vaccinia virus (VV) vector, a dendritic cell (DC) vector, an adenoviral vector, a naked DNA vector, and GVAX.

3. *Listeria* Used in Boosting Vaccines

The invention in some aspects includes the use of a *Listeria* bacterium, where the *Listeria* is attenuated. The attenuation can result from mutating one or more genes encoding a virulence factor, such as actA, internalin B (inlB), p60 (autolysin), listeriolysin O (LLO; hly gene), phosphatidylcholine phospholipase C (PC-PLC), phosphatidylinositol-specific phospholipase C (PI-PLC; plcA gene), lipoate protein ligase, and well as genes disclosed in ENGINEERED LISTERIA AND METHODS OF USE THEREOF, U.S. Ser. No. 11/395,197 (filed Mar. 30, 2006), assigned to Cerus Corporation. The methods of the invention include, but are not limited to, use of one or more of the listerial species and strains identified therein. For example, the invention encompasses the use of a Listeria bacterium that is, or is derived from, Listeria monocytogenes. Also useful are other species of Listeria, such as L. innocua that are engineered to express one or more of listeriolysin O (hly gene; LLO), picA, plcB, or other genes such as a virulence gene or gene mediating entry into a host cell (see, e.g., Johnson, et al. (2004) Appl. Environ. Microbiol. 70:4256-4266; Slaghuis, et al. (2004) J. Infect. Dis. 189:393-401; Milohanic, et al. (2003) Mol. Microbiol. 47:1613-1625). The attenuated strains of Listeria suitable for use in the boost vaccines of the invention may be prepared as described in PCT/US2004/003429 and in PCT/US2004/044080. All of the above applications are incorporated by reference herein in their entirety.

Nonlimiting examples of attenuated Listeria are described, e.g., in the following patent publications, each of which is hereby incorporated by reference herein in its entirety: U.S. Patent Publication No. 2004/0228877; U.S. Patent Publication No. 2004/0197343; and U.S. Patent Publication No. 2005/0249748. Nonlimiting examples are also provided, e.g., in U.S. patent application Ser. No. 11/395,197, filed Mar. 30, 2006, which is hereby incorporated by reference herein in its entirety.

4. Vaccine Compositions

In addition to the agents described above, the vaccine compositions of the invention may further comprise various excipients, adjuvants, carriers, auxiliary substances, modulating agents, and the like. A carrier, which is optionally present, is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J P, et al., J Microencapsul. 14(2):197-210, 1997; O'Hagan D T, et al., Vaccine 11(2):149-54, 1993. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from E. coli. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detoxu); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G 129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

5. Preparation of Vaccine Compositions

The vaccines are prepared by methods known to those of skill in the art. Usually, one or more of the agents described above (for use in prime or boost vaccines) are prepared by mixing a desired amount of the agent with a pharmaceutically acceptable excipient. Pharmaceutically acceptable excipients include, but are not limited to, sterile distilled water, saline, phosphate buffered solutions, amino acid-based buffers, or bicarbonate buffered solutions.

6. Vaccine Administration

An effective amount of a priming vector or boosting vector to be supplied in one or multiple doses of a vaccine can be determined by one of skill in the art. Such an amount will fall in a range that can be determined through routine trials.

The prime vaccine and the boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, intratumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

The following may be taken into consideration in determining the relative timing of the prime vaccine and boost vaccine. It has been found that administration of an antigen, or nucleic acid encoding an antigen, can stimulate expansion of antigen-specific immune cells, resulting in a peak, followed by contraction of the number of antigen specific immune cells (see, e.g., Badovinac, et al. (2002) Nature Immunol. 3:619-626). Initiation of the boost vaccination can be administered before the peak is reached, coincident with the peak, or after the peak.

Administration of the boost vaccination can be initiated when a population of antigen-specific immune cells has expanded (increased in number) to at least 20% the maximal number of antigen-specific immune cells that is eventually attained; to at least 30%; to at least 40%; to at least 50%; to at least 60%; to at least 70%; to at least 80%; to at least 90%; to at least 95%; to at least 99% the maximal number of antigen-specific immune cells that is eventually attained. Additional schedules of prime-boost vaccines are available, for example, the boost vaccination can be initiated when the population of antigen-specific cells has contracted to under 90% the maximal number of antigen-specific cells; under 80%; under 70%; under 60%; under 50%; under 40%; under 30%; under 20%; under 10%; under 5%; under 1.0%; under 0.5%; under 0.1%; under 0.05%; or under 0.01% the maximal number of antigen-specific immune cells. The antigen-specific cells can be identified as specific for a vector-specific antigen (specific for empty vector), or specific for a heterologous antigen expressed by a nucleic acid contained in the vector.

In other aspects, administration of the boost vaccination can be initiated at about 5 days after the prime vaccination is initiated; about 10 days after the prime vaccination is initiated; about 15 days; about 20 days; about 25 days; about 30 days; about 35 days; about 40 days; about 45 days; about 50 days; about 55 days; about 60 days; about 65 days; about 70 days; about 75 days; about 80 days, about 6 months, and about 1 year after administration of the prime vaccination is initiated.

The boost vaccination can be administered 5-10 days after the prime vaccination; 10-15 days after the prime vaccination; 15-20 days after the prime vaccination; 20-25 days after the prime vaccination; 25-30 days after the prime vaccination; 30-40 days after the prime vaccination; 40-50 days after the prime vaccination; 50-60 days after the prime vaccination; 60-70 days after the prime vaccination; and so on.

The period of time between initiation of the prime vaccination and initiating the boost vaccination can be determined by one of skill in the art. For example, it can be based on an algorithm that is sensitive to physiologic parameters measured after the prime immunization has occurred.

The dosage and regimen will be determined, at least in part, be determined by the potency of the modality, the vaccine delivery employed, the need of the subject and be dependent on the judgment of the practitioner.

For example, the *Listeria* in the vaccines used in the invention can be administered in a dose, or dosages, where each dose comprises between $10^7$ and $10^7$ *Listeria* per 70 kg body weight; $2\times10^7$ and $2\times10^8$ *Listeria* per 70 kg body weight; $5\times10^7$ and $5\times10^8$ *Listeria* per 70 kg body weight; $10^8$ and $10^9$ *Listeria* per 70 kg body weight; between $2.0\times10^8$ and $2.0\times10^9$ *Listeria* per 70 kg; between $5.0\times10^8$ to $5.0\times10^9$ *Listeria* per 70 kg; between $10^9$ and $10^{10}$ *Listeria* per 70 kg; between $2\times10^9$ and $2\times10^{10}$ *Listeria* per 70 kg; between $5\times10^9$ and $5\times10^{10}$ *Listeria* per 70 kg; between $10^{11}$ and $10^{12}$ *Listeria* per 70 kg; between $2\times10^{11}$ and $2\times10^{12}$ *Listeria* per 70 kg; between $5\times10^{11}$ and $5\times10^{12}$ *Listeria* per 70 kg; between $10^{12}$ and $10^{13}$ *Listeria* per 70 kg; between $2\times10^{12}$ and $2\times10^{13}$ *Listeria* per 70 kg; between $5\times10^{12}$ and $5\times10^{13}$ *Listeria* per 70 kg; and so on, wet weight. Also provided are each of the above doses, based in a per 1.7 square meters surface area basis, or on a 1.5 kg liver weight basis. It is to be noted that a mouse liver, at the time of administering the *Listeria* of the invention, weighs about 1.5 grams. Human liver weighs about 1.5 kilograms.

In some embodiments of the invention the boost dose of *Listeria* will enhance the prime dose immune response by at least two-fold, at times between about three- and five-fold or five-fold to ten-fold, or from ten-fold to 100-fold or greater. In some embodiments of the invention the prime dose and boost dose will have a synergistic effect on the immune response. In some embodiments of the invention the enhanced immune response will include a T-cell response, and in some embodiments the T-cell response will be a CD8+ T-cell response. In some embodiments of the invention the prime dose and boost dose will break the mammal's tolerogenic state towards the target antigen. Examples of all of these embodiments are provided below.

7. Methods of Measuring Immune Response

A variety of in vitro and in vivo assays are known in the art for measuring an immune response, including measuring humoral and cellular immune responses, which include but are not limited to standard immunoassays, such as RIA, ELISA assays; intracellular staining; T cell assays including for example, lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. (1993) 151:4189-4199; Doe et al., Eur. J. Immunol. (1994) 24:2369-2376. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J., and O'Callaghan, C. A., J. Exp. Med. 187(9)1367-1371, 1998; Mcheyzer-Williams, M. G., et al., Immunol. Rev. 150:5-21, 1996; Lalvani, A., et al., J. Exp. Med. 186:859-865, 1997). In illustrative embodiments disclosed herein, the enzyme-linked immunospot (ELISPOT) assay is used to detect and analyze individual cells that secrete interferon-γ (IFN-γ). ELISPOT IFN-γ assays and reagents are available at BD Biosciences 2350 Qume Drive San Jose, Calif., 95131. The ELISPOT assay is capable of detecting cytokine producing cells from both activated naïve and memory T-cell populations and derives its specificity and sensitivity by employing high affinity capture and detection antibodies and enzyme-amplification. Additional information regarding the use of ELISPOT assay is provided in J.

Immunol. Methods. 2001, 254(1-2):59. Animal models, e.g. non-human primates, are known in the art. For example, the mouse is an accepted model for human immune response. Mouse NK cell response to tumors is an accepted model for human NK cell response to tumors. Additionally, mouse T cells are a model for human T cells, mouse dendritic cells (DCs) are a model for human DCs, mouse NKT cells are a model for human NKT cells, mouse innate response is an accepted model for human innate response, and so on. Model studies are disclosed, for example, for CD8+ T cells, central memory T cells, and effector memory T cells (see, e.g., Walzer, et al. (2002) J. Immunol. 168:2704-2711); the two subsets of NK cells (see, e.g., Chakir, et al. (2000) J. Immunol. 165:4985-4993; Smith, et al. (2000) J. Exp. Med. 191:1341-1354; Ehrlich, et al. (2005) J. Immunol. 174: 1922-1931; Peritt, et al. (1998) J. Immunol. 161:5821-5824); NKT cells (see, e.g., Couedel, et al. (1998) Eur. J. Immunol. 28:4391-4397; Sakamoto, et al. (1999) J. Allergy Clin. Immunol. 103:S445-S451; Saikh, et al. (2003) J. Infect. Dis. 188:1562-1570; Emoto, et al. (1997) Infection Immunity 65:5003-5009; Taniguchi, et al. (2003) Annu. Rev. Immunol. 21:483-513; Sidobre, et al. (2004) Proc. Natl. Acad. Sci. 101:12254-12259); monocytes/macrophages (Sunderkotter, et al. (2004) J. Immunol. 172:4410-4417); the two lineages of DCs (Boonstra, et al. (2003) J. Exp. Med. 197:101-109; Donnenberg, et al. (2001) Transplantation 72:1946-1951; Becker (2003) Virus Genes 26:119-130; Carine, et al. (2003) J. Immunol. 171:6466-6477; Penna, et al. (2002) J. Immunol. 69:6673-6676; Alferink, et al. (2003) J. Exp. Med. 197:585-599). Mouse innate response, including the Toll-Like Receptors (TLRs), is a model for human innate immune response, as disclosed (see, e.g., Janssens and Beyaert (2003) Clinical Microb. Revs. 16:637-646). Mouse neutrophils are an accepted model for human neutrophils (see, e.g., Kobayashi, et al. (2003) Proc. Natl. Acad. Sci. USA 100:10948-10953; Torres, et al. (2004) 72:2131-2139; Sibelius, et al. (1999) Infection Immunity 67:1125-1130; Tvinnereim, et al. (2004) J. Immunol. 173:1994-2002). Murine immune response to *Listeria* is an accepted model for human response to *Listeria* (see, e.g., Kolb-Maurer, et al. (2000) Infection Immunity 68:3680-3688; Brzoza, et al. (2004) J. Immunol. 173:2641-2651).

8. Uses of the Prime-Boost Regimen

Cancers and infections can be treated and/or inhibited by administering reagents that modulate the immune system. The prime-boost methods encompassed within the invention give rise to immune responses that are upregulated, and include breaking tolerance to self-antigens. Thus, it is expected that these prime-boost methods will be useful in inhibiting the growth of cancers and/or ameliorating one or more symptoms associated with a cancer. It is also expected that the prime-boost methods will be useful in the prophylaxis and/or treatment of a disease caused by a pathogenic agent.

In addition to the above, these regimens can be used to determine whether a mammal will be responsive to a treatment. For example, when a prime-boost regimen towards a specific antigen is used, failure to obtain a significant immune response after the boost suggests that the mammal is non-responsive towards the target antigen and an alternative mode of treatment should be pursued. Examples of this could be when the genetic background of the cancer or pathogenic agent is such that the target antigen is absent or modified in a way that it is not cross-reactive with the target antigen.

EXAMPLES

It is to be understood that this invention is not limited to particular examples disclosed herein, as such may vary. It is also to be understood that the examples are not intended to be limiting since the scope of the present invention is delineated by the appended claims.

General Information on Methods Used in the Examples

Immune responses to vaccines were assessed by harvesting splenocytes, a source that provides cells of the immune system, including T cells and dendritic cells (DCs). Antigen-specific immune responses were measured by incubating splenocytes with one or more peptides and measuring immune cell activity, where activity was determined by intracellular staining (ICS) and elispot assays. In some assays, only a single peptide was added, where the peptide contained only one epitope of a tumor antigen. In other assays, an entire library of peptides was added, encompassing the entire length of the antigen.

ICS assays involve permeabilizing the splenocytes, and treating with an antibody that binds cytokines that have accumulated inside the immune cell, where the antibody allows fluorescent tagging. Brefeldin blocks protein transport, and provokes the accumulation of cytokines within the immune cell.

Elispot (enzyme-linked immunospot) assays are sensitive to secreted proteins, where the proteins are secreted over a period of time from immune cells resting in a well. A capture antibody is bound to the well, which immobilized secreted cytokine. After the secretory period, the cells are removed, and a detection antibody is used to detect immobilized cytokine. The capture antibody and detection antibody bind to different regions of the cytokine. Methodological details of the ICS and elispot assays are disclosed (see, e.g., U.S. Pat. Appl. Pub. No. 2005/0249748, published Nov. 10, 2005, of Dubensky, et al.).

Where the administered vector contained a nucleic acid encoding ovalbumin, analysis of any induced immune response by way of ICS assays or elispot assays used a standard peptide from ovalbumin, $OVA_{257-264}$ (SIINFEKL (SEQ ID NO:1)), where the peptide was added to and incubated with the splenocyte preparation.

The nucleic acid sequence of human Mesothelin, used in the following constructs, was that identified in ENGINEERED *LISTERIA* AND METHODS OF USE THEREOF, U.S. Ser. No. 11/395,197, filed Mar. 30, 2006, assigned to Cerus Corporation. The Mesothelin peptide library, which spanned the entire length of human Mesothelin, consisted of 153 peptides, each a 15-mer, with each 15-mer overlapping the next 15-mer by eleven amino acids.

Lm-hMeso38, a construct of *Listeria monocytogenes* used in the following examples, is identified in Table 1. See also, ENGINEERED *LISTERIA* AND METHODS OF USE THEREOF, U.S. Ser. No. 11/395,197, filed Mar. 30, 2006. Lm-mMeso is the same construct as Lm-hMeso38 except that the full length human Mesothelin sequence is substituted with the full length mouse Mesothelin sequence. The full length mouse sequence is available from GenBank Acc. No. NM_018857.

TABLE 3

Listeria monocytogenes-hMeso38 (Lm-hMeso38).

| Strain (trivial name) | Construct | Genetic background | Locus of integration | Promoter operably linked in antigen expression cassette | Secretory sequence (SS) |
|---|---|---|---|---|---|
| Lm-hMeso38 | ActA-N100-hmeso [deltaSS]. The human Mesothelin sequence was deleted in its signal sequence, but was not deleted in its GPI anchor. "ActA-N100" is the first 100 amino acids of ActA, where the first 29 of these amino acids is the signal sequence. | ΔactAΔinlB | inlB | ActA | ActA-N100 |

The preparation of Listeria monocytogenes encoding OVA ("Lm-OVA") was as discussed in U.S. Patent Publication No. 2004/0197343, (U.S. Ser. No. 10/773,618).

The vaccinia virus-derived vector (VV-OVA), which contains a nucleic acid encoding full-length ovalbumin, was prepared and provided by N. P. Restifo, as described (Overwijk, et al. (1998) J. Exp. Med. 188:277-286).

The adenovirus-based vectors contained a nucleic acid encoding full-length human Mesothelin or full-length mouse Mesothelin (Ad-hMeso or Ad-mMeso). Control Ad vectors not encoding a heterologous antigen, otherwise known as "Empty Ad vector" were also used. All control and antigen-encoding Ad vectors were based on adenovirus serotype 5 with E1 and E3 regions deleted, and were derived utilizing the "AdEasy" system obtained from Stratagene (San Diego, Calif.) and derived according to the Methods described by the supplier. Antigens were cloned at the E1 locus. The nucleic acid encoding the heterologous antigen was integrated into the shuttle vector of AdEasy in operable linkage with the CMV promoter.

GVAX refers to an inactivated tumor cell containing a nucleic acid that encodes mouse granulocyte macrophage-colony stimulation factor (GM-CSF), where the tumor cell line was CT-26 cells, a cell line that expresses the gp70. AH1 is an epitope of gp70, an immunodominant antigen of CT26 cells. GVAX was prepared and administered as disclosed (see, e.g., Yoshimura, et al. (2006) Cancer Res. 66:1096-1104; Jain, et al. (2003) Annals Surgical Oncol. 10:810-820; Zhou, et al. (2005) Cancer Res. 65:1079-1088; Chang, et al. (2000) Int. J. Cancer 86:725-730; Borrello and Pardoll (2002) Cytokine Growth Factor Rev. 13:185-193; Thomas, et al. (1998) Human Gene Ther. 9:835-843).

Killed but metabolically active Lm ("KBMA-Lm"), were prepared by treating live Lm deleted of the uvrAB genes, whose expression in combination with the uvrC gene product forms the exonuclease required for nucleotide excision repair, with psoralen and ultraviolet light, resulting in a small amount of cross-linking of the genome (see, e.g., U.S. Ser. No. 10/773,618. Pub. No. US 2004/0197343. MODIFIED FREE-LIVING MICROBES, VACCINE COMPOSITIONS AND METHODS OF USE THEREOF, of Dubensky, et al.; Brockstedt, et al. (2005) Nature Med. 11:853-860).

Example 1

C57BL/6 mice (3 per group) were immunized on day 0 with either $1\times10^6$ pfu of vaccinia virus ("VV") encoding OVA or with $5\times10^6$ cfu of recombinant Listeria monocytogenes ("Lm") deleted of the actA and inlB virulence determinants and encoding OVA. On day 21 the mice received a boost dose of either the VV or Lmat doses that in each case were equivalent to the priming immunization doses. The mice were sacrificed and splenocytes harvested on day 27. To assess the magnitude of vaccine-induced OVA-specific CD8+ T cells after a single immunization, control mice received only a single immunization with VV or Lm on day 20 and were sacrificed and splenocytes harvested on day 27. OVA specific CD8+ T cell responses were determined using $OVA_{257-264}$ peptide in ISC assays.

The OVA specific CD8+ T cell immune responses resulting from the prime-boost regimens are shown in FIG. 1A. As seen in the figure, a prime-boost regimen utilizing a VV prime/Lm boost yields almost a doubling in the percentage of OVA specific $CD8^+$ cells when compared to an LM prime/VV boost. In addition the percentage of OVA specific CD8 cells in the VVprime/Lm boost is about 3 fold higher than a homologous Lm prime/Lm boost, and about 9 fold higher than a homologous VV prime/VV boost. This data provides evidence of directionality in the heterologous prime-boost regimen, with superior results obtained from a system that uses an Lm boost.

Example 2

Balb/c mice with 3 mice per group were injected on day 0 with either $3\times10^7$ pfu adenovirus ("AV" or "adeno-hMeso") encoding human Mesothelin or with $5\times10^6$ cfu LmΔactA/ΔinlB encoding human Mesothelin ("Lm-hMeso38"). On day 21 the mice received a boost dose of either the AV or Lm-hMeso38 at doses that in each case were equivalent to the priming immunization doses. The mice were sacrificed and splenocytes harvested on day 27. To assess the magnitude of vaccine-induced OVA-specific CD8+ T cells after a single immunization, control mice received only the AV and Lm-hMeso38 on day 20 and were sacrificed and splenocytes harvested on day 27.

Figure 1B:
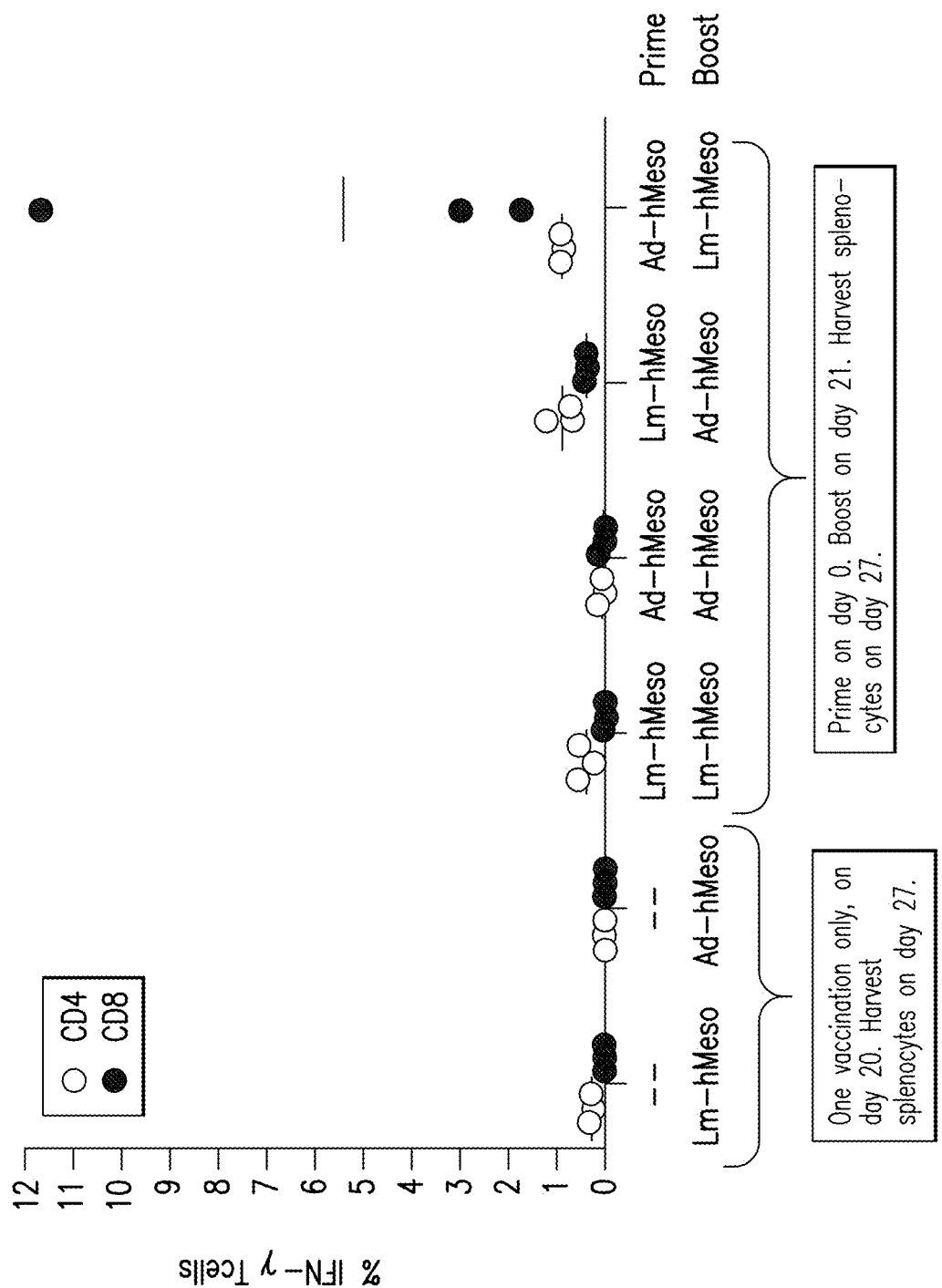
FIG. 1B is a graph showing human Mesothelin-specific cellular immune responses resulting from prime-boost regimens using *Listeria monocytogenes* and Adenovirus expressing the target antigen (human Mesothelin).

The vaccine-induced human Mesothelin specific CD4+ and CD8+ cellular immune responses resulting from the prime-boost regimens are shown in FIG. 1B. The AV prime/Lm-hMeso38 boost yielded about a 10-fold higher magnitude of the percentage of splenic CD8+ cells specific for human Mesothelin) "hMeso") when compared to the cohort of mice given an Lm prime/AV boost regimen, demonstrating both that the directionality in the heterologous boosting regimen affects the magnitude of the vaccine-induced cellular immunity specific for the encoded antigen, and that superior results are obtained from a system that uses an Lm boost.

Example 3

Figure 2:
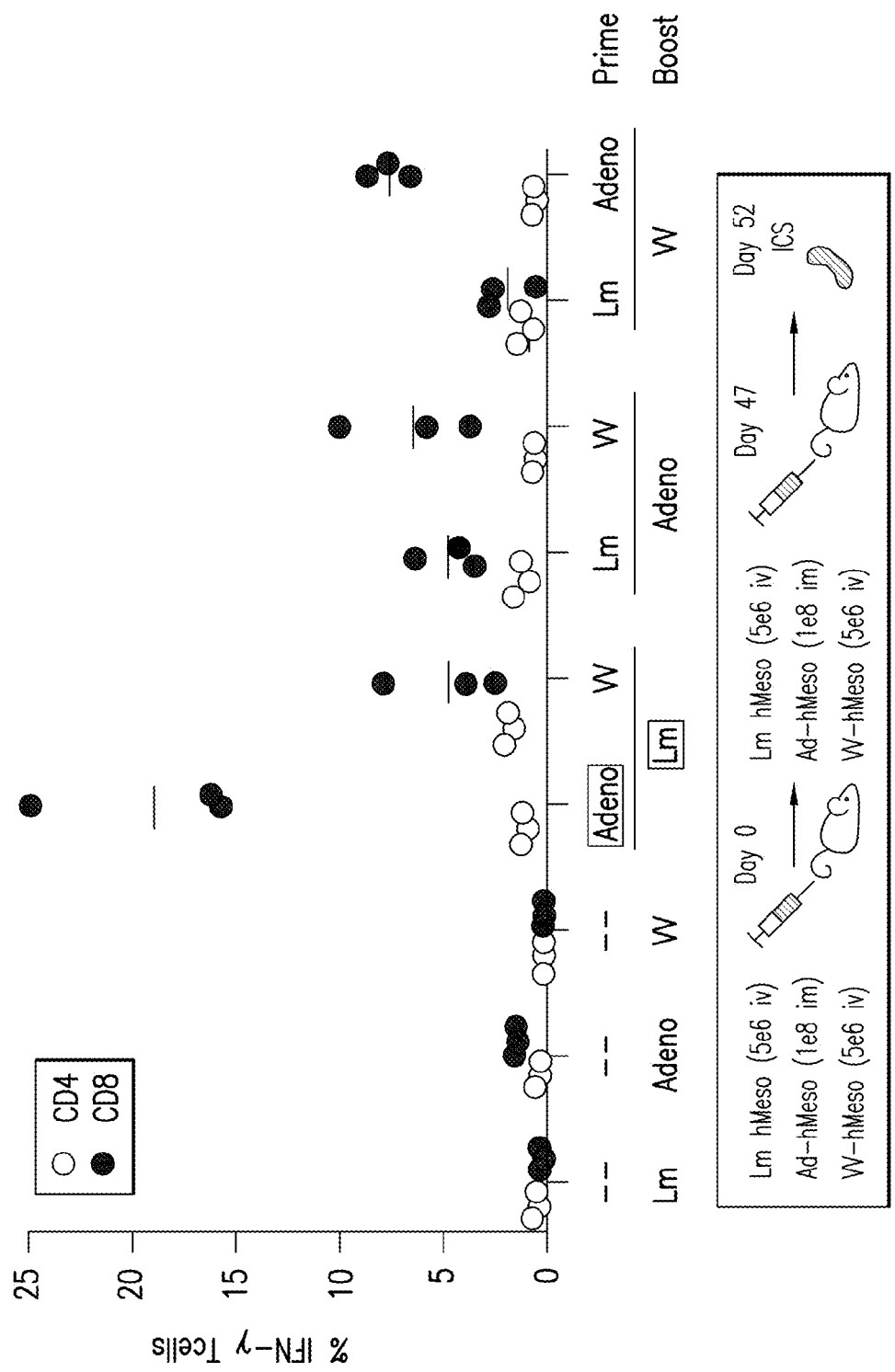
FIG. 2 is a graph showing human Mesothelin-specific cellular immune responses in Balb/c mice resulting from prime-boost regimens using *Listeria monocytogenes*, Adenovirus and Vaccinia virus. The prime-boost regimens are also illustrated.

Balb/c mice (3 per group) received priming doses and boosting doses to provoke an immune response against human Mesothelin. The priming and boosting regimen was as indicated in FIG. 2 using the indicated vectors that all encoded human Mesothelin. As seen from the results of the ICS assays, a regimen of AV prime/Lm boost yielded a 3 to 4 fold higher percentage of human Mesothelin ("hMeso") specific CD8+ cells than did an Lm prime/AV boost. In addition, the results in FIG. 2 also show that the AV prime/Lm boost was significantly higher than any of the other heterologous prime-boost regimens tested.

Example 4

Figure 3A:
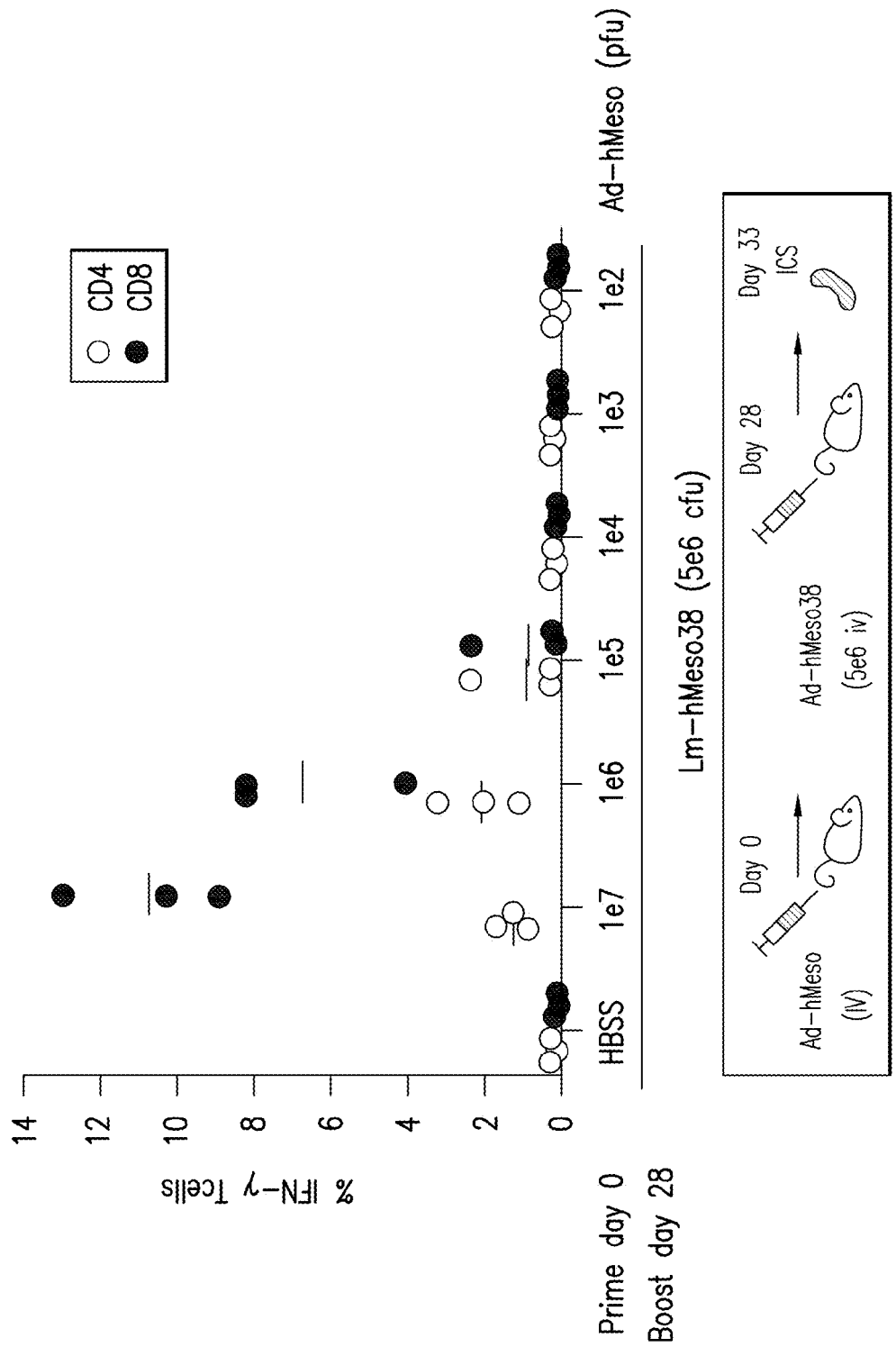
FIG. 3A is a graph showing the human Mesothelin-specific cellular immune responses in CS7BL/6 (HLA-A2 transgenic) mice resulting from prime-boost regimens using increasing levels of Adenovirus prime and a constant level of *Listeria monocytogenes* boost. (Splenocytes were stimulated with mesothelin peptide pool.) The prime-boost regimens are also illustrated.

The effect of different AV priming doses against a constant Lm boost in the heterologous AV prime/Lm boost on the magnitude of vaccine-induced splenic hMeso-specific CD4+ and CD8+ T cell immunity was tested. All the vectors encoded human Mesothelin. HBSS was used as a control. The prime and boost regimen utilized was as indicated in FIG. 3A, with each experimental cohort consisting of three C57BL/6 mice. In these studies, the splenocytes obtained from the immunized mice were stimulated for 5 hours with a Mesothelin peptide pool library consisting of peptides 15 amino acids long offset by 4 amino acids ("15×11 library") corresponding to the full-length Mesothlin protein prior to ICS. The human Mesothelin specific cellular immune responses resulting from the titration of AV in the prime-boost regimens are shown in FIG. 3A. As seen in the figure, significant enhancement of specific T cell responses was obtained at the higher amounts of AV, and the CD8+ Tcell response was greater than that of CD4+.

Example 5

Figure 3B:
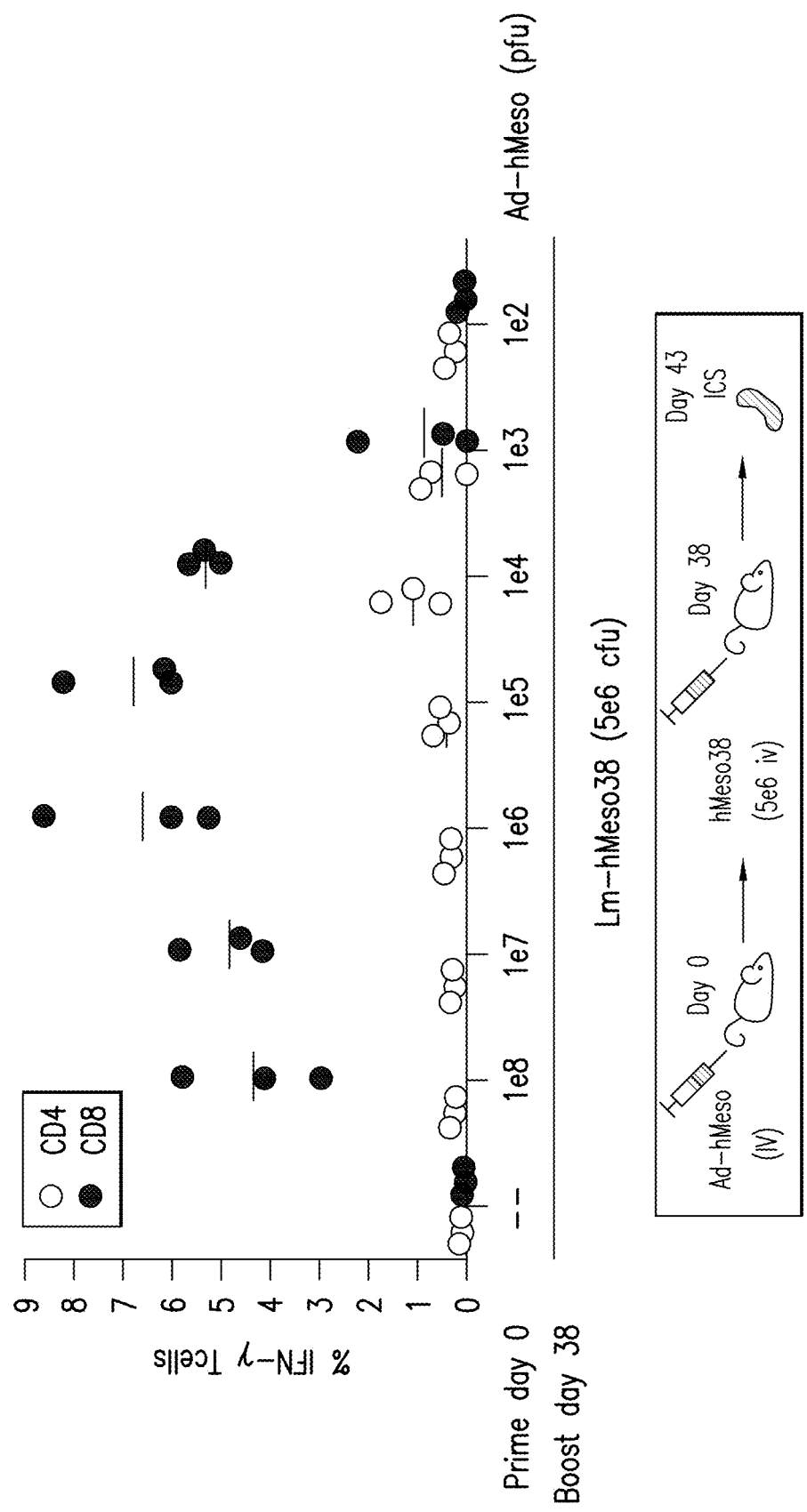
FIG. 3B the human Mesothelin-specific cellular immune responses in Balb/c mice resulting from prime-boost regimens using increasing levels of Adenovirus prime and a constant level of *Listeria monocytogenes* boost. (Splenocytes were stimulated with mesothelin peptide pool.) The prime-boost regimens are also illustrated.

An immunization protocol similar to that used in Example 4 was used in Balb/c mice (See FIG. 3B), except that the time between the prime and the boost was 38 days, and control mice were immunized with Lm hMeso 38, but not primed with AV. As seen in FIG. 3B, the significant enhancement of specific T cell responses were over a greater range of AV amounts, and again, the CD8+ Tcell response was greater than that of CD4+. In Balb/c mice, at AV priming doses as low as $1\times10^4$ pfu substantial levels of hMeso-specific CD8+ T cells were induced after boosting with $5\times10^6$ cfu of Lm hMeso 38.

Example 6

The effectiveness of an AV prime/Lm boost in the presence of pre-existing immunity to AV was tested. In the first study, the responsiveness to AV immunization in the presence of pre-existing adenovirus-specific immunity was tested using the protocol shown in FIG. 4A. Pre-existing adenovirus specific immunity was elicited by immunizing mice with various levels of "empty Ad vector" as shown in the FIG. 28 days prior to immunization with AV encoding human Mesothelin. The study used 5 Balb/C mice per group. The mice were injected on day 0 with either empty Ad particles and subsequently, on day 28 with AV encoding human Mesothelin ("Ad-hMeso"). Splenocytes were harvested on day 35 and used in ICS assays. The Ad-empty and Ad-hMeso vectors were both serotype 5. Mesothelin specific immune response was measured by stimulating splenocytes with human Mesothelin peptide pool; AV specific responses were measured using the class I Hex3 epitope. The results shown in FIG. 4A indicate that in the presence of pre-existing Ad5-specific cellular immunity only a low hMeso specific response could be induced when mice were immunized with the same Ad5 vector encoding human Mesothelin.

Figure 4A:
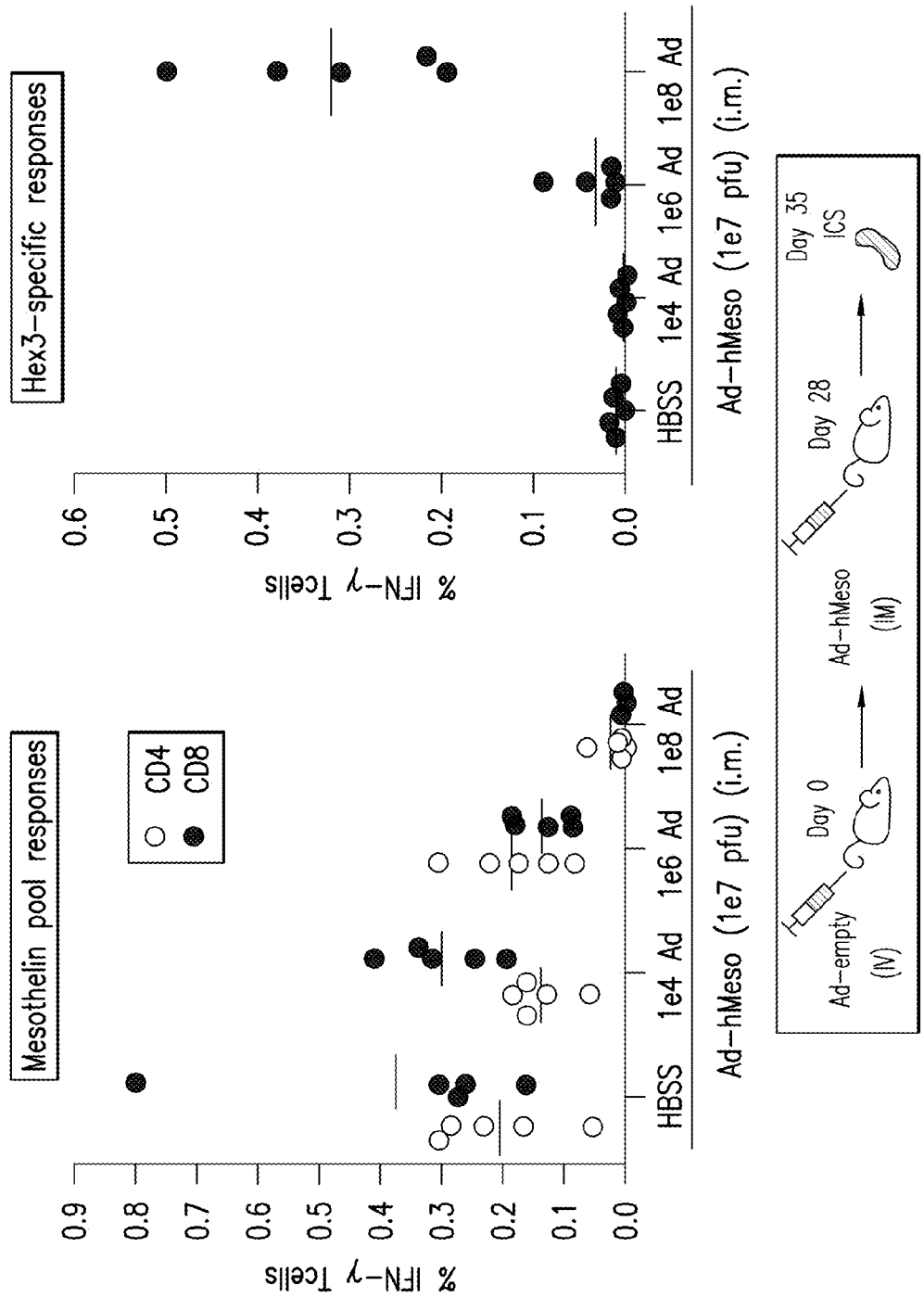
FIG. 4A shows on the left a graph showing the human Mesothelin-specific cellular immune response resulting from an adenovirus prime in mice with a pre-existing immunity to adenovirus. Also shown in FIG. 4A (on the right) are the adenovirus-specific responses as measured using the class I Hex3 epitope (an adenovirus-specific epitope). The prime-boost regimens are also illustrated.
Figure 4B:
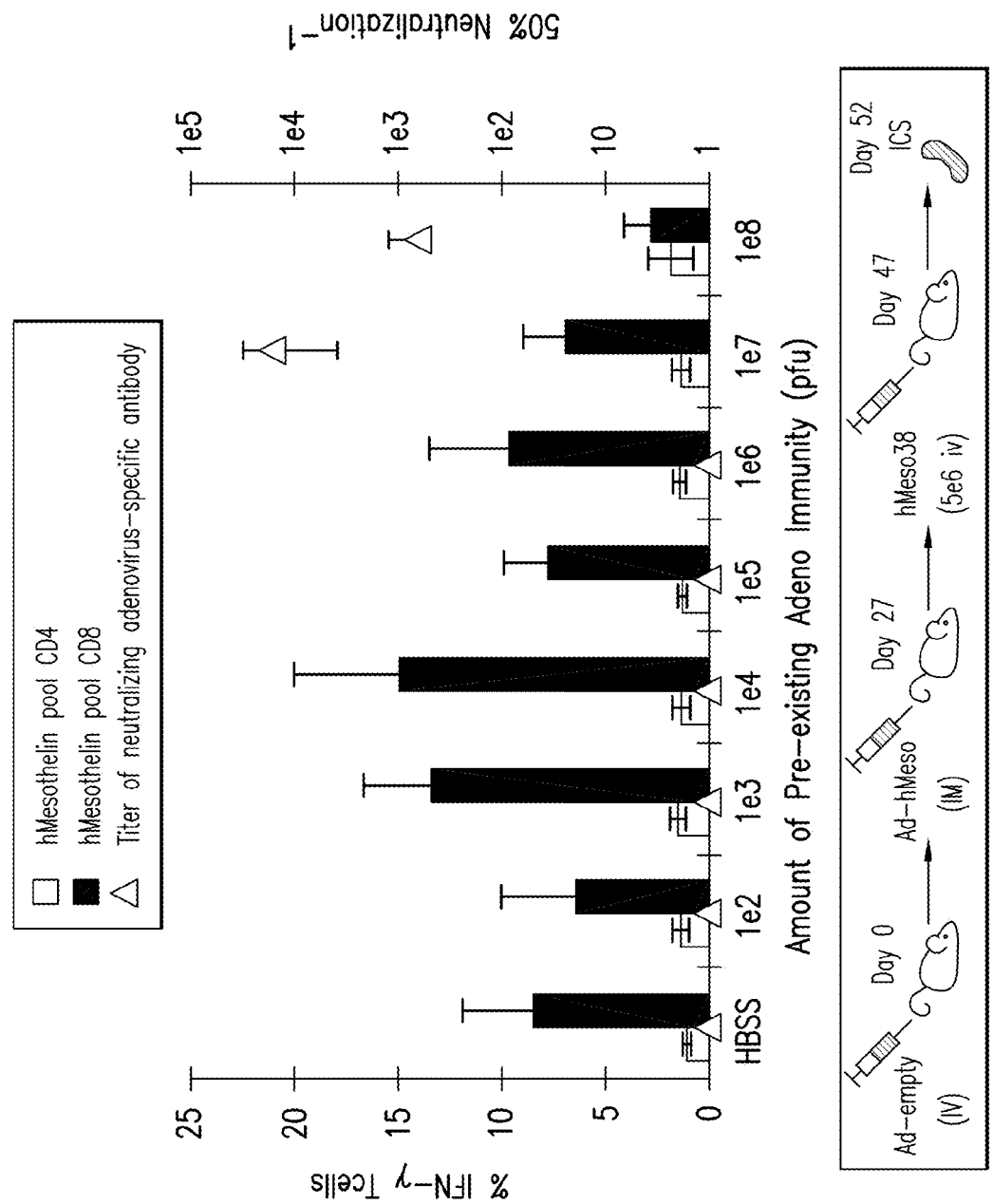
FIG. 4B. is a graph showing the human Mesothelin specific cellular immune response and the titer of neutralizing adenovirus-specific antibodies resulting from an Adenovirus prime and *Listeria monocytogenes* boost in mice with a pre-existing immunity to Adenovirus. The prime-boost regimens are also illustrated.
Figure 5:
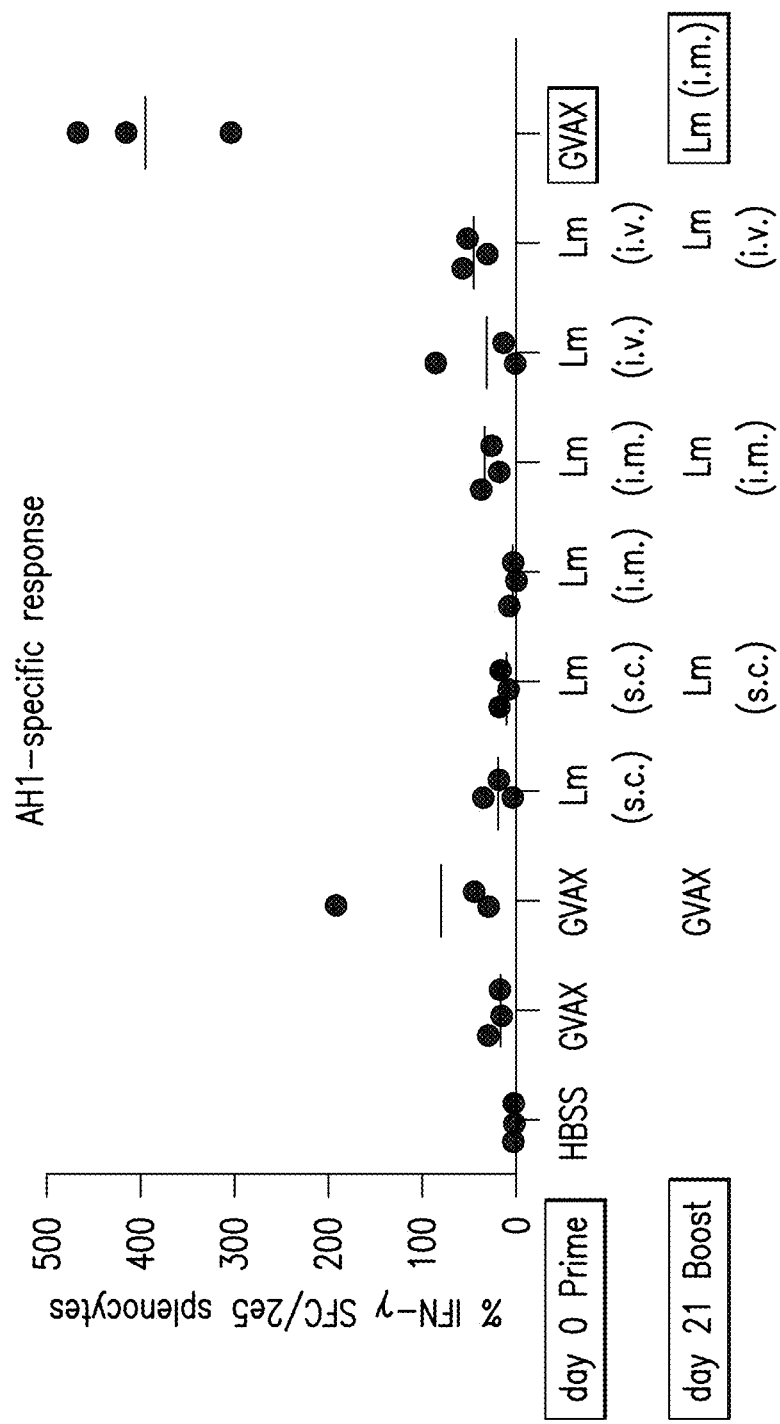
FIG. 5 is a graph showing AH1-specific cellular immune response resulting from a prime with either GVAX or *Listeria monocytogenes* encoding AH1 and a boost with either GVAX or the *Listeria monocytogenes* encoding AH1.

The second study tested the hMeso specific cellular immune response after an AVprime/Lm boost regimen in mice that had pre-existing AV immunity (shown as amount of AV pfu administrated on the X-axis of FIG. 4B). The protocol used (shown in FIG. 4B) was similar to that to test the prime, except that 20 days after the prime with AV, the mice were given a boost with Lm-hMeso38, and instead of measuring AV specific T cell immune response, AV-specific neutralizing antibodies were determined by plaque reduction assay. The results in FIG. 4B when compared to FIG. 4A show that despite the existence of pre-existing neutralizing immunity to AV serotype5, that combining a boost of Lm hMeso38 following an AV prime resulted in the induction of a significant increase in hMeso specific cellular immunity.

Example 7

A heterologous prime-boost using a tumor cell prime/Lm boost was performed as follows. The regimen used GVAX prime/Lm-AH1-A5 boost. "GVAX" refers to an inactivated tumor cell containing a nucleic acid that encodes granuclocyte macrophage-colony stimulation factor (GM-CSF). The administered *Listeria monocytogenes* was Lm-ΔactA-OVA-AH1-A5. Lm-ΔactA-OVA-AH1-A5 is a recombinant *Listeria monocytogenes*, attenuated by a deletion in the actA gene, and containing a single copy of an antigen expression cassette in the listerial genome, integrated at the tRNA$^{Arg}$ locus, where the expression cassette contains the AH1-A5 inserted in-frame within ovalbumin (Brockstedt, et al. (2004) Proc. Natl. Acad. Sci. USA 101:13832-13837). AH1-A5, is the altered T cell ligand of the AH1 $L^d$ immunodominant epitope of the gp70 endogenous rejection antigen expressed by the CT26 adenocarcinoma cell line, and is conventionally used in studies of immune response to the tumor antigen, gp70 (Slansky, et al. (2000) Immunity 13:529-538; Jain, et al. (2003) Annals Surgical Oncol. 10:810-820).

For the heterologous prime/boost. 3 mice in each group received GVAX ($1\times10^6$ cells) (s.c.) as a prime and Lm-OVA-AH1-A5 ($5\times10^6$ cfu) (i.v.) as a boost. For homologous prime/boost vaccines with GVAX, mice received a GVAX prime ($1\times10^6$ cells) (s.c.), for both the prime and boost. For homologous prime/boost vaccines with Lm only, mice were given Lm-OVA-AH1-A5 ($5 \times 10^6$ cfu) (i.v.), for both the prime and boost. Separate homologous prime/boost trials were conducted, where Lm was only administered s.c., i.m., or i.v. In all cases, the prime was administered at t=0 days, boost at t=21 days, with harvest of splenocytes at t=29 days. Mice were also treated with single-administration monovaccines (GVAX only; Lm-OVA-AH1-A5 only), as indicated in the figure.

The results demonstrate that GVAX prime followed by an Lm-ΔactA-OVA-AH1-A5 boost elicited greater AHi-specific immune responses than any homologous prime/boost immunization regimen by any of the routes of administration.

Example 8

A comparison of AV prime/Lm boost with dendritic cell ("DC") prime/Lm boost was performed as follows. Balb/c mice. 5 mice per group, were used. Dendriti cells were administered in the quantity of $2 \times 10^6$ dendritic cells (i.v.). Adenovirus-derived vector containing a nucleic acid encoding human Mesothelin was administered at a dose of $1 \times 10^8$ cfu (i.m.). Lm-hMeso38 was administered in the quantity of $5 \times 10^6$ cfu (i.v.). Peptide-pulsed DCs were administered at a dose of $2 \times 10^6$ DC (i.v.). DC and Lm prime and boost immunizations were separated by 8 days, and AV and Lm prime and boost immunization were separated by 14 days. In all mice, the splenic Mesothelin 131-139 specific CD8+ T cells were measured by days following the boost immunization with Lm hMeso 38. Controls were a indicated in FIG. 6A and FIG. 68.

Peptide-pulsed DCs were prepared as follows. The DCs were pulsed with hMeso$_{131-139}$ (SGPQACTRF) (SEQ ID NO: 5). DC were prepared from whole bone marrow of Balb/c mice using high GM-CSF concentrations (20 ng/mL murine GM-CSF) (R&D Systems, Minneapolis, Minn.). On day 8 following initial plating and GM-CSF enrichment, non-adherent cells were harvested and verified phenotypically to be myeloid dendritic cells (CD11c$^{hi}$). The DCs were treated with lipopolysaccharide (LPS) (24 h) and pulsed with 1.0 micromolar peptide (hMeso$_{131-139}$) (0.001 mM) for 1 hour. Peptide-loaded DCs were washed two times, before injecting $1 \times 10^6$ DCs into recipient Balb/c mice.

Figures 6A, 6B:
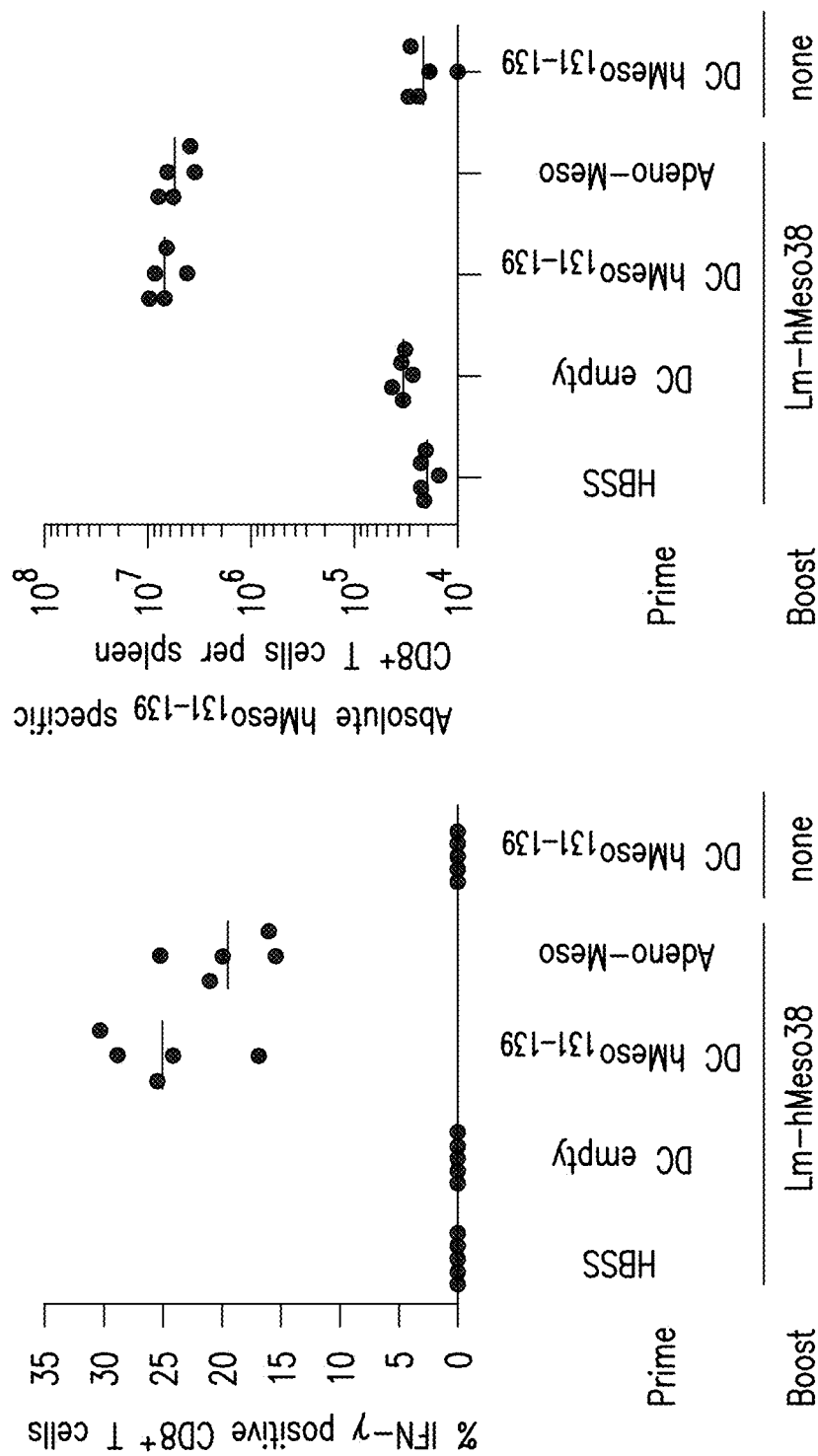
FIG. 6A is a graph showing the percent of $Mesothelin_{131-139}$ specific response among $CD8^+$ T cells resulting from a prime with dendritic cells pulsed with Mesothelin peptide 131-139 or Adenovirus encoding human Mesothelin and boosted with *Listeria monocytogenes* encoding human Mesothelin. Prime occurred on day 0, boost occurred on day 8, and splenocytes were harvested on day 13.
FIG. 6B is a graph showing the absolute number of $Mesothelin_{131-139}$ specific $CD8^+$ T cells per spleen resulting from a prime with dendritic cells pulsed with Mesothelin peptide 131-139 or Adenovirus encoding human Mesothelin and boosted with *Listeria monocytogenes* encoding human Mesothelin. Prime occurred on day 0, boost occurred on day 8, and splenocytes were harvested on day 13.

The results of the JCS assays presented in FIG. 6A demonstrate that heterologous prime/boost with DC-hMeso 131-139 prime/Lm-hMeso38 boost, and heterologous Adeno-hMeso prime/Lm-hMeso38 boost, each induced Mesothelin-specific cellular immune responses, where the level of immune response was about the same for both prime/boost regimens.

The results of Elispot assays, shown in FIG. 6B, demonstrate that heterologous prime/boost with DC-hMeso 131-139 prime/Lm-hMeso38 boost, and heterologous Adeno-hMeso prime/Lm-hMeso38 boost, each induced Mesothelin-specific cellular immune responses, where the level of immune response was about the same for both prime/boost regimens.

Example 9

A comparison of Lm, AV, and VV as a boost after a DC prime was performed as follows. On day 0, Balb/cmice (five per group) were vaccinated intravenously with $1 \times 10^6$ bone marrow-derived dendritic cells (prime). The DC were prepared as described in Example 8. At 21 days, the mice were provided with a boost, where the boost was one of the following: Lm-hMeso38 ($5 \times 10^6$ cfu, i.v.), Ad-hMeso ($1 \times 10^7$ pfu, i.m.) or vaccinia virus-hMeso ("VV-hMeso")($1 \times 10^6$ pfu, i.p.). A separate group of mice received HBSS instead of the boost vaccine. Meso$_{131-139}$-specific CD8+ T cell responses were determined by intracellular cytokine staining (ICS) five days following the boost vaccination.

Figure 6C:
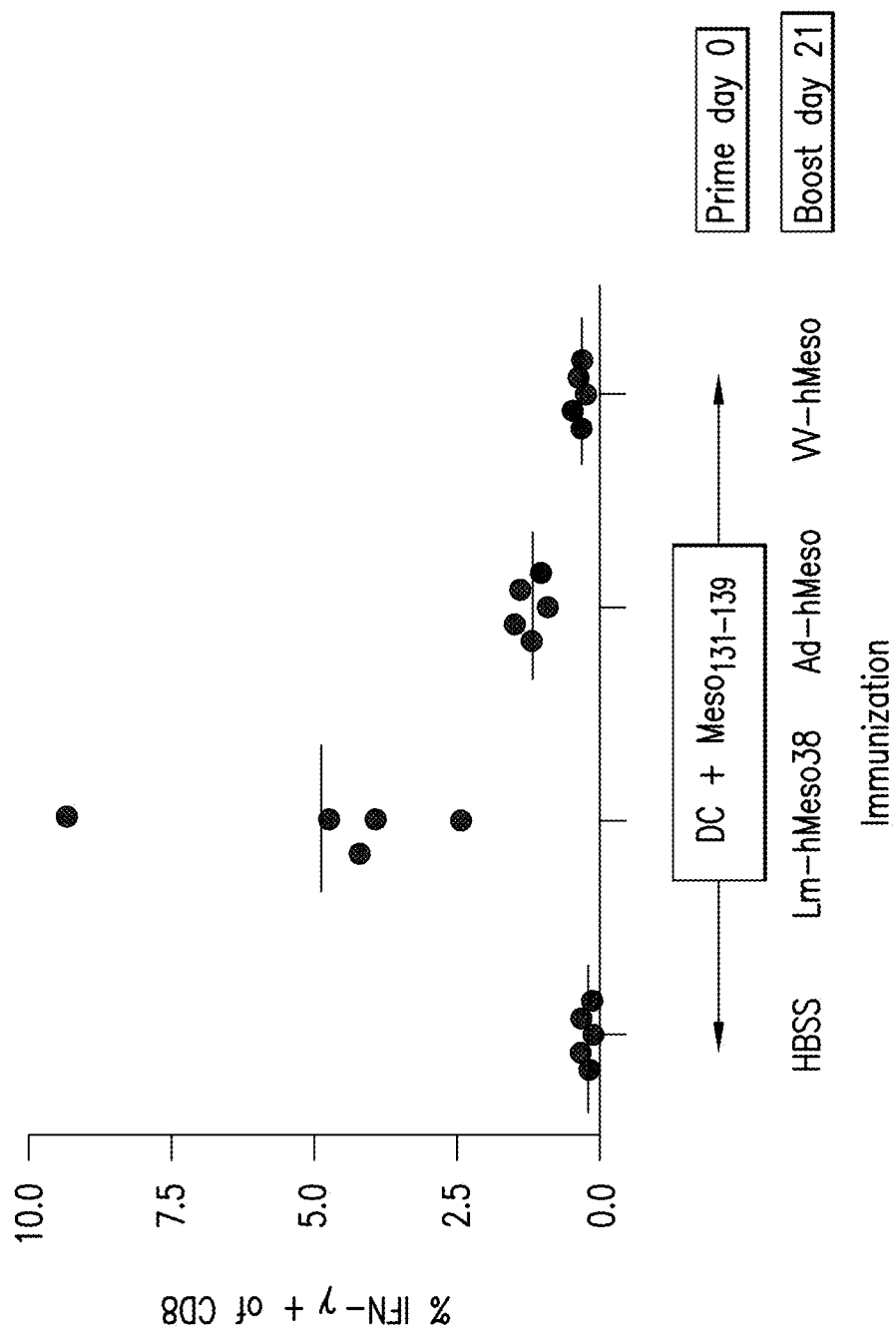
FIG. 6C is a graph showing the percent of $Mesothelin_{13-139}$ specific response among $CD8^+$ T cells resulting from a prime with dendritic cells pulsed with Mesothelin peptide 131-139 and boosted with one of the following Mesothelin encoding agents: *Listeria monocytogenes*, Adenovirus, or Vaccinia virus.

The results shown in FIG. 6C indicate that although the AV-hMeso did give a significant boost to the hMeso cell specific response, approximately a five-fold higher result was achieved using Lm as the boosting agent.

Example 10

Figure 7A:
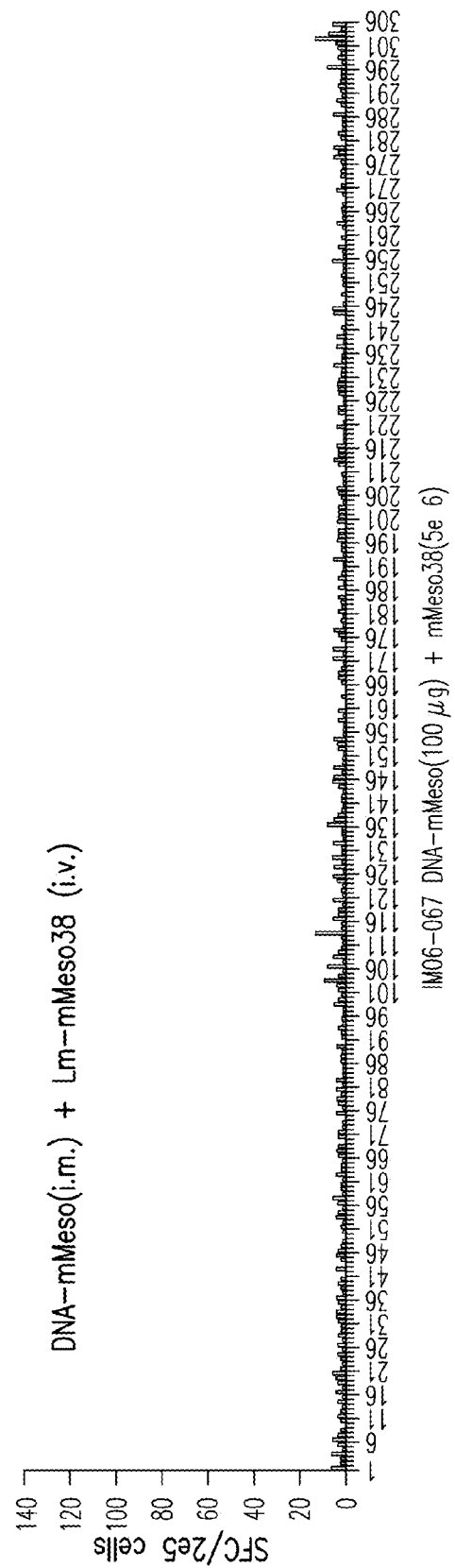
FIG. 7A is a graph showing the mouse Mesothelin specific immune response in splenocytes where the immune response was assessed for each peptide in the mouse Mesothelin peptide library. Balb/c mice received a prime with a naked DNA vector encoding mouse mesothelin, and a boost with *Listeria monocytogenes* encoding mouse Mesothelin.
Figure 7B:
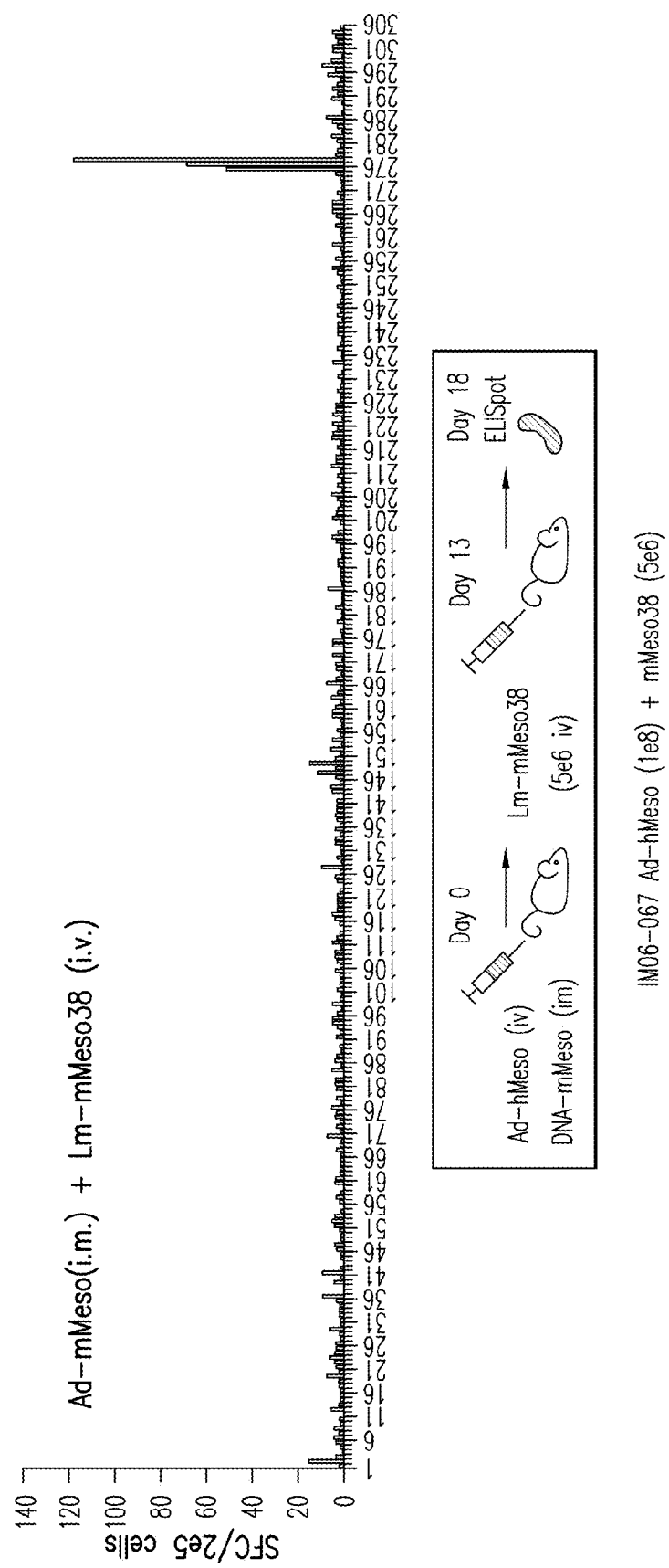
FIG. 7B is a graph showing the mouse Mesothelin specific immune response in splenocytes where the immune response was assessed for each peptide in the mouse Mesothelin peptide library. Balb/c mice received a prime with adenovirus encoding mouse Mesothelin and a boost with *Listeria monocytogenes* encoding mouse Mesothelin. The prime-boost regimens are also illustrated.

A comparison of AV and naked DNA as the prime in a heterologous prime-boost regimen using Lm as the boost was performed. In addition, mouse Mesothelin was substituted for human Mesothelin to determine if it was possible to break tolerance with the heterologous prime-boost regimen. In the study, Balb/c mice were used. Heterologous DNA prime/Lm boost and heterologous Ad prime/Lm boost vaccines were administered, with assessment of Mesothelin-specific immune response using the entire Mesothelin peptide library. The DNA prime/Lm boost was DNA-mMeso (0.1 mg) (i.m.) prime/Lm-mMeso38 ($5 \times 10^6$ cfu) (i.v.) boost (FIG. 7A). The Ad prime/Lm boost was Ad-mMeso ($1 \times 10^8$ pfu) (i.m.) prime/Lm-mMeso38 ($5 \times 10^6$ cfu) (i.v.) boost (FIG. 7B). The naked DNA vector, DNA-mMeso, was prepared as follows. A nucleic acid encoding full length mouse mesothlin was inserted into pCDNA3, a eukaryotic expression vector (Invitrogen Corp., Carlsbad, Calif.).

The prime was administered at day 0, boost at 13 days, with harvest of splenocytes at 18 days. Harvested splenocytes were treated with peptides from the mouse Mesothelin ("mMesothelin") peptide library, where a unique peptide was added to each well containing splenocytes, and where immune response was assessed with Elispot assays. Sufficient wells of splenocytes from immunized mice were utilized such that unique peptides (15 amino acids long, offset by 4 amino acids) covering the full length of the mouse Mesothelin protein could be used, enabling the T cell reactive mouse Mesothein peptides to be identified.

Figure 7C:
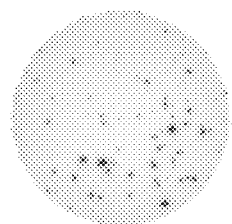
FIG. 7C is a half-tone reproduction of a photograph of wells showing the results of elispot assays where splenocytes obtained from the mice (the study results of which are shown in FIG. 7B) were exposed to Mesothelin peptide nos. 278 (SEQ ID NO:2), 279 (SEQ ID NO:3), or 280 (SEQ ID NO:4).
Figure 7C:
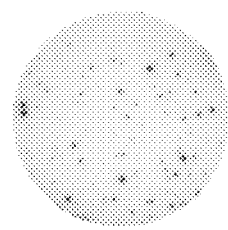
Figure 7C:
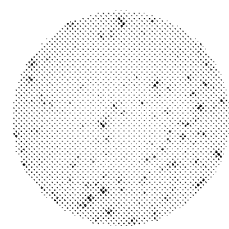

The results in FIG. 7A indicate that when the immune response was separately assessed for each peptide in the mMesothelin peptide library, the DNA-mMeso prime/Lm-mMeso38 boost elicited relatively little immune response. By contrast, the results in FIG. 7B indicate that the Ad-mMeso prime/Lm-mMeso38 boost induced relatively high immune response to mouse Mesothelin peptides nos. 278, 279, and 280, from the mouse Mesothelin peptide library. Relatively little immune response was found where other peptides from the mouse Mesothelin peptide library had been used. FIG. 7C is a photograph of the wells, where splenocytes had been exposed to Mesothelin peptide nos. 278, 279, or 280, and where the photograph illustrates the spots from the elispot assays. Thus, the results shown in FIG. 7B and FIG. 7C demonstrate that the AVprime/Lm boost regimen resulted in a specific cellular immune response to mMesothelin. Moreover, the results also indicate the breaking of tolerance against the mouse Mesothelin endogenous antigen in mice given a prime and boost immunization regimen consisting of AV and Lm vectors, with both vectors encoding mouse Mesothelin.

Example 11

The efficacy of KBMA Lm as a priming agent and/or a boosting agent was evaluated. C57BL/6 mice (3 per group) were administered with KBMA-Lm as a prime at day 0. A boost of one of the following was given at day 14: "Live" Lm, KBMA-Lm, or VV. Controls of KBMA-Lm and Live Lm were also administered at day 14. The mice were sacrificed on day 19, and splenocytes were harvested.

The *Listeria* constructs had a hly promoter operably linked to BaPA secretory sequence and ovalbumin, with genomic integration at the tRNA$^{Arg}$ locus.

The number of KBMA *Listeria monocytogenes* ΔactAΔuvrAB-OVA (KBMA Lm) injected was 3×10$^8$ bacterial particles. The KBMA Lm had been previously treated with psoralen and UV light. The amount of administered "Live" *Listeria monocytogenes* (Lm-ΔactAΔuvrAB-OVA) was 1×10$^6$ cfu. The number of administered vaccinia virus-derived vector (VV-OVA) was 1×10$^6$ pfu.

Immune response was determined by peptide-pulsing the splenocytes with a standard octapeptide peptide derived from ovalbumin (OVA$_{257-264}$), and measuring ovalbumin-specific immune response by way of intracellular staining (ICS) assays for IFN-γ.

Figure 8:
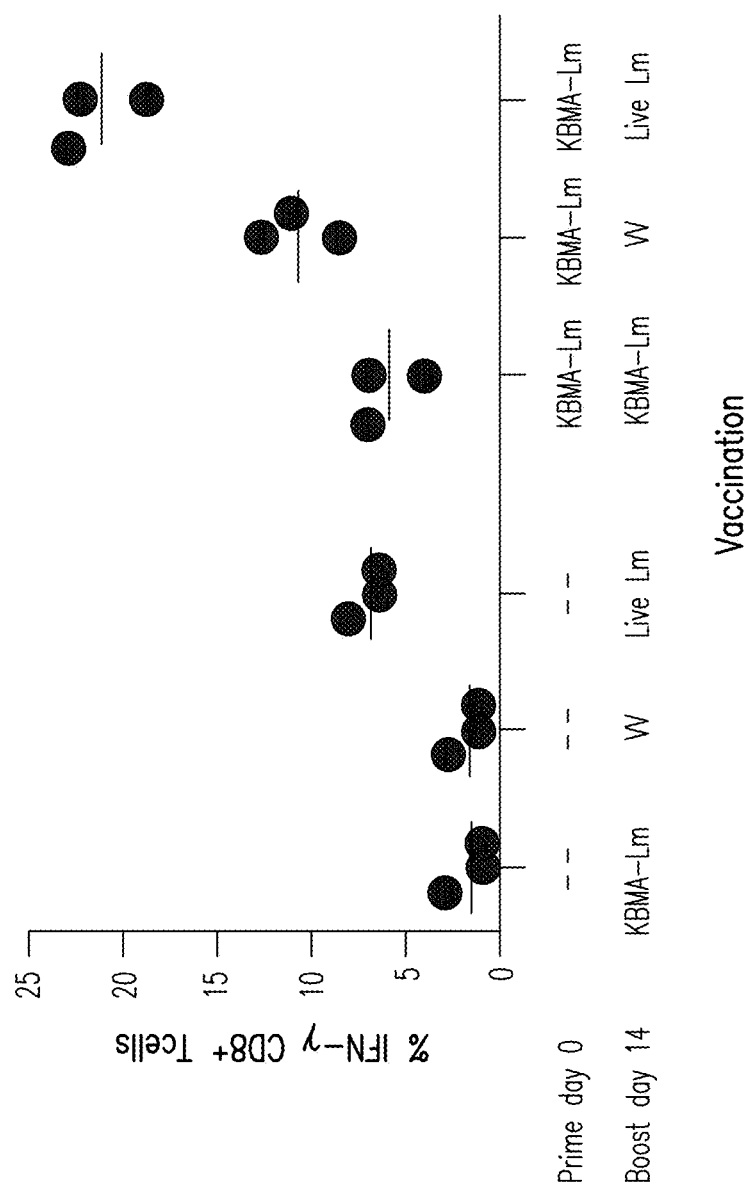
FIG. 8 is a graph showing the OVA specific cellular immune responses resulting from prime-boost regimens using KBMA *Listeria monocytogenes* encoding OVA as prime, and as boost KBMA *Listeria monocytogenes*, Vaccinia virus, or "live" *Listeria monocytogenes*. All of the "boost" vectors encoded OVA.

As seen from the results, shown in FIG. 8, KBMA-Lm was active as a priming agent. The KBMA-Lm prime/live Lm boost elicited the highest level of immune response, where lesser levels of immune response occurred with the heterologous KBMA-Lm prime/VV boost vaccine.

Example 12

Figure 9B:
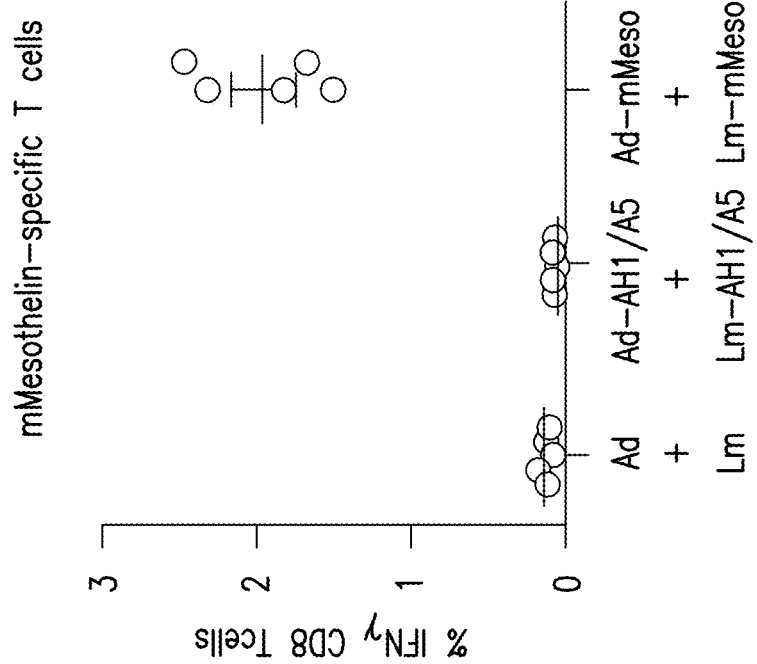
FIG. 9B shows mMesothelin-specific T cell responses in vaccinated mice.
Figure 9A:
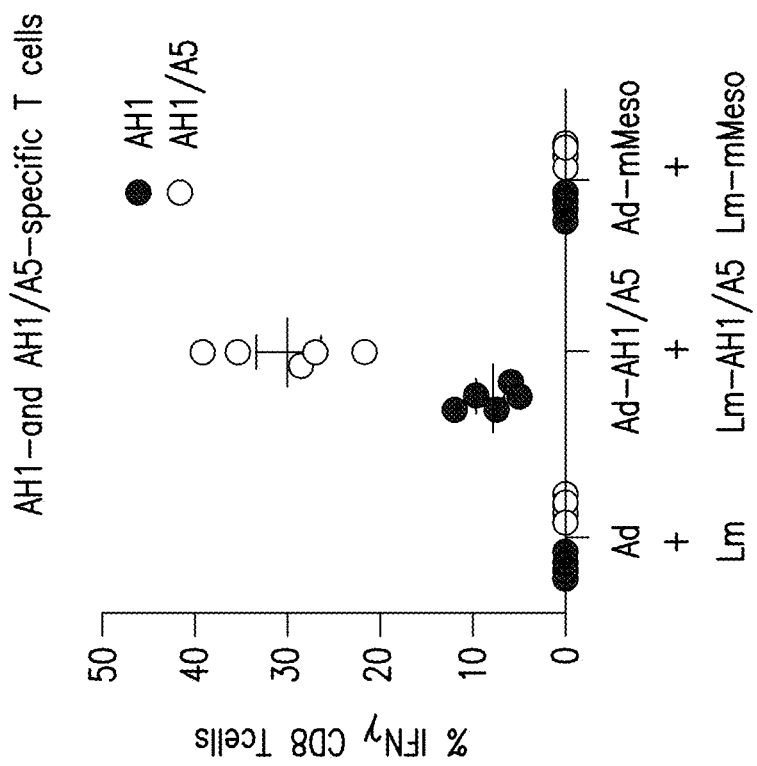
FIG. 9A shows AH- and AH1/A5-specific T cell responses in vaccinated mice.
Figure 9C:
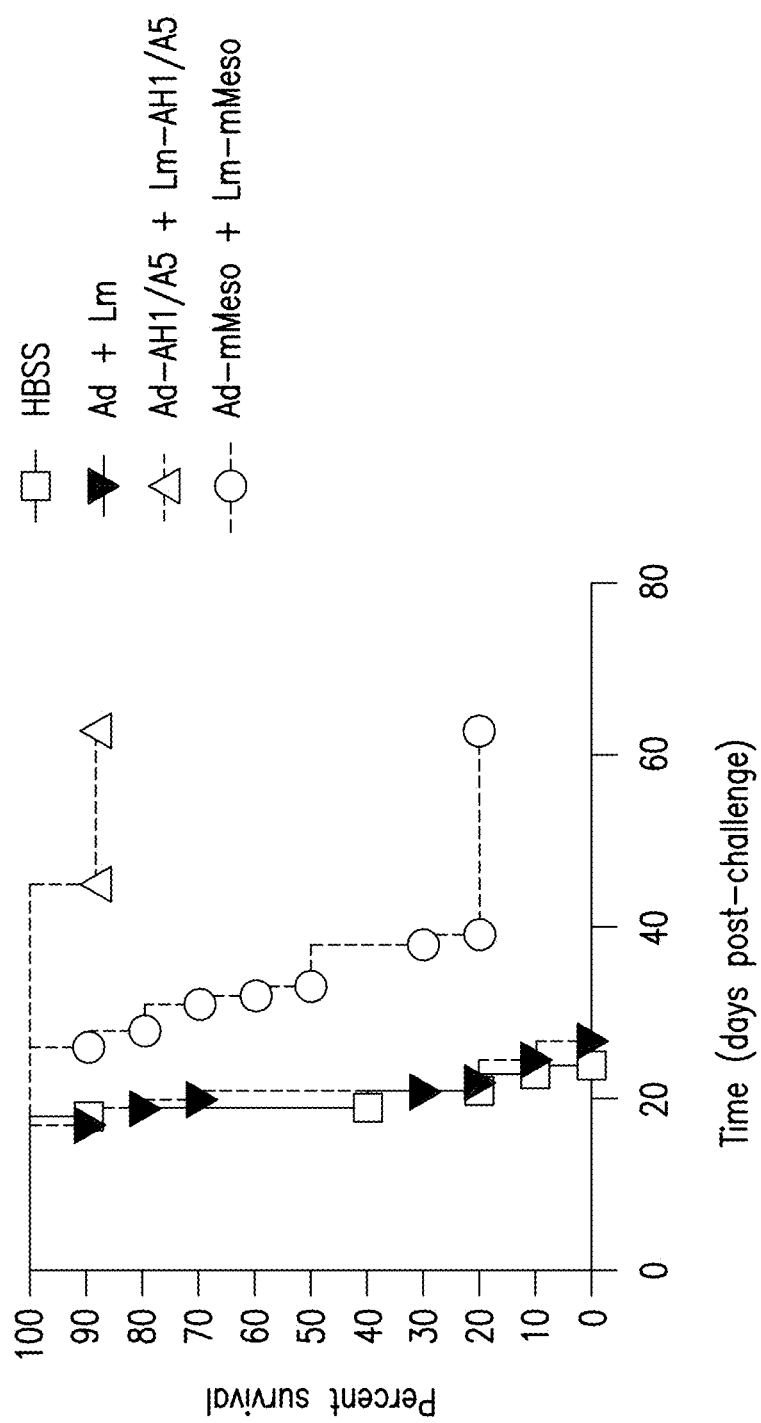
FIG. 9C shows survival data for vaccinated mice following CT26 tumor challenge.

Fifteen Balb/c mice per group were vaccinated intramuscularly with 1e8 pfu of empty adenovirus (i.e., adenovirus not expressing AH1, AH1/A5, or mMesothelin) or adenovirus expressing AH1/A5 or murine Mesothelin (mMesothelin). 21 days later, the mice were boosted intravenously with 5e6 cfu of Lm not encoding a heterologous antigen or Lm expressing AH1/A5 or mMesothelin. AH1/A5 is described (see, e.g., Brockstedt, et al. (2004) Proc. Natl. Acad. Sci. USA 101:13832-13837). Spleens from five mice per group were harvested after five days to assess AH1/A5 (FIG. 9A) and mMesothelin (FIG. 9B) immune responses. One week after the boost vaccination, the remaining mice were challenged with 4e5 CT26 cells intravenously. Mice were monitored for survival (FIG. 9C). In FIGS. 9A-9C, "Ad" denotes empty adenovirus, "Lm" denotes *L. monocytogenes* not encoding a heterologous antigen, "Ad-AH1/A5" denotes adenovirus expressing AH1/A5, "Ad-mMeso" denotes adenovirus expressing murine Mesothelin, "Lm-AH1/A5" denotes *L. monocytogenes* encoding AH1/A5, and "Lm-mMeso" denotes *L. monocytogenes* encoding murine Mesothelin.

As shown in FIG. 9A, prime/boost with Ad-AH1/A5 prime and Lm-AH1/A5 boost resulted in substantial antigen-specific CD8+ T cell immune response, according to ICS assays. AH1 peptide and AH1/A5 peptide are derived from gp70, an endogenous protein of CT26 tumor cells. Splenocyte incubation mixtures were supplemented with the AH1 peptide or AH1/A5 peptide, as indicated. Gp70 is an endogenous protein of CT26. CD8+ T cell immune response was greater where splenocytes were incubated with added AH1/A5 peptide, and lesser with added AH1 peptide.

Specificity of the immune response was demonstrated as follows. Prime/boost with empty Adenovirus and Lm not encoding a heterologous Ag did not result in detectable CD8+ T cell immune response. Also, prime/boost with vectors expressing murine Mesothelin did not result in detectable AH- or AH1/A5-specific CD8+ T cell immune responses, again demonstrating specificity of the immune response (FIG. 9A).

The data shown in FIG. 9B demonstrate prime/boost stimulation of an immune response against another heterologous antigen, namely mMesothelin, and that the immune response was specific for this antigen. Specificity was demonstrated by the failure of empty Ad prime/Lm (not encoding heterologous Ag) boost, or Ad AH1/A5 prime/Lm AH1/A5 boost, to stimulate mMesothelin specific CD8+ T cell immune responses.

The data shown in FIG. 9C demonstrate that the Ad-AH1/A5 prime/Lm-AH1/A5 boost increases survival to challenge with CT26 tumor cells. The figure also demonstrates that Ad-mMeso prime/Lm-mMeso increases survival to the CT26 tumor cell challenge. Prime boost treatment with empty vectors (empty Ad; Lm not encoding heterologous Ag) did not alter survival, as compared to treatment with HBSS (FIG. 9C).

---

What is claimed is:

1. A method for enhancing an immune response in a mammal to a cancerous cell present within the mammal, comprising:
administering to the mammal an effective amount of a boost dose of a vaccine comprising an attenuated *Listeria* that encodes an expressible, immunologically active portion of a target antigen expressed by the cancerous cell that is heterologous to the attenuated *Listeria*, wherein the mammal previously had been administered an effective amount of a prime dose of an inactivated tumor cell vaccine expressing a nucleic acid that encodes granulocyte macrophage-colony stimulation factor (GM-CSF).

2. The method of claim 1, wherein the inactivated tumor cell vaccine comprises inactivated autologous tumor cells.

3. The method of claim 1, wherein the inactivated tumor cell vaccine comprises inactivated allogeneic tumor cells.

4. The method of claim 1, wherein the cancerous cell is an adenocarcinoma cell.

5. The method of claim 2, wherein the cancerous cell is an adenocarcinoma cell.

6. The method of claim 3, wherein the cancerous cell is an adenocarcinoma cell.

7. The method of claim 1, wherein the attenuated *Listeria* comprises a mutation that inactivates ActA, InlB, or both ActA and InlB.

8. The method of claim 2, wherein the attenuated *Listeria* is ΔactAΔinlB.

9. The method of claim 1, wherein the attenuated *Listeria* is killed but metabolically active ("KBMA").

10. The method of claim 1, wherein the target antigen is Annexin II.

* * * * *